United States Patent
Saldanha et al.

(10) Patent No.: US 10,875,909 B2
(45) Date of Patent: *Dec. 29, 2020

(54) HUMANIZED ANTIBODIES THAT RECOGNIZE ALPHA-SYNUCLEIN

(71) Applicant: PROTHENA BIOSCIENCES LIMITED, Dublin (IE)

(72) Inventors: Jose Saldanha, Middlesex (GB); Tarlochan S. Nijjar, Orinda, CA (US)

(73) Assignee: PROTHENA BIOSCIENCES LIMITED, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/795,479

(22) Filed: Feb. 19, 2020

(65) Prior Publication Data
US 2020/0277362 A1    Sep. 3, 2020

Related U.S. Application Data

(63) Continuation of application No. 16/144,923, filed on Sep. 27, 2018, now Pat. No. 10,597,441, which is a continuation of application No. 15/587,255, filed on May 4, 2017, now Pat. No. 10,118,960, which is a continuation of application No. 14/937,792, filed on Nov. 10, 2015, now Pat. No. 9,670,273, which is a
(Continued)

(51) Int. Cl.
*A61K 49/00* (2006.01)
*C07K 16/18* (2006.01)
*A61K 49/16* (2006.01)
*A61K 51/10* (2006.01)
*A61K 39/00* (2006.01)

(52) U.S. Cl.
CPC .......... *C07K 16/18* (2013.01); *A61K 49/0004* (2013.01); *A61K 49/0058* (2013.01); *A61K 49/16* (2013.01); *A61K 51/1018* (2013.01); *A61K 2039/505* (2013.01); *C07K 2317/24* (2013.01); *C07K 2317/55* (2013.01); *C07K 2317/56* (2013.01); *C07K 2317/565* (2013.01); *C07K 2317/567* (2013.01); *C07K 2317/64* (2013.01); *C07K 2317/71* (2013.01); *C07K 2317/76* (2013.01); *C07K 2317/92* (2013.01)

(58) Field of Classification Search
None
See application file for complete search history.

(56) References Cited

U.S. PATENT DOCUMENTS 6,719,971 B1   4/2004  Carter et al.
6,881,557 B2   4/2005  Foote et al.
(Continued)

FOREIGN PATENT DOCUMENTS

EP    2234600 B1    8/2014
JP    H4-217630     8/1992
(Continued)

OTHER PUBLICATIONS

Masliah et al., "Effects of α-Synuclein Immunization in a Mouse Model of Parkinson's Disease", *Neuron*, 46:857-866, (2005).
(Continued)

*Primary Examiner* — Aurora M Fontainhas
(74) *Attorney, Agent, or Firm* — Alston & Bird LLP

(57) ABSTRACT

The present application discloses humanized 1H7 antibodies. The antibodies bind to human alpha synuclein and can be used for treatment and diagnosis of Lewy body disease.

17 Claims, 8 Drawing Sheets

Specification includes a Sequence Listing.

Related U.S. Application Data continuation of application No. 14/340,355, filed on Jul. 24, 2014, now Pat. No. 9,217,030, which is a continuation of application No. 13/750,983, filed on Jan. 25, 2013, now Pat. No. 8,790,644.

(60) Provisional application No. 61/711,207, filed on Oct. 8, 2012, provisional application No. 61/591,835, filed on Jan. 27, 2012.

(56) References Cited

U.S. PATENT DOCUMENTS

| | | |
|---|---|---|
| 7,022,500 B1 | 4/2006 | Queen et al. |
| 7,358,331 B2 | 4/2008 | Chilcote et al. |
| 7,566,771 B1 | 7/2009 | Adair et al. |
| 7,657,380 B2 | 2/2010 | Lazar et al. |
| 7,674,599 B2 | 3/2010 | Chilcote et al. |
| 7,910,333 B2 | 3/2011 | Chilcote et al. |
| 7,919,088 B2 | 4/2011 | Schenk et al. |
| 8,092,801 B2 | 1/2012 | Schenk et al. |
| 8,609,820 B2 | 12/2013 | Saldanha et al. |
| 8,790,644 B2 | 7/2014 | Saldanha et al. |
| 9,217,030 B2 | 12/2015 | Saldanha et al. |
| 9,234,031 B2 | 1/2016 | Saldanha et al. |
| 9,556,259 B2 | 1/2017 | Saldanha et al. |
| 9,605,056 B2 | 3/2017 | Barbour et al. |
| 9,670,273 B2 | 6/2017 | Saldanha et al. |
| 9,884,906 B2 | 2/2018 | Saldanha et al. |
| 10,081,674 B2 | 9/2018 | Barbour et al. |
| 10,084,674 B2 | 9/2018 | Barbour et al. |
| 10,118,960 B2 | 11/2018 | Saldanha et al. |
| 10,301,382 B2 | 5/2019 | Barbour et al. |
| 10,450,369 B2 | 10/2019 | Saldanha et al. |
| 10,513,555 B2 | 12/2019 | Garidel et al. |
| 10,597,441 B2 | 3/2020 | Saldanha et al. |
| 2006/0008883 A1 | 1/2006 | Lazar et al. |
| 2008/0014194 A1 | 1/2008 | Schenk et al. |
| 2009/0010924 A1 | 1/2009 | Wu et al. |
| 2009/0202432 A1 | 8/2009 | Schenk et al. |
| 2009/0208487 A1 | 8/2009 | Schenk et al. |
| 2010/0031377 A1 | 2/2010 | Schenk et al. |
| 2010/0086545 A1 | 4/2010 | Schenk et al. |
| 2010/0098712 A1 | 4/2010 | Adler et al. |
| 2010/0203631 A1 | 8/2010 | Chilcote et al. |
| 2011/0052498 A1 | 3/2011 | Lannfelt et al. |
| 2012/0204275 A1 | 8/2012 | Schenk |
| 2012/0276019 A1 | 11/2012 | Charles et al. |
| 2014/0127131 A1 | 5/2014 | Barbour et al. |
| 2014/0275495 A1 | 9/2014 | Saldanha et al. |
| 2015/0024433 A1 | 1/2015 | Saldanha et al. |
| 2015/0056187 A1 | 2/2015 | Saldanha et al. |
| 2015/0079074 A1 | 3/2015 | Garidel et al. |
| 2015/0259404 A1 | 9/2015 | Barbour et al. |
| 2016/0251416 A1 | 9/2016 | Saldanha et al. |
| 2018/0016329 A1 | 1/2018 | Saldanha et al. |
| 2018/0201669 A1 | 7/2018 | Saldanha et al. |
| 2019/0153080 A1 | 5/2019 | Saldanha et al. |
| 2019/0315843 A1 | 10/2019 | Barbour et al. |
| 2020/0140534 A1 | 5/2020 | Garidel et al. |

FOREIGN PATENT DOCUMENTS

| | | |
|---|---|---|
| JP | 2000-510813 | 8/2000 |
| JP | 2008-520551 | 6/2008 |
| JP | 2013-5000976 | 1/2013 |
| JP | 2013-504540 | 2/2013 |
| JP | 2013-521769 | 6/2013 |
| JP | 2014-522843 | 9/2014 |
| JP | 2011-246484 | 12/2014 |
| JP | 2015-508062 | 3/2015 |
| WO | WO 2004/039234 A2 | 5/2004 |
| WO | WO 2004/041067 | 5/2004 |
| WO | WO 2005/047860 A2 | 5/2005 |
| WO | WO 2007/011907 A2 | 1/2007 |
| WO | WO 2008/011348 A2 | 1/2008 |
| WO | WO 2008/103472 A2 | 8/2008 |
| WO | WO 2008/116103 A2 | 9/2008 |
| WO | WO 2010/069603 A1 | 6/2010 |
| WO | WO 2011/090720 A2 | 7/2011 |
| WO | WO 2011/107544 A1 | 9/2011 |
| WO | WO 2011/127324 A2 | 10/2011 |
| WO | WO 2011/155607 A1 | 12/2011 |
| WO | WO 2011/156328 A1 | 12/2011 |
| WO | WO 2012/009631 A1 | 1/2012 |
| WO | WO 2012/051147 A1 | 4/2012 |
| WO | WO 2012/160536 A1 | 11/2012 |
| WO | WO 2012/177997 A1 | 12/2012 |
| WO | WO 2013/063516 A1 | 5/2013 |
| WO | WO 2013/066866 A1 | 5/2013 |
| WO | WO 2013/112945 A1 | 8/2013 |
| WO | WO 2014/033074 A1 | 3/2014 |
| WO | WO 2014/058924 A2 | 4/2014 |
| WO | WO 2015/001504 A2 | 1/2015 |
| WO | WO 2015/155694 A1 | 10/2015 |

OTHER PUBLICATIONS

Masliah et al., "Passive Immunization Reduces Behavioral and Neuropathological Deficits in an Alpha-Synuclein Transgenic Model of Lewy Body Disease", PLoS ONE, 6(4):e19338, pp. 1-17, (Apr. 2011).

PCT/US2002/062290 Written Opinion and Search Report dated Jan. 28, 2013.

PCT/US2013/023307 Written Opinion and Search Report dated May 13, 2013.

Finlay et al., "Affinity Maturation of a Humanized Rat Antibody for Anti-RAGE Therapy: Comprehensive Mutagenesis Reveals a Hight Level of Mutational Plasticity Both Inside and Outside the Complementarity-Determining Regions", J. Mol. Biol., 388, pp. 541-558, (2009).

PCT/US2013/063945 Written Opinion and Search Report dated Apr. 22, 2014.

PCT/US2013/063945 Invitation to Pay Additional Fees dated Feb. 6, 2014.

Mihara, et al., "CTLA4Ig inhibits T cell-dependent B-cell maturation in murine systemic lupus erythematosus," J. Clin. Invest., vol. 106, No. 1, pp. 91-101 (2000).

Hackett, et al., "Recombinant Mouse-Human Chimeric Antibodies as Calibrators in Immunoassays That Measure Antibodies to *Toxoplasma Gondii*," J. Clin. Microbiol. vol. 36, No. 5, pp. 1277-1284 (1998).

Yang, et al., "Structural basis of immunosuppression by the therapeutic antibody daclizumab," Cell Research, 20:1361-1371 (2010).

Genbank Accession No. AAC28255.1, "Immunoglobulin kappa light chain [Mus musculus]," Dec. 15, 1999.

Genbank Accession No. 3NFP A, "Chain A, Crystal Structure of the Fab Fragment of Therapeutic Antibody Daclizumab in Complex With Il-2ra (cd25) Ectodomain," Oct. 19, 2013.

Genbank Accession No. AAF88044.1, "Immunoglobulin heavy chain variable regions [Mus musculus]," Jul. 27, 2000.

Choi, et al., "Fine epitope mapping of monoclonal antibodies specific to human alpha-synuclein," Neurosci Lett., 17;397(1-2):53-58 (2006) Abstract only.

Gonzalas, et al., "SDR grafting of a murine antibody using multiple human germline templates to minimize its immunogenicity," Molecular Immunology, 41:863-872 (2004).

PCT/US2013/023307 International Preliminary Report on Patentability and Written Opinion dated Jul. 29, 2014.

U.S. Appl. No. 12/156,441 Non-Final Office Action dated Nov. 10, 2014.

U.S. Appl. No. 14/049,169 Restriction Requirement dated Jul. 16, 2014.

PCT/IB2014/062806 Invitation to Pay Additional Fees and Where Applicable Protest Fee dated Oct. 29, 2014.

Wang, W., "Instability, stabilization, and formulation of liquid protein pharmaceuticals," Int. J. Pharmaceutics, 185(2):129-188 (1999).

Wang, et at., "Antibody Structure, Instability, and Formulation", Journal of Pharmaceutical Sciences, vol. 96:1 pp. 1-26 (Jan. 2007).

(56) References Cited

OTHER PUBLICATIONS

Warne, et al., "Development of high concentration protein biopharmaceuticals: The use of platform approaches in formulation development," *European Journal of Pharmaceutics and Biopharmaceutics*, 78:208-212 (2011).
Daugherty, et al., "Formulation and Delivery Issues for Monoclonal Antibody Therapeutics," *Advanced Drug Delivery Reviews*, 58(5-6):686-42 (2006) with permission Elsevier.
LBD Association, Inc. 2013, "Incidence of Lewy body dementias in a general population", http://222.lbda.org.
PCT/IB2014/062806 International Search Report and Written Opinion of the International Searching Authority dated Apr. 24, 2015.
EP 12844433.8 European Search Report dated Feb. 17, 2015.
U.S. Appl. No. 14/340,342 Non-Final Office Action dated Mar. 3, 2015.
U.S. Appl. No. 14/049,169 Non-Final Office Action dated Feb. 10, 2015.
Wang, "Advances in the production of human monoclonal antibodies," Antibody Technology Journal, 1: 1-4 (2011).
EP 13740871.2 European Search Report dated Jun. 3, 2015.
Nasstrom, et al., "Antibodies against Alpha-synuclein Reduce Oligomerization in Living Cells," *PloS ONE*, vol. 6, Issue 10, e27230 (Oct. 2011).
U.S. Appl. No. 14/340,555 Non-Final Office Action dated Apr. 8, 2015.
U.S. Appl. No. 14/049,169 Final Office Action and Telephone Interview dated Oct. 2, 2015.
PCT/IB2015/052524 Search Report and Written Opinion dated Jul. 3, 2015.
U.S. Appl. No. 14/156,441 Final Office Action dated Jun. 8, 2016.
U.S. Appl. No. 14/049,169 Non-Final Office Action dated Mar. 30, 2016.
U.S. Appl. No. 14/322,797 Restriction Requirement dated Aug. 29, 2016.
EP13845625 European Extended Search Report dated Jul. 18, 2016.
U.S. Appl. No. 14/156,441 Notice of Allowance dated Sep. 20, 2016.
U.S. Appl. No. 14/937,792 Non-Final Office Action dated Aug. 30, 2016.
U.S. Appl. No. 14/937,792 Examiner Initiated Interview Summary dated Aug. 30, 2016.
U.S. Appl. No. 14/937,792 Examiner Initiated Interview Summary dated Feb. 2, 2017.
U.S. Appl. No. 14/937,792 Notice of Allowance dated Feb. 2, 2017.
U.S. Appl. No. 14/156,441 Examiner Initiated Interview Summary dated Nov. 10, 2014.
U.S. Appl. No. 14/049,169 Examiner Initiated Interview Summary dated Feb. 10, 2015.
U.S. Appl. No. 14/049,169 Examiner Initiated Interview Summary dated Oct. 2, 2015.
U.S. Appl. No. 14/049,169 Examiner Initiated Interview Summary dated Nov. 1, 2016.
U.S. Appl. No. 14/049,169 Notice of Allowance dated Nov. 1, 2016.
U.S. Appl. No. 14/322,797 Non-Final Office Action dated Jan. 3, 2017.
PCT/US2013/063945 International Preliminary Report on Patentability dated Apr. 8, 2015.
PCT/US2012/062290 International Preliminary Report on Patentability dated Apr. 29, 2014.
PCT/IB2014/062806 International Preliminary Report on Patentability dated Jan. 5, 2016.
PCT/IB2015/052524 International Preliminary Report on Patentability dated Oct. 12, 2016.
Zhang et al., "Conformation-dependent scFv antibodies specifically recognize the oligomers assembled from various amyloids and show colocalization of amyloid fibrils with oligomers in patients with amyloidosis," Biochimica et Biophysica Acta (BBA)—Protein & Proteomics, 1814(2):1703-1712, (2011).
Jones et al., "Deimmunization of Monoclonal Antibodies," *Therapeutic Antibodies: Methods and Protocols*, 525:405-423, (2009).
Roche Data Sheet, "Herceptin 140625" Prepared Jun. 25, 2014.
Xolair, "Highlights of Prescribing Information", Genentech, Inc. (2003).
U.S. Appl. No. 15/387,580 Notice of Allowance dated Sep. 28, 2017.
U.S. Appl. No. 15/429,962 Non-Final Office Action dated Sep. 22, 2017.
U.S. Appl. No. 14/322,797 Final Office Action dated Jul. 19, 2017.
Mahler, et al., "Trends n Formulation and Drug Delivery for Antibodies", Process Scale Purification of Antibodies, Second Edition, Edited by Uwe Gottschalk, 2017 John Wiley & Sons, Inc. Published 2017 by John Wiley & Sons, Inc.
U.S. Appl. No. 14/322,797 Non-Final Office Action dated Mar. 2, 2018.
Amgen, Inc., Blincyto® (blinatumomab) Highlights of Prescribing Information and Full Prescribing Information revised May 2018.
U.S. Appl. No. 15/587,255 Notice of Allowance and Examiner Initiated Interview Summary dated Jun. 27, 2018.
U.S. Appl. No. 14/322,797 Final Office Action dated Aug. 7, 2018.
U.S. Appl. No. 15/857,104 Non-Final Office Action dated Jul. 23, 2018.
Rudikoff, et al., "Single amino acid substitution altering antigen-binding specificity," *Proc. Natl. Acad. Sci. USA*, vol. 79, pp. 1979-1983, (Mar. 1982).
Tamura, et al., "Structural Correlates of an Anticarcinoma Antibody: Identification of Specificity-Determining Residues (SDRs) and Development of a Minimally Immunogenic Antibody Variant by Retention of SDRs Only," *J Immunol*, 164:1432-1441, (2000).
U.S. Appl. No. 16/107,949 Notice of Allowance and Interview Summary dated Jan. 9, 2019.
EP 18155441.1 Extended European Search Report dated Jun. 18, 2018.
U.S. Appl. No. 15/857,104 Notice of Allowance dated Jan. 29, 2019.
EP 18206357.8 Extended European Search Report dated Apr. 23, 2019.
U.S. Appl. No. 15/857,104 Notice of Allowance dated Jun. 18, 2019.
U.S. Appl. No. 14/322,797 Notice of Allowance and Interview Summary dated Aug. 2, 2019.
Ishihara et al., "Accelerated purification process development of monoclonal antibodies for shortening time to clinic," Journal of Chromatography, vol. 1176, No. 1-2, pp. 149-156, (Nov. 7, 2007) abstract only.
EP 18212531.0 Extended European Search Report dated Jun. 13, 2019.
"Antibody Purification Handbook", Antibody Purification Handbook, Amersham Biosciences, Uppsala, SE, pp. FP-107, XP002357261 [A] 1-14 * the whole document * (Jan. 1, 2002).
U.S. Appl. No. 16/417,309 Non-final Office Action dated Oct. 25, 2019.
U.S. Appl. No. 16/144,923 Notice of Allowance and Interview Summary dated Nov. 15, 2019.
U.S. Appl. No. 16/385,968 Notice of Allowance and Interview Summary dated Jan. 3, 2020.
U.S. Appl. No. 16/417,309 Notice of Allowance dated Mar. 13, 2020.

1H7 VH alignment

| Kabat Numbering | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| m1H7VH | Q | V | Q | L | Q | Q | S | G | P | E | L | V | K | P | G | T | S | V | K | I |
| BAC02037 | Q | V | K | L | V | Q | S | G | A | E | V | K | K | P | G | A | S | V | K | V |
| Hu1H7VHv1 | Q | V | K | L | V | Q | S | G | A | E | L | K | K | P | G | A | S | V | K | V |
| Hu1H7VHv2 | Q | V | K | L | V | Q | S | G | A | E | V | K | K | P | G | A | S | V | K | V |
| Hu1H7VHv3 | Q | V | K | L | V | Q | S | G | A | E | V | K | P | G | A | S | V | K | V |
| Hu1H7VHv4 | Q | V | K | L | V | Q | S | G | A | E | V | K | K | P | G | A | S | V | K | V |
| Hu1H7VHv5 | Q | V | K | L | V | Q | S | G | A | E | V | K | K | P | G | A | S | V | K | V |

| Kabat Numbering | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|
| m1H7VH | S | C | K | A | S | G | Y | S | F | T | S | Y | Y | I | H | W | V | K | Q | S |
| BAC02037 | S | C | K | A | S | G | Y | T | F | T | S | F | G | I | S | W | V | R | Q | A |
| Hu1H7VHv1 | S | C | K | A | S | G | Y | S | F | T | S | Y | Y | I | H | W | V | K | Q | A |
| Hu1H7VHv2 | S | C | K | A | S | G | Y | T | F | T | S | Y | Y | I | H | W | V | K | Q | A |
| Hu1H7VHv3 | S | C | K | A | S | G | Y | T | F | T | S | Y | Y | I | H | W | V | R | Q | A |
| Hu1H7VHv4 | S | C | K | A | S | G | Y | S | F | T | S | Y | Y | I | H | W | V | R | Q | A |
| Hu1H7VHv5 | S | C | K | A | S | G | Y | T | F | T | S | Y | Y | I | H | W | V | R | Q | A |

| Kabat Numbering | 41 | 42 | 43 | 44 | 45 | 46 | 47 | 48 | 49 | 50 | 51 | 52 | 52A | 53 | 54 | 55 | 56 | 57 | 58 | 59 |
|---|---|---|---|---|---|---|---|---|---|---|---|---|---|---|---|---|---|---|---|---|
| m1H7VH | P | G | Q | G | L | E | W | I | G | W | I | Y | P | G | S | G | N | T | K | Y |
| BAC02037 | P | G | Q | G | L | E | W | M | G | W | I | S | P | Y | N | G | D | T | N | K |
| Hu1H7VHv1 | P | G | Q | G | L | E | W | I | G | W | I | Y | P | G | S | G | N | T | K | Y |
| Hu1H7VHv2 | P | G | Q | G | L | E | W | I | G | W | I | Y | P | G | S | G | N | T | K | Y |
| Hu1H7VHv3 | P | G | Q | G | L | E | W | M | G | W | I | Y | P | G | S | G | N | T | K | Y |
| Hu1H7VHv4 | P | G | Q | G | L | E | W | I | G | W | I | Y | P | G | S | G | N | T | K | Y |
| Hu1H7VHv5 | P | G | Q | G | L | E | W | M | G | W | I | Y | P | G | S | G | N | T | K | Y |

FIG. 1A

1H7 VH alignment

| Kabat Numbering | 60 | 61 | 62 | 63 | 64 | 65 | 66 | 67 | 68 | 69 | 70 | 71 | 72 | 73 | 74 | 75 | 76 | 77 | 78 | 79 |
|---|---|---|---|---|---|---|---|---|---|---|---|---|---|---|---|---|---|---|---|---|
| m1H7VH | S | E | K | F | K | G | K | A | T | L | T | A | D | T | S | S | S | T | A | Y |
| BAC02037 | A | Q | N | L | Q | G | R | V | T | M | T | T | D | T | S | T | S | T | A | Y |
| Hu1H7VHv1 | S | E | K | F | K | G | R | A | T | L | T | A | D | T | S | T | S | T | A | Y |
| Hu1H7VHv2 | S | E | K | F | K | G | R | A | T | L | T | A | D | T | S | T | S | T | A | Y |
| Hu1H7VHv3 | S | E | K | F | K | G | R | A | T | M | T | A | D | T | S | T | S | T | A | Y |
| Hu1H7VHv4 | S | E | K | F | K | G | R | A | T | L | T | A | D | T | S | T | S | T | A | Y |
| Hu1H7VHv5 | S | E | K | F | K | G | R | A | T | M | T | A | D | T | S | T | S | T | A | Y |

| Kabat Numbering | 80 | 81 | 82 | 82A | 82B | 82C | 83 | 84 | 85 | 86 | 87 | 88 | 89 | 90 | 91 | 92 | 93 | 94 | 95 | 96 |
|---|---|---|---|---|---|---|---|---|---|---|---|---|---|---|---|---|---|---|---|---|
| m1H7VH | M | Q | L | S | S | L | T | S | E | D | S | A | V | Y | F | C | A | R | D | G |
| BAC02037 | M | E | L | R | S | L | R | S | D | D | T | A | V | Y | Y | C | A | R | D | R |
| Hu1H7VHv1 | M | E | L | R | S | L | R | S | D | D | T | A | V | Y | F | C | A | R | D | G |
| Hu1H7VHv2 | M | E | L | R | S | L | R | S | D | D | T | A | V | Y | F | C | A | R | D | G |
| Hu1H7VHv3 | M | E | L | R | S | L | R | S | D | D | T | A | V | Y | Y | C | A | R | D | G |
| Hu1H7VHv4 | M | E | L | R | S | L | R | S | D | D | T | A | V | Y | F | C | A | R | D | G |
| Hu1H7VHv5 | M | E | L | R | S | L | R | S | D | D | T | A | V | Y | Y | C | A | R | D | G |

| Kabat Numbering | 97 | 98 | 99 | 100 | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|
| m1H7VH | C | Y | G | F | A | Y | W | G | Q | G | T | L | V | T | V | S | – |
| BAC02037 | G | S | M | S | D | Y | W | G | Q | G | T | L | V | T | V | S | S |
| Hu1H7VHv1 | C | Y | G | F | A | Y | W | G | Q | G | T | L | V | T | V | S | S |
| Hu1H7VHv2 | C | Y | G | F | A | Y | W | G | Q | G | T | L | V | T | V | S | S |
| Hu1H7VHv3 | C | Y | G | F | A | Y | W | G | Q | G | T | L | V | T | V | S | S |
| Hu1H7VHv4 | S | Y | G | F | A | Y | W | G | Q | G | T | L | V | T | V | S | S |
| Hu1H7VHv5 | S | Y | G | F | A | Y | W | G | Q | G | T | L | V | T | V | S | S |

FIG. 1B

1H7 VH alignment

| Kabat Numbering | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| m1H7VL    | D | I | V | L | T | Q | S | P | A | S | L | S | V | S | L | G | Q | R | A | T |
| AAY33358  | D | I | Q | L | T | Q | S | P | S | S | L | S | A | S | V | G | D | R | V | T |
| Hu1H7VLv1 | D | I | Q | L | T | Q | S | P | S | S | L | S | A | S | V | G | D | R | V | T |
| Hu1H7VLv2 | D | I | Q | L | T | Q | S | P | S | S | L | S | A | S | V | G | D | R | V | T |
| Hu1H7VLv3 | D | I | Q | L | T | Q | S | P | S | S | L | S | A | S | V | G | D | R | V | T |
| Hu1H7VLv4 | D | I | Q | L | T | Q | S | P | S | S | L | S | A | S | V | G | D | R | V | T |

| Kabat Numbering | 21 | 22 | 23 | 24 | 25 | 26 | 27 | 27A | 27B | 27C | 27D | 28 | 29 | 30 | 31 | 32 | 33 | 34 | 35 | 36 |
|---|---|---|---|---|---|---|---|---|---|---|---|---|---|---|---|---|---|---|---|---|
| m1H7VL    | I | S | C | K | A | S | Q | S | V | D | Y | D | G | D | S | Y | M | N | W | Y |
| AAY33358  | I | T | C | R | A | S | Q | - | - | - | - | G | I | R | N | D | L | G | W | Y |
| Hu1H7VLv1 | I | T | C | K | A | S | Q | S | V | D | Y | D | G | D | S | Y | M | N | W | Y |
| Hu1H7VLv2 | I | T | C | K | A | S | Q | S | V | D | Y | D | G | D | S | Y | M | N | W | Y |
| Hu1H7VLv3 | I | T | C | K | A | S | Q | S | V | D | Y | D | G | D | S | Y | M | N | W | Y |
| Hu1H7VLv4 | I | T | C | K | A | S | Q | S | V | D | Y | D | G | D | S | Y | M | N | W | Y |

| Kabat Numbering | 37 | 38 | 39 | 40 | 41 | 42 | 43 | 44 | 45 | 46 | 47 | 48 | 49 | 50 | 51 | 52 | 53 | 54 | 55 | 56 |
|---|---|---|---|---|---|---|---|---|---|---|---|---|---|---|---|---|---|---|---|---|
| m1H7VL    | Q | Q | K | P | G | Q | P | P | K | F | L | I | C | A | A | S | N | L | E | S |
| AAY33358  | Q | Q | K | P | G | K | A | P | K | L | L | I | Y | A | A | S | S | L | Q | S |
| Hu1H7VLv1 | Q | Q | K | P | G | K | A | P | K | F | L | I | C | A | A | S | N | L | E | S |
| Hu1H7VLv2 | Q | Q | K | P | G | K | A | P | K | F | L | I | Y | A | A | S | N | L | E | S |
| Hu1H7VLv3 | Q | Q | K | P | G | K | A | P | K | F | L | I | C | A | A | S | N | L | E | S |
| Hu1H7VLv4 | Q | Q | K | P | G | K | A | P | K | F | L | I | Y | A | A | S | N | L | E | S |

FIG. 2A

1H7 VH alignment

| Kabat Numbering | 57 | 58 | 59 | 60 | 61 | 62 | 63 | 64 | 65 | 66 | 67 | 68 | 69 | 70 | 71 | 72 | 73 | 74 | 75 | 76 |
|---|---|---|---|---|---|---|---|---|---|---|---|---|---|---|---|---|---|---|---|---|
| m1H7VL | G | I | P | A | R | F | S | G | S | G | S | G | T | D | F | T | L | N | I | H |
| AAY33358 | G | V | P | S | R | F | S | G | S | G | S | G | T | D | F | T | L | T | I | S |
| Hu1H7VLv1 | G | V | P | S | R | F | S | G | S | G | S | G | T | D | F | T | L | T | I | S |
| Hu1H7VLv2 | G | V | P | S | R | F | S | G | S | G | S | G | T | D | F | T | L | T | I | S |
| Hu1H7VLv3 | G | V | P | S | R | F | S | G | S | G | S | G | T | D | F | T | L | T | I | S |
| Hu1H7VLv4 | G | V | P | S | R | F | S | G | S | G | S | G | T | D | F | T | L | T | I | S |

| Kabat Numbering | 77 | 78 | 79 | 80 | 81 | 82 | 83 | 84 | 85 | 86 | 87 | 88 | 89 | 90 | 91 | 92 | 93 | 94 | 95 | 96 |
|---|---|---|---|---|---|---|---|---|---|---|---|---|---|---|---|---|---|---|---|---|
| m1H7VL | P | V | E | E | E | D | A | A | T | Y | Y | C | Q | Q | S | N | E | D | P | F |
| AAY33358 | S | L | Q | P | E | D | F | A | T | Y | Y | C | L | Q | D | Y | N | Y | P | F |
| Hu1H7VLv1 | S | L | Q | P | E | D | A | A | T | Y | Y | C | Q | Q | S | N | E | D | P | F |
| Hu1H7VLv2 | S | L | Q | P | E | D | A | A | T | Y | Y | C | Q | Q | S | N | E | D | P | F |
| Hu1H7VLv3 | S | L | Q | P | E | D | F | A | T | Y | Y | C | Q | Q | S | N | E | D | P | F |
| Hu1H7VLv4 | S | L | Q | P | E | D | F | A | T | Y | Y | C | Q | Q | S | N | E | D | P | F |

| Kabat Numbering | 97 | 98 | 99 | 100 | 101 | 102 | 103 | 104 | 105 | 106 | 107 |
|---|---|---|---|---|---|---|---|---|---|---|---|
| m1H7VL | T | F | G | S | G | T | K | L | E | I | K |
| AAY33358 | T | F | G | Q | G | T | K | L | E | I | K |
| Hu1H7VLv1 | T | F | G | Q | G | T | K | L | E | I | K |
| Hu1H7VLv2 | T | F | G | Q | G | T | K | L | E | I | K |
| Hu1H7VLv3 | T | F | G | Q | G | T | K | L | E | I | K |
| Hu1H7VLv4 | T | F | G | Q | G | T | K | L | E | I | K |

FIG. 2B

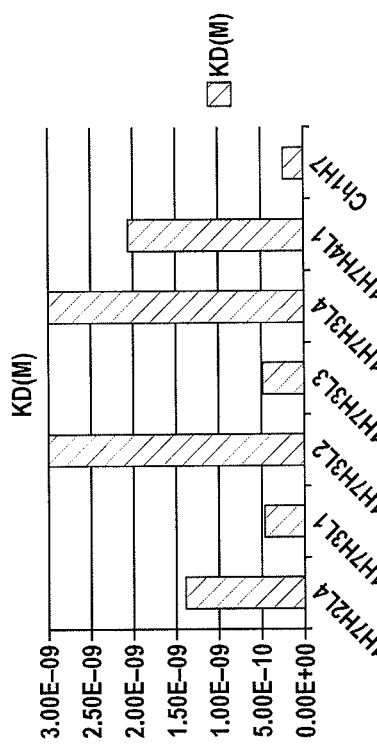
FIG. 4A
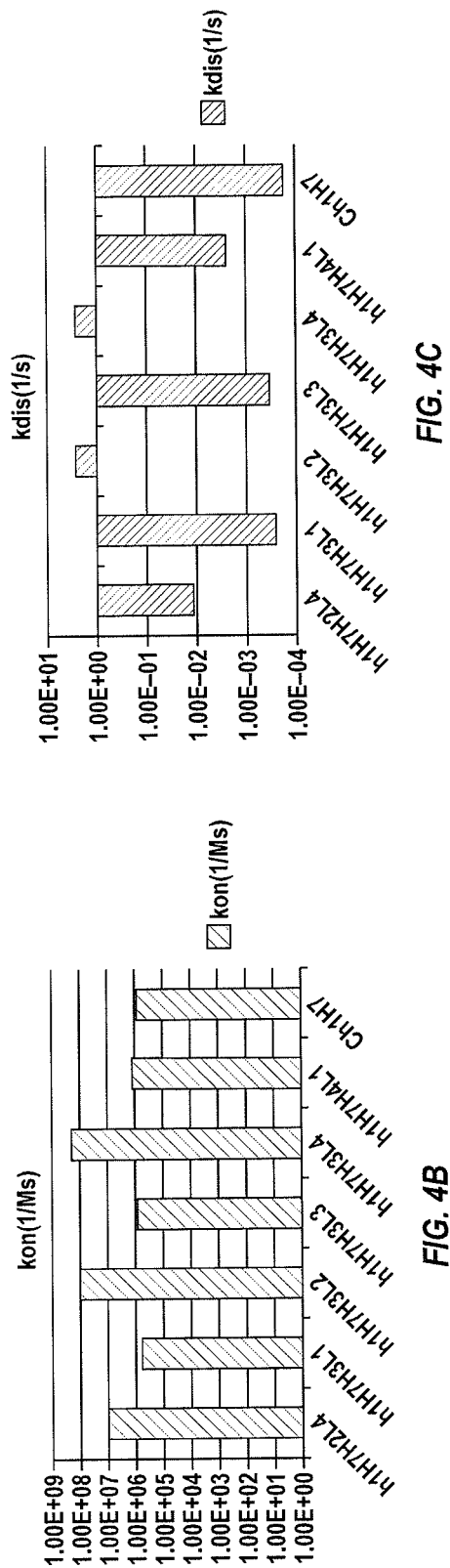
FIG. 4B
FIG. 4C

SEQUENCE LISTING

<160> NUMBER OF SEQ ID NOS: 58

<210> SEQ ID NO 1
<211> LENGTH: 140
<212> TYPE: PRT
<213> ORGANISM: Homo sapiens

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
            85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 2
<211> LENGTH: 35
<212> TYPE: PRT
<213> ORGANISM: Homo sapiens

<400> SEQUENCE: 2

Glu Gln Val Thr Asn Val Gly Gly Ala Val Val Thr Gly Val Thr Ala
1               5                   10                  15

Val Ala Gln Lys Thr Val Glu Gly Ala Gly Ser Ile Ala Ala Ala Thr
            20                  25                  30

Gly Phe Val
        35

<210> SEQ ID NO 3
<211> LENGTH: 28
<212> TYPE: PRT
<213> ORGANISM: Homo sapiens

<400> SEQUENCE: 3

Lys Glu Gln Val Thr Asn Val Gly Gly Ala Val Val Thr Gly Val Thr
1               5                   10                  15

Ala Val Ala Gln Lys Thr Val Glu Gly Ala Gly Ser
            20                  25

<210> SEQ ID NO 4
<211> LENGTH: 405
<212> TYPE: DNA
<213> ORGANISM: Artificial Sequence
<220> FEATURE:
<223> OTHER INFORMATION: Synthesized

<400> SEQUENCE: 4
atgggatgga gctgggtctt tatcttcctc ctgtcaggaa ctgcaggtgt ccattgccag      60
gtccagctgc agcagtctgg acctgagctg gtgaagcctg ggacttcagt gaagatatcc    120
tgcaaggctt ctggctacag cttcacaagc tactatatac actgggtgaa gcagagtcct    180 ggacaggga ttgagtggat tgatggatt taccctggaa gtgtaatac taagtacagt      240 gagaagttca agggcaaggc cacactgact gcagacacat cctccagcac agcctacatg    300

```
cagctcagca gcctgacatc tgaggactct gcagtctatt tctgtgcaag agatggttgc    360
tacgggtttg cttactgggg ccaagggact ctggtcactg tctct                   405
```

<210> SEQ ID NO 5
<211> LENGTH: 135
<212> TYPE: PRT
<213> ORGANISM: Artificial Sequence
<220> FEATURE:
<223> OTHER INFORMATION: Synthesized

<400> SEQUENCE: 5

Met Gly Trp Ser Trp Val Phe Ile Phe Leu Leu Ser Gly Thr Ala Gly
1               5                   10                  15

Val His Cys Gln Val Gln Leu Gln Gln Ser Gly Pro Glu Leu Val Lys
            20                  25                  30

Pro Gly Thr Ser Val Lys Ile Ser Cys Lys Ala Ser Gly Tyr Ser Phe
        35                  40                  45

Thr Ser Tyr Tyr Ile His Trp Val Lys Gln Ser Pro Gly Gln Gly Leu
    50                  55                  60

Glu Trp Ile Gly Trp Ile Tyr Pro Gly Ser Gly Asn Thr Lys Tyr Ser
65                  70                  75                  80

Glu Lys Phe Lys Gly Lys Ala Thr Leu Thr Ala Asp Thr Ser Ser Ser
                85                  90                  95

Thr Ala Tyr Met Gln Leu Ser Ser Leu Thr Ser Glu Asp Ser Ala Val
            100                 105                 110

Tyr Phe Cys Ala Arg Asp Gly Cys Tyr Gly Phe Ala Tyr Trp Gly Gln
        115                 120                 125

Gly Thr Leu Val Thr Val Ser
    130                 135

<210> SEQ ID NO 6
<211> LENGTH: 393
<212> TYPE: DNA
<213> ORGANISM: Artificial Sequence
<220> FEATURE:
<223> OTHER INFORMATION: Synthesized

<400> SEQUENCE: 6

```
atggagacag acacactcct gttatgggtg ctgctgctct ggttccagg ctccactggt    60 gacattgtgc tgacccaatc tccagcttct ttggctgtgt ctctagggca gagggccacc   120
atctcctgca aggccagcca aagtgttgat tatgatggtg atagttatat gaactggtac   180
caacagaaac aggacagcc acccaaattc ctcatctgtg ctgcatccaa tctagaatct    240
gggatcccag ccaggtttag tggcagtggg tctgggacag acttcaccct caacatccat   300
cctgtggagg aggaggatgc tgcaacctat tactgtcagc aaagtaatga ggatccattc   360
acgttcggct cggggacaaa gttggaaata aaa                                393
```

<210> SEQ ID NO 7
<211> LENGTH: 131
<212> TYPE: PRT
<213> ORGANISM: Artificial Sequence
<220> FEATURE:
<223> OTHER INFORMATION: Synthesized

<400> SEQUENCE: 7

Met Glu Thr Asp Thr Leu Leu Leu Trp Val Leu Leu Leu Trp Val Pro
1               5                   10                  15

```
Gly Ser Thr Gly Asp Ile Val Leu Thr Gln Ser Pro Ala Ser Leu Ala
                20                  25                  30

Val Ser Leu Gly Gln Arg Ala Thr Ile Ser Cys Lys Ala Ser Gln Ser
            35                  40                  45

Val Asp Tyr Asp Gly Asp Ser Tyr Met Asn Trp Tyr Gln Gln Lys Pro
        50                  55                  60

Gly Gln Pro Pro Lys Phe Leu Ile Cys Ala Ala Ser Asn Leu Glu Ser
65                  70                  75                  80

Gly Ile Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110

Gln Gln Ser Asn Glu Asp Pro Phe Thr Phe Gly Ser Gly Thr Lys Leu
        115                 120                 125

Glu Ile Lys
        130
```

<210> SEQ ID NO 8
<211> LENGTH: 345
<212> TYPE: DNA
<213> ORGANISM: Artificial Sequence
<220> FEATURE:
<223> OTHER INFORMATION: Synthesized

<400> SEQUENCE: 8

```
gtccagctgc agcagtctgg acctgagctg gtgaagcctg ggacttcagt gaagatatcc      60
tgcaaggctt ctggctacag cttcacaagc tactatatac actgggtgaa gcagagtcct     120
ggacagggac ttgagtggat tggatggatt tatcctggaa gtggtaatac taagtacagt     180
gagaagttca aggcaaggc cacactgact gcagacacat cctccagcac agcctacatg      240
cagctcagca gcctgacatc tgaggactct gcagtctatt tctgtgcaag agatggttgc     300
tacgggtttg cttactgggg ccaagggact ctggtcactg tctct                     345
```

<210> SEQ ID NO 9
<211> LENGTH: 115
<212> TYPE: PRT
<213> ORGANISM: Artificial Sequence
<220> FEATURE:
<223> OTHER INFORMATION: Synthesized

<400> SEQUENCE: 9

```
Val Gln Leu Gln Gln Ser Gly Pro Glu Leu Val Lys Pro Gly Thr Ser
1               5                   10                  15

Val Lys Ile Ser Cys Lys Ala Ser Gly Tyr Ser Phe Thr Ser Tyr Tyr
                20                  25                  30

Ile His Trp Val Lys Gln Ser Pro Gly Gln Gly Leu Glu Trp Ile Gly
            35                  40                  45

Trp Ile Tyr Pro Gly Ser Gly Asn Thr Lys Tyr Ser Glu Lys Phe Lys
        50                  55                  60

Gly Lys Ala Thr Leu Thr Ala Asp Thr Ser Ser Ser Thr Ala Tyr Met
65                  70                  75                  80

Gln Leu Ser Ser Leu Thr Ser Glu Asp Ser Ala Val Tyr Phe Cys Ala
                85                  90                  95

Arg Asp Gly Cys Tyr Gly Phe Ala Tyr Trp Gly Gln Gly Thr Leu Val
            100                 105                 110

Thr Val Ser
        115
```

<210> SEQ ID NO 10
<211> LENGTH: 333
<212> TYPE: DNA
<213> ORGANISM: Artificial Sequence
<220> FEATURE:
<223> OTHER INFORMATION: Synthesized

<400> SEQUENCE: 10

```
gacattgtgc tgacccaatc tccagcttct ttggctgtgt ctctagggca gagggccacc    60
atctcctgca aggccagcca agtgttgat tatgatggtg atagttatat gaactggtac   120
caacagaaac caggacagcc acccaaattc ctcatctgtg ctgcatccaa tctagaatct   180
gggatcccag ccaggtttag tggcagtggg tctgggacag acttcaccct caacatccat   240
cctgtggagg aggaggatgc tgcaacctat tactgtcagc aaagtaatga ggatccattc   300
acgttcggct cggggacaaa gttggaaata aaa                                333
```

<210> SEQ ID NO 11
<211> LENGTH: 111
<212> TYPE: PRT
<213> ORGANISM: Artificial Sequence
<220> FEATURE:
<223> OTHER INFORMATION: Synthesized

<400> SEQUENCE: 11

```
Asp Ile Val Leu Thr Gln Ser Pro Ala Ser Leu Ala Val Ser Leu Gly
1               5                   10                  15
Gln Arg Ala Thr Ile Ser Cys Lys Ala Ser Gln Ser Val Asp Tyr Asp
            20                  25                  30
Gly Asp Ser Tyr Met Asn Trp Tyr Gln Gln Lys Pro Gly Gln Pro Pro
        35                  40                  45
Lys Phe Leu Ile Cys Ala Ala Ser Asn Leu Glu Ser Gly Ile Pro Ala
    50                  55                  60
Arg Phe Ser Gly Ser Gly Ser Gly Thr Asp Phe Thr Leu Asn Ile His
65                  70                  75                  80
Pro Val Glu Glu Glu Asp Ala Ala Thr Tyr Tyr Cys Gln Gln Ser Asn
                85                  90                  95
Glu Asp Pro Phe Thr Phe Gly Ser Gly Thr Lys Leu Glu Ile Lys
            100                 105                 110
```

<210> SEQ ID NO 12
<211> LENGTH: 5
<212> TYPE: PRT
<213> ORGANISM: Artificial Sequence
<220> FEATURE:
<223> OTHER INFORMATION: Synthesized

<400> SEQUENCE: 12

```
Ser Tyr Tyr Ile His
1               5
```

<210> SEQ ID NO 13
<211> LENGTH: 17
<212> TYPE: PRT
<213> ORGANISM: Artificial Sequence
<220> FEATURE:
<223> OTHER INFORMATION: Synthesized

<400> SEQUENCE: 13

```
Trp Ile Tyr Pro Gly Ser Gly Asn Thr Lys Tyr Ser Glu Lys Phe Lys
1               5                   10                  15
```

Gly

<210> SEQ ID NO 14
<211> LENGTH: 8
<212> TYPE: PRT
<213> ORGANISM: Artificial Sequence
<220> FEATURE:
<223> OTHER INFORMATION: Synthesized

<400> SEQUENCE: 14

Asp Gly Cys Tyr Gly Phe Ala Tyr
1               5

<210> SEQ ID NO 15
<211> LENGTH: 15
<212> TYPE: PRT
<213> ORGANISM: Artificial Sequence
<220> FEATURE:
<223> OTHER INFORMATION: Synthesized

<400> SEQUENCE: 15

Lys Ala Ser Gln Ser Val Asp Tyr Asp Gly Asp Ser Tyr Met Asn
1               5                   10                  15

<210> SEQ ID NO 16
<211> LENGTH: 7
<212> TYPE: PRT
<213> ORGANISM: Artificial Sequence
<220> FEATURE:
<223> OTHER INFORMATION: Synthesized

<400> SEQUENCE: 16

Ala Ala Ser Asn Leu Glu Ser
1               5

<210> SEQ ID NO 17
<211> LENGTH: 9
<212> TYPE: PRT
<213> ORGANISM: Artificial Sequence
<220> FEATURE:
<223> OTHER INFORMATION: Synthesized

<400> SEQUENCE: 17

Gln Gln Ser Asn Glu Asp Pro Phe Thr
1               5

<210> SEQ ID NO 18
<211> LENGTH: 351
<212> TYPE: DNA
<213> ORGANISM: Artificial Sequence
<220> FEATURE:
<223> OTHER INFORMATION: Synthesized

<400> SEQUENCE: 18
caggtgcagc tggtgcagtc cggcgccgag ctgaagaagc cggcgcctc cgtgaaggtg      60 tcctgcaagg cctccggcta ctccttcacc tcctactaca tccactgggt gaagcaggcc    120
cccggccagg gcctggagtg gatcggctgg atctacccccg gctccggcaa caccaagtac   180
tccgagaagt tcaagggccg cgccaccctg accgccgaca cctccacctc caccgcctac   240
atggagctgc gctccctgcg ctccgacgac accgccgtgt acttctgcgc ccgcgacggc   300
tgctacggct cgcctactg gggccagggc accctggtga ccgtgtcctc a              351

<210> SEQ ID NO 19

```
<211> LENGTH: 117
<212> TYPE: PRT
<213> ORGANISM: Artificial Sequence
<220> FEATURE:
<223> OTHER INFORMATION: Synthesized

<400> SEQUENCE: 19

Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Ser Phe Thr Ser Tyr
                20                  25                  30

Tyr Ile His Trp Val Lys Gln Ala Pro Gly Gln Gly Leu Glu Trp Ile
            35                  40                  45

Gly Trp Ile Tyr Pro Gly Ser Gly Asn Thr Lys Tyr Ser Glu Lys Phe
    50                  55                  60

Lys Gly Arg Ala Thr Leu Thr Ala Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Gly Cys Tyr Gly Phe Ala Tyr Trp Gly Gln Gly Thr Leu
            100                 105                 110

Val Thr Val Ser Ser
        115

<210> SEQ ID NO 20
<211> LENGTH: 351
<212> TYPE: DNA
<213> ORGANISM: Artificial Sequence
<220> FEATURE:
<223> OTHER INFORMATION: Synthesized

<400> SEQUENCE: 20
caggtgcagc tggtgcagtc cggcgccgag gtgaagaagc ccggcgcctc cgtgaaggtg      60
tcctgcaagg cctccggcta ctccttcacc tcctactaca tccactgggt cgcgcaggcc    120
cccggccagg gcctggagtg gatcggctgg atctaccccg gctccggcaa caccaagtac    180
tccgagaagt tcaagggccg cgccaccctg accgccgaca cctccacctc caccgcctac    240
atggagctgc gctccctgcg ctccgacgac accgccgtgt acttctgcgc ccgcgacggc    300
tgctacggct tcgcctactg gggccagggc accctggtga ccgtgtcctc a             351

<210> SEQ ID NO 21
<211> LENGTH: 117
<212> TYPE: PRT
<213> ORGANISM: Artificial Sequence
<220> FEATURE:
<223> OTHER INFORMATION: Synthesized

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
                20                  25                  30

Tyr Ile His Trp Val Arg Gln Ala Pro Gly Gln Gly Leu Glu Trp Ile
            35                  40                  45

Gly Trp Ile Tyr Pro Gly Ser Gly Asn Thr Lys Tyr Ser Glu Lys Phe
    50                  55                  60

Lys Gly Arg Ala Thr Leu Thr Ala Asp Thr Ser Thr Ser Thr Ala Tyr
65                  70                  75                  80
```

```
Met Glu Leu Arg Ser Leu Arg Ser Asp Asp Thr Ala Val Tyr Phe Cys
                85                  90                  95

Ala Arg Asp Gly Cys Tyr Gly Phe Ala Tyr Trp Gly Gln Gly Thr Leu
            100                 105                 110

Val Thr Val Ser Ser
        115

<210> SEQ ID NO 22
<211> LENGTH: 351
<212> TYPE: DNA
<213> ORGANISM: Artificial Sequence
<220> FEATURE:
<223> OTHER INFORMATION: Synthesized

<400> SEQUENCE: 22
caggtgcagc tggtgcagtc cggcgccgag gtgaagaagc ccggcgcctc cgtgaaggtg    60
tcctgcaagg cctccggcta caccttcacc tcctactaca tccactgggt gcgccaggcc   120
cccggccagg gcctggagtg gatgggctgg atctaccccg gctccggcaa caccaagtac   180
tccgagaagt tcaagggccg cgccaccatg accgccgaca cctccacctc caccgcctac   240
atggagctgc gctccctgcg ctccgacgac accgccgtgt actactgcgc ccgcgacggc   300
tgctacggct cgcctactg gggccagggc accctggtga ccgtgtcctc a             351

<210> SEQ ID NO 23
<211> LENGTH: 117
<212> TYPE: PRT
<213> ORGANISM: Artificial Sequence
<220> FEATURE:
<223> OTHER INFORMATION: Synthesized

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Tyr Pro Gly Ser Gly Asn Thr Lys Tyr Ser Glu Lys Phe
    50                  55                  60

Lys Gly Arg Ala Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Cys Tyr Gly Phe Ala Tyr Trp Gly Gln Gly Thr Leu
            100                 105                 110

Val Thr Val Ser Ser
        115

<210> SEQ ID NO 24
<211> LENGTH: 351
<212> TYPE: DNA
<213> ORGANISM: Artificial Sequence
<220> FEATURE:
<223> OTHER INFORMATION: Synthesized

<400> SEQUENCE: 24
caggtgcagc tggtgcagtc cggcgccgag gtgaagaagc ccggcgcctc cgtgaaggtg    60
tcctgcaagg cctccggcta ctccttcacc tcctactaca tccactgggt gcgccaggcc   120
```

```
cccggccagg gcctggagtg gatcggctgg atctacccccg gctccggcaa caccaagtac    180
tccgagaagt tcaagggccg cgccaccctg accgccgaca cctccacctc caccgcctac    240
atggagctgc gctccctgcg ctccgacgac accgccgtgt acttctgcgc ccgcgacggc    300
tcctacggct cgcctactg gggccagggc accctggtga ccgtgtcctc a              351
```

```
<210> SEQ ID NO 25
<211> LENGTH: 117
<212> TYPE: PRT
<213> ORGANISM: Artificial Sequence
<220> FEATURE:
<223> OTHER INFORMATION: Synthesized

<400> SEQUENCE: 25
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Tyr Ile His Trp Val Arg Gln Ala Pro Gly Gln Gly Leu Glu Trp Ile
        35                  40                  45

Gly Trp Ile Tyr Pro Gly Ser Gly Asn Thr Lys Tyr Ser Glu Lys Phe
    50                  55                  60

Lys Gly Arg Ala Thr Leu Thr Ala Asp Thr Ser Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Gly Ser Tyr Gly Phe Ala Tyr Trp Gly Gln Gly Thr Leu
            100                 105                 110

Val Thr Val Ser Ser
        115
```

```
<210> SEQ ID NO 26
<211> LENGTH: 351
<212> TYPE: DNA
<213> ORGANISM: Artificial Sequence
<220> FEATURE:
<223> OTHER INFORMATION: Synthesized

<400> SEQUENCE: 26
```

```
caggtgcagc tggtgcagtc cggcgccgag gtgaagaagc ccggcgcctc cgtgaaggtg    60
tcctgcaagg cctccggcta caccttcacc tcctactaca tccactgggt gcgccaggcc    120
cccggccagg gcctggagtg gatgggctgg atctaccccg gctccggcaa caccaagtac    180
tccgagaagt tcaagggccg cgccaccatg accgccgaca cctccacctc caccgcctac    240
atggagctgc gctccctgcg ctccgacgac accgccgtgt actactgcgc ccgcgacggc    300
tcctacggct cgcctactg gggccagggc accctggtga ccgtgtcctc a              351
```

```
<210> SEQ ID NO 27
<211> LENGTH: 117
<212> TYPE: PRT
<213> ORGANISM: Artificial Sequence
<220> FEATURE:
<223> OTHER INFORMATION: Synthesized

<400> SEQUENCE: 27
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

Tyr Ile His Trp Val Arg Gln Ala Pro Gly Gln Gly Leu Glu Trp Met
        35                  40                  45

Gly Trp Ile Tyr Pro Gly Ser Gly Asn Thr Lys Tyr Ser Glu Lys Phe
    50                  55                  60

Lys Gly Arg Ala Thr Met Thr Ala Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Asp Gly Ser Tyr Gly Phe Ala Tyr Trp Gly Gln Gly Thr Leu
            100                 105                 110

Val Thr Val Ser Ser
        115

<210> SEQ ID NO 28
<211> LENGTH: 57
<212> TYPE: DNA
<213> ORGANISM: Artificial Sequence
<220> FEATURE:
<223> OTHER INFORMATION: Synthesized

<400> SEQUENCE: 28
atggagttcg gcctgtcctg gctgttcctg gtggccatcc tgaagggcgt gcagtgc     57

<210> SEQ ID NO 29
<211> LENGTH: 19
<212> TYPE: PRT
<213> ORGANISM: Artificial Sequence
<220> FEATURE:
<223> OTHER INFORMATION: Synthesized

<400> SEQUENCE: 29

Met Glu Phe Gly Leu Ser Trp Leu Phe Leu Val Ala Ile Leu Lys Gly
1               5                   10                  15

Val Gln Cys

<210> SEQ ID NO 30
<211> LENGTH: 57
<212> TYPE: DNA
<213> ORGANISM: Artificial Sequence
<220> FEATURE:
<223> OTHER INFORMATION: Synthesized

<400> SEQUENCE: 30
atggactgga cctggagcat ccttttcttg gtggcagcag caacaggtgc ccactcc     57

<210> SEQ ID NO 31
<211> LENGTH: 19
<212> TYPE: PRT
<213> ORGANISM: Artificial Sequence
<220> FEATURE:
<223> OTHER INFORMATION: Synthesized

<400> SEQUENCE: 31

Met Asp Trp Thr Trp Ser Ile Leu Phe Leu Val Ala Ala Ala Thr Gly
1               5                   10                  15

Ala His Ser

<210> SEQ ID NO 32
<211> LENGTH: 333
<212> TYPE: DNA
<213> ORGANISM: Artificial Sequence
<220> FEATURE:

<223> OTHER INFORMATION: Synthesized

<400> SEQUENCE: 32

```
gacatccagc tgacccagtc cccctcctcc ctgtccgcct ccgtgggcga ccgcgtgacc    60
atcacctgca aggcctccca gtccgtggac tacgacggcg actcctacat gaactggtac   120
cagcagaagc ccggcaaggc ccccaagttc ctgatctgcg ccgcctccaa cctggagtcc   180
ggcgtgccct cccgcttctc cggctccggc tccggcaccg acttcaccct gaccatctcc   240
tccctgcagc ccgaggacgc cgccacctac tactgccagc agtccaacga ggaccccttc   300
accttcggcc agggcaccaa gctggagatc aag                                333
```

<210> SEQ ID NO 33
<211> LENGTH: 111
<212> TYPE: PRT
<213> ORGANISM: Artificial Sequence
<220> FEATURE:
<223> OTHER INFORMATION: Synthesized

<400> SEQUENCE: 33

```
Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Phe Leu Ile Cys Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Ala Ala Thr Tyr Tyr Cys Gln Gln Ser Asn
                85                  90                  95

Glu Asp Pro Phe Thr Phe Gly Gln Gly Thr Lys Leu Glu Ile Lys
            100                 105                 110
```

<210> SEQ ID NO 34
<211> LENGTH: 333
<212> TYPE: DNA
<213> ORGANISM: Artificial Sequence
<220> FEATURE:
<223> OTHER INFORMATION: Synthesized

<400> SEQUENCE: 34

```
gacatccagc tgacccagtc cccctcctcc ctgtccgcct ccgtgggcga ccgcgtgacc    60
atcacctgca aggcctccca gtccgtggac tacgacggcg actcctacat gaactggtac   120
cagcagaagc ccggcaaggc ccccaagttc ctgatctacg ccgcctccaa cctggagtcc   180
ggcgtgccct cccgcttctc cggctccggc tccggcaccg acttcaccct gaccatctcc   240
tccctgcagc ccgaggacgc cgccacctac tactgccagc agtccaacga ggaccccttc   300
accttcggcc agggcaccaa gctggagatc aag                                333
```

<210> SEQ ID NO 35
<211> LENGTH: 111
<212> TYPE: PRT
<213> ORGANISM: Artificial Sequence
<220> FEATURE:
<223> OTHER INFORMATION: Synthesized

<400> SEQUENCE: 35

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Tyr Met Asn Trp Tyr Gln Gln Lys Pro Gly Lys Ala Pro
            35                  40                  45

Lys Phe Leu Ile Tyr Ala Ala Ser Asn Leu Glu Ser Gly Val Pro Ser
        50                  55                  60

Arg Phe Ser Gly Ser Gly Ser Gly Thr Asp Phe Thr Leu Thr Ile Ser
65                  70                  75                  80

Ser Leu Gln Pro Glu Asp Ala Ala Thr Tyr Tyr Cys Gln Gln Ser Asn
                85                  90                  95

Glu Asp Pro Phe Thr Phe Gly Gln Gly Thr Lys Leu Glu Ile Lys
            100                 105                 110

<210> SEQ ID NO 36
<211> LENGTH: 333
<212> TYPE: DNA
<213> ORGANISM: Artificial Sequence
<220> FEATURE:
<223> OTHER INFORMATION: Synthesized

<400> SEQUENCE: 36
gacatccagc tgacccagtc cccctcctcc ctgtccgcct ccgtgggcga ccgcgtgacc      60
atcacctgca aggcctccca gtccgtggac tacgacggcg actcctacat gaactggtac     120
cagcagaagc ccggcaaggc ccccaagttc ctgatctgcg ccgcctccaa cctggagtcc     180
ggcgtgccct cccgcttctc cggctccggc tccggcaccg acttcaccct gaccatctcc     240
tccctgcagc ccgaggactt cgccacctac tactgccagc agtccaacga ggacccct tc     300 accttcggcc agggcaccaa gctggagatc aag                                  333

<210> SEQ ID NO 37
<211> LENGTH: 111
<212> TYPE: PRT
<213> ORGANISM: Artificial Sequence
<220> FEATURE:
<223> OTHER INFORMATION: Synthesized

<400> SEQUENCE: 37

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Tyr Met Asn Trp Tyr Gln Gln Lys Pro Gly Lys Ala Pro
            35                  40                  45

Lys Phe Leu Ile Cys Ala Ala Ser Asn Leu Glu Ser Gly Val Pro Ser
        50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Phe Thr Phe Gly Gln Gly Thr Lys Leu Glu Ile Lys
            100                 105                 110

<210> SEQ ID NO 38
<211> LENGTH: 333
<212> TYPE: DNA
<213> ORGANISM: Artificial Sequence
<220> FEATURE:
<223> OTHER INFORMATION: Synthesized

<400> SEQUENCE: 38

```
gacatccagc tgacccagtc cccctcctcc ctgtccgcct ccgtgggcga ccgcgtgacc    60
atcacctgca aggcctccca gtccgtggac tacgacggcg actcctacat gaactggtac   120
cagcagaagc ccggcaaggc ccccaagttc ctgatctacg ccgcctccaa cctggagtcc   180
ggcgtgccct cccgcttctc cggctccggc tccggcaccg acttcaccct gaccatctcc   240
tccctgcagc ccgaggactt cgccacctac tactgccagc agtccaacga ggacccttc    300
accttcggcc agggcaccaa gctggagatc aag                                333
```

<210> SEQ ID NO 39
<211> LENGTH: 111
<212> TYPE: PRT
<213> ORGANISM: Artificial Sequence
<220> FEATURE:
<223> OTHER INFORMATION: Synthesized

<400> SEQUENCE: 39

```
Asp Ile Gln Leu Thr Gln Ser Pro Ser Ser Leu Ser Ala Ser Val Gly
1               5                   10                  15
Asp Arg Val Thr Ile Thr Cys Lys Ala Ser Gln Ser Val Asp Tyr Asp
            20                  25                  30
Gly Asp Ser Tyr Met Asn Trp Tyr Gln Gln Lys Pro Gly Lys Ala Pro
        35                  40                  45
Lys Phe Leu Ile Tyr Ala Ala Ser Asn Leu Glu Ser Gly Val Pro Ser
    50                  55                  60
Arg Phe Ser Gly Ser Gly Ser Gly Thr Asp Phe Thr Leu Thr Ile Ser
65                  70                  75                  80
Ser Leu Gln Pro Glu Asp Phe Ala Thr Tyr Tyr Cys Gln Gln Ser Asn
                85                  90                  95
Glu Asp Pro Phe Thr Phe Gly Gln Gly Thr Lys Leu Glu Ile Lys
            100                 105                 110
```

<210> SEQ ID NO 40
<211> LENGTH: 66
<212> TYPE: DNA
<213> ORGANISM: Artificial Sequence
<220> FEATURE:
<223> OTHER INFORMATION: Synthesized

<400> SEQUENCE: 40

```
atggacatgc gcgtgcccgc ccagctgctg ggcctgctga tgctgtgggt gtccggctcc    60
tccggc                                                              66
```

<210> SEQ ID NO 41
<211> LENGTH: 22
<212> TYPE: PRT
<213> ORGANISM: Artificial Sequence
<220> FEATURE:
<223> OTHER INFORMATION: Synthesized

<400> SEQUENCE: 41

```
Met Asp Met Arg Val Pro Ala Gln Leu Leu Gly Leu Leu Met Leu Trp
1               5                   10                  15
Val Ser Gly Ser Ser Gly
            20
```

-continued

```
<210> SEQ ID NO 42
<211> LENGTH: 117
<212> TYPE: PRT
<213> ORGANISM: Artificial Sequence
<220> FEATURE:
<223> OTHER INFORMATION: Synthesized

<400> SEQUENCE: 42
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Gly Ile Ser Trp Val Arg Gln Ala Pro Gly Gln Gly Leu Glu Trp Met
        35                  40                  45

Gly Trp Ile Ser Pro Tyr Asn Gly Asp Thr Asn Tyr Ala Gln Asn Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Gly Ser Met Ser Asp Tyr Trp Gly Gln Gly Thr Leu
            100                 105                 110

Val Thr Val Ser Ser
        115

```
<210> SEQ ID NO 43
<211> LENGTH: 107
<212> TYPE: PRT
<213> ORGANISM: Artificial Sequence
<220> FEATURE:
<223> OTHER INFORMATION: Synthesized

<400> SEQUENCE: 43
```

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Pro
                85                  90                  95

Thr Phe Gly Gln Gly Thr Lys Leu Glu Ile Lys
            100                 105

```
<210> SEQ ID NO 44
<211> LENGTH: 117
<212> TYPE: PRT
<213> ORGANISM: Artificial Sequence
<220> FEATURE:
<223> OTHER INFORMATION: Synthesized

<400> SEQUENCE: 44
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Tyr Ile His Trp Val Arg Gln Ala Pro Gly Gln Gly Leu Glu Trp Met
            35                  40                  45

Gly Trp Ile Tyr Pro Gly Ser Gly Asn Thr Lys Tyr Ser Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Cys Tyr Gly Phe Ala Tyr Trp Gly Gln Gly Thr Leu
            100                 105                 110

Val Thr Val Ser Ser
        115

<210> SEQ ID NO 45
<211> LENGTH: 111
<212> TYPE: PRT
<213> ORGANISM: Artificial Sequence
<220> FEATURE:
<223> OTHER INFORMATION: Synthesized

<400> SEQUENCE: 45

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Phe Thr Phe Gly Gln Gly Thr Lys Leu Glu Ile Lys
            100                 105                 110

<210> SEQ ID NO 46
<211> LENGTH: 117
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 11
<223> OTHER INFORMATION: Xaa is Val or Leu
<220> FEATURE:
<221> NAME/KEY: VARIANT
<222> LOCATION: 28
<223> OTHER INFORMATION: Xaa is Ser or Thr
<220> FEATURE:
<221> NAME/KEY: VARIANT
<222> LOCATION: 38
<223> OTHER INFORMATION: Xaa is Arg or Lys
<220> FEATURE:
<221> NAME/KEY: VARIANT
<222> LOCATION: 48
<223> OTHER INFORMATION: Xaa is Met or Ile
<220> FEATURE:
<221> NAME/KEY: VARIANT
<222> LOCATION: 68
<223> OTHER INFORMATION: Xaa is Val or Ala
<220> FEATURE:
<221> NAME/KEY: VARIANT
<222> LOCATION: 70
<223> OTHER INFORMATION: Xaa is Met or Leu
<220> FEATURE:
<221> NAME/KEY: VARIANT
<222> LOCATION: 72
<223> OTHER INFORMATION: Xaa is Thr or Ala
<220> FEATURE:
<221> NAME/KEY: VARIANT
<222> LOCATION: 95
<223> OTHER INFORMATION: Xaa is Tyr or Phe
<220> FEATURE:
<221> NAME/KEY: VARIANT
<222> LOCATION: 101
<223> OTHER INFORMATION: Xaa is Cys or Ser

<400> SEQUENCE: 46

Gln Val Gln Leu Val Gln Ser Gly Ala Glu Xaa Lys Lys Pro Gly Ala
1               5                   10                  15

Ser Val Lys Val Ser Cys Lys Ala Ser Gly Tyr Xaa Phe Thr Ser Tyr
            20                  25                  30

Tyr Ile His Trp Val Xaa Gln Ala Pro Gly Gln Gly Leu Glu Trp Xaa
        35                  40                  45

Gly Trp Ile Tyr Pro Gly Ser Gly Asn Thr Lys Tyr Ser Glu Lys Phe
    50                  55                  60

Lys Gly Arg Xaa Thr Xaa Thr Xaa Asp Thr Ser Ser Thr Ala Tyr
65                  70                  75                  80

Met Glu Leu Arg Ser Leu Arg Ser Asp Asp Thr Ala Val Tyr Xaa Cys
            85                  90                  95

Ala Arg Asp Gly Xaa Tyr Gly Phe Ala Tyr Trp Gly Gln Gly Thr Leu
            100                 105                 110

Val Thr Val Ser Ser
            115

<210> SEQ ID NO 47
<211> LENGTH: 111
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 50
<223> OTHER INFORMATION: Xaa is Leu or Phe
<220> FEATURE:
<221> NAME/KEY: VARIANT
<222> LOCATION: 53
<223> OTHER INFORMATION: Xaa is Tyr or Cys
<220> FEATURE:
<221> NAME/KEY: VARIANT
<222> LOCATION: 87
<223> OTHER INFORMATION: Xaa is Phe or Ala

<400> SEQUENCE: 47

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Xaa Leu Ile Xaa Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Xaa Ala Thr Tyr Tyr Cys Gln Gln Ser Asn

```
                            85                  90                  95

Glu Asp Pro Phe Thr Phe Gly Gln Gly Thr Lys Leu Glu Ile Lys
                100                 105                 110

<210> SEQ ID NO 48
<211> LENGTH: 8
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 3
<223> OTHER INFORMATION: Xaa is Cys or Met or Ser or Thr

<400> SEQUENCE: 48

Asp Gly Xaa Tyr Gly Phe Ala Tyr
1               5

<210> SEQ ID NO 49
<211> LENGTH: 107
<212> TYPE: PRT
<213> ORGANISM: Artificial Sequence
<220> FEATURE:
<223> OTHER INFORMATION: Synthesized

<400> SEQUENCE: 49

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 50
<211> LENGTH: 330
<212> TYPE: PRT
<213> ORGANISM: Artificial Sequence
<220> FEATURE:
<223> OTHER INFORMATION: Synthesized

<400> SEQUENCE: 50

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
```

```
            85                  90                  95
Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Val Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 51
<211> LENGTH: 106
<212> TYPE: PRT
<213> ORGANISM: Artificial Sequence
<220> FEATURE:
<223> OTHER INFORMATION: Synthesized

<400> SEQUENCE: 51

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

```
<210> SEQ ID NO 52
<211> LENGTH: 330
<212> TYPE: PRT
<213> ORGANISM: Artificial Sequence
<220> FEATURE:
<223> OTHER INFORMATION: Synthesized

<400> SEQUENCE: 52

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 53
<211> LENGTH: 218
<212> TYPE: PRT
<213> ORGANISM: Artificial Sequence
<220> FEATURE:
<223> OTHER INFORMATION: Synthesized
```

<400> SEQUENCE: 53

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Phe Leu Ile Cys Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Phe Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 54
<211> LENGTH: 217
<212> TYPE: PRT
<213> ORGANISM: Artificial Sequence
<220> FEATURE:
<223> OTHER INFORMATION: Synthesized

<400> SEQUENCE: 54

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Phe Leu Ile Cys Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Phe Thr Phe Gly Gln Gly Thr Lys Leu Glu Ile Lys Thr
            100                 105                 110

Val Ala Ala Pro Ser Val Phe Ile Phe Pro Pro Ser Asp Glu Gln Leu
        115                 120                 125

```
Lys Ser Gly Thr Ala Ser Val Val Cys Leu Leu Asn Asn Phe Tyr Pro
            130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
                180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
210                 215

<210> SEQ ID NO 55
<211> LENGTH: 447
<212> TYPE: PRT
<213> ORGANISM: Artificial Sequence
<220> FEATURE:
<223> OTHER INFORMATION: Synthesized

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Tyr Pro Gly Ser Gly Asn Thr Lys Tyr Ser Glu Lys Phe
    50                  55                  60

Lys Gly Arg Ala Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Cys Tyr Gly Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270
```

Val Lys Phe Asn Trp Tyr Val Asp Gly Val Glu Val His Asn Val Lys
275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 56
<211> LENGTH: 447
<212> TYPE: PRT
<213> ORGANISM: Artificial Sequence
<220> FEATURE:
<223> OTHER INFORMATION: Synthesized

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Ile His Trp Val Arg Gln Ala Pro Gly Gln Gly Leu Glu Trp Met
                35                  40                  45

Gly Trp Ile Tyr Pro Gly Ser Gly Asn Thr Lys Tyr Ser Glu Lys Phe
50                  55                  60

Lys Gly Arg Ala Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Cys Tyr Gly Phe Ala Tyr Trp Gly Gln Gly Thr Leu
                100                 105                 110

Val Thr Val Ser Ser Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
                130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 57
<211> LENGTH: 326
<212> TYPE: PRT
<213> ORGANISM: Artificial Sequence
<220> FEATURE:
<223> OTHER INFORMATION: Synthesized

<400> SEQUENCE: 57

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
            165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 58
<211> LENGTH: 330
<212> TYPE: PRT
<213> ORGANISM: Artificial Sequence
<220> FEATURE:
<223> OTHER INFORMATION: Synthesized

<400> SEQUENCE: 58

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330
```

HUMANIZED ANTIBODIES THAT RECOGNIZE ALPHA-SYNUCLEIN

CROSS-REFERENCE TO RELATED APPLICATION

This application is a continuation of U.S. patent application Ser. No. 16/144,923 filed Sep. 27, 2018, which is a continuation of U.S. patent application Ser. No. 15/587,255 filed May 4, 2017, which is a continuation of U.S. patent application Ser. No. 14/937,792 filed Nov. 10, 2015, which is a continuation of U.S. patent application Ser. No. 14/340,355 filed Jul. 24, 204, which is a continuation of U.S. patent application Ser. No. 13/750,983 filed Jan. 25, 2013, which claims priority to U.S. Provisional Patent Application No. 61/591,835, filed Jan. 27, 2012 and U.S. Provisional Patent Application No. 61/711,207, filed Oct. 8, 2012, which are incorporated by reference in their entirety for all purposes.

REFERENCE TO A SEQUENCE LISTING

This application includes an electronic sequence listing in a file named 542953SEQLST.TXT, created on Feb. 18, 2020 and containing 57,483 bytes, which is hereby incorporated by reference in its entirety for all purposes.

BACKGROUND

Synucleinopathies, including Lewy body diseases (LBDs) are characterized by degeneration of the dopaminergic system, motor alterations, cognitive impairment, and formation of Lewy bodies (LBs) and/or Lewy neurites. (McKeith et al., Neurology (1996) 47:1113-24). Synucleinopathies include Parkinson's disease (including idiopathic Parkinson's disease), Diffuse Lewy Body Disease (DLBD) also known as Dementia with Lewy Bodies (DLB), Lewy body variant of Alzheimer's disease (LBV), Combined Alzheimer's and Parkinson disease, pure autonomic failure and multiple system atrophy (MSA; e.g., Olivopontocerebellar Atrophy, Striatonigral Degeneration and Shy-Drager Syndrome). Several nonmotor signs and symptoms are thought to be harbingers for synucleinopathies in the prodromal phase of the diseases (i.e., the presymptomatic, subclinical, preclinical, or premotor period). Such early signs include, for example, REM sleep behavior disorder (RBD), loss of smell and constipation (Mahowald et al., Neurology (2010) 75:488-489). Lewy body diseases continue to be a common cause for movement disorders and cognitive deterioration in the aging population (Galasko et al., Arch. Neurol. (1994) 51:888-95).

Alpha-synuclein is part of a large family of proteins including beta- and gamma-synuclein and synoretin. Alpha-synuclein is expressed in the normal state associated with synapses and is believed to play a role in neural plasticity, learning and memory. Several studies have implicated alpha-synuclein with a central role in PD pathogenesis. The protein can aggregate to form insoluble fibrils in pathological conditions. For example, synuclein accumulates in LBs (Spillantini et al., Nature (1997) 388:839-40; Takeda et al., J. Pathol. (1998) 152:367-72; Wakabayashi et al., Neurosci. Lett. (1997) 239:45-8). Mutations in the alpha-synuclein gene co-segregate with rare familial forms of parkinsonism (Kruger et al., Nature Gen. (1998) 18:106-8; Polymeropoulos, et al., Science (1997) 276:2045-7). Over expression of alpha synuclein in transgenic mice (Masliah et al., Science (2000) 287:1265-9) and *Drosophila* (Feany et al., Nature (2000) 404:394-8) mimics several pathological aspects of Lewy body disease. In addition, it has been suggested that soluble oligomers of synuclein may be neurotoxic (Conway et al., Proc. Natl. Acad. Sci. USA (2000) 97:571-576; Volles et al., J. Biochemistry (2003) 42:7871-7878). The accumulation of alpha-synuclein with similar morphological and neurological alterations in species and animal models as diverse as humans, mice, and flies suggests that this molecule contributes to the development of Lewy body disease.

SUMMARY OF THE CLAIMED INVENTION

The invention provides antibodies comprising a mature heavy chain variable region comprising the three Kabat CDRs of SEQ ID NO:44, and being at least 90% identical to SEQ ID NO:44, and a light chain comprising the three Kabat CDRs of SEQ ID NO:45, and being at least 90% identical to SEQ ID NO:45. In some antibodies, the mature heavy chain variable region is at least 95%, 96%, 97%, 98%, or 99% identical to SEQ ID NO:44 and mature light chain variable region is at least 95%, 96%, 97%, 98%, or 99% identical to SEQ ID NO:45. In some antibodies, position L46 (Kabat numbering) can be occupied by F; position L49 (Kabat numbering) can be occupied by C; position L83 (Kabat numbering) can be occupied by A; position H11 (Kabat numbering) can be occupied by L; position H28 (Kabat numbering) can be occupied by S; position H38 (Kabat numbering) can be occupied by K; position H48 (Kabat numbering) can be occupied by I; position H67 (Kabat numbering) can be occupied by A; position H69 (Kabat numbering) can be occupied by L; position H71 (Kabat numbering) can be occupied by A; and/or position H91 (Kabat numbering) can be occupied by F. In some of such antibodies, position H97 (Kabat numbering) can be occupied by S. In some of such antibodies the amino acid sequence of the mature heavy chain variable region is SEQ ID NO:44 and the amino acid sequence of the mature light chain variable region is SEQ ID NO:45 except provided that position L46 (Kabat numbering) can be occupied by L or F and/or position L49 (Kabat numbering) can be occupied by Y or C and/or position L83 (Kabat numbering) can be occupied by F or A, and/or position H11 (Kabat numbering) can be occupied by V or L, and/or position H28 (Kabat numbering) can be occupied by T or S, and/or position H38 (Kabat numbering) can be occupied by R or K, and/or position H48 (Kabat numbering) can be occupied by M or I, and/or position H67 (Kabat numbering) can be occupied by V or A, and/or position H69 (Kabat numbering) can be occupied by M or L, and/or position H71 (Kabat numbering) can be occupied by T or A, and/or position H91 (Kabat numbering) can be occupied by Y or F, and/or H97 (Kabat numbering) can be occupied by C or S. In some of such antibodies, position H71 (Kabat numbering) is occupied by A. In some of such antibodies, position H67 (Kabat numbering) is occupied by A, position H71 (Kabat numbering) is occupied by A. In some of such antibodies, position L46 (Kabat numbering) is occupied by F. In some of such antibodies, position L46 (Kabat numbering) is occupied by F, position L49 (Kabat numbering) is occupied by C. In some of such antibodies, position L46 (Kabat numbering) is occupied by F, position L49 (Kabat numbering) is occupied by Y. In some of such antibodies, position H67 (Kabat numbering) is occupied by A, position H71 (Kabat numbering) is occupied by A, L46 (Kabat numbering) is occupied by F, and position L49 (Kabat numbering) is occupied by C. In some of such antibodies, position H11 (Kabat numbering) is occupied by L and position H38 (Kabat numbering) is occupied by K. In some of such antibodies, position H11

(Kabat numbering) is occupied by V and position H38 (Kabat numbering) is occupied by R. In some of such antibodies, position H28 (Kabat numbering) is occupied by S, position H48 (Kabat numbering) is occupied by I, position H69 (Kabat numbering) is occupied by L, position H91 (Kabat numbering) is occupied by F. In some of such antibodies, position H28 (Kabat numbering) is occupied by T, position H48 (Kabat numbering) is occupied by M, position H69 (Kabat numbering) is occupied by M, position H91 (Kabat numbering) is occupied by Y. In some of such antibodies, position L83 (Kabat numbering) is occupied by A. In some of such antibodies, position L83 (Kabat numbering) is occupied by F. In some of such antibodies, position H97 (Kabat numbering) is occupied by S. In some of such antibodies, position H97 (Kabat numbering) is occupied by C. In some of such antibodies, position L46 (Kabat numbering) is occupied by F, position L49 (Kabat numbering) is occupied by C and position L83 (Kabat numbering) is occupied by A. In some of such antibodies, position L46 (Kabat numbering) is occupied by F, position L49 (Kabat numbering) is occupied by Y and position L83 (Kabat numbering) is occupied by A. In some of such antibodies, position L46 (Kabat numbering) is occupied by F, position L49 (Kabat numbering) is occupied by C and position L83 (Kabat numbering) is occupied by F. In some of such antibodies, position L46 (Kabat numbering) is occupied by F, position L49 (Kabat numbering) is occupied by Y and position L83 (Kabat numbering) is occupied by F. In some of such antibodies, position H11 (Kabat numbering) is occupied by L, position H28 (Kabat numbering) is occupied by S, position H38 (Kabat numbering) is occupied by K, position H48 (Kabat numbering) is occupied by I, position H67 (Kabat numbering) is occupied by A, position H69 (Kabat numbering) is occupied by L, position H71 (Kabat numbering) is occupied by A, position H91 (Kabat numbering) is occupied by F and position H97 (Kabat numbering) is occupied by C. In some of such antibodies, position H11 (Kabat numbering) is occupied by V, position H28 (Kabat numbering) is occupied by S, position H38 (Kabat numbering) is occupied by R, position H48 (Kabat numbering) is occupied by I, position H67 (Kabat numbering) is occupied by A, position H69 (Kabat numbering) is occupied by L, position H71 (Kabat numbering) is occupied by A, position H91 (Kabat numbering) is occupied by F and position H97 (Kabat numbering) is occupied by C. In some of such antibodies, position H11 (Kabat numbering) is occupied by V, position H28 (Kabat numbering) is occupied by T, position H38 (Kabat numbering) is occupied by R, position H48 (Kabat numbering) is occupied by M, position H67 (Kabat numbering) is occupied by A, position H69 (Kabat numbering) is occupied by M, position H71 (Kabat numbering) is occupied by A, position H91 (Kabat numbering) is occupied by Y and position H97 (Kabat numbering) is occupied by C. In some of such antibodies, position H11 (Kabat numbering) is occupied by V, position H28 (Kabat numbering) is occupied by S, position H38 (Kabat numbering) is occupied by R, position H48 (Kabat numbering) is occupied by I, position H67 (Kabat numbering) is occupied by A, position H69 (Kabat numbering) is occupied by L, position H71 (Kabat numbering) is occupied by A, position H91 (Kabat numbering) is occupied by F and position H97 (Kabat numbering) is occupied by S. In some of such antibodies, position H11 (Kabat numbering) is occupied by V, position H28 (Kabat numbering) is occupied by T, position H38 (Kabat numbering) is occupied by R, position H48 (Kabat numbering) is occupied by M, position H67 (Kabat numbering) is occupied by A, position H69 (Kabat numbering) is occupied by M, position H71 (Kabat numbering) is occupied by A, position H91 (Kabat numbering) is occupied by Y and position H97 (Kabat numbering) is occupied by S. In some of such antibodies the amino acid sequence of the mature heavy chain variable region is otherwise that of SEQ ID NO:44 and the amino acid sequence of the mature light chain variable region is otherwise that of SEQ ID NO:45.

The invention further provides an antibody comprising a humanized heavy chain comprising the three Kabat CDRs of SEQ ID NO:44 and a humanized light chain comprising the three CDRs of SEQ ID NO:45 provided that position L46 (Kabat numbering) is occupied by F and/or position L49 (Kabat numbering) is occupied by C and/or position L83 (Kabat numbering) is occupied by F, and/or position H11 (Kabat numbering) is occupied by V, and/or position H28 (Kabat numbering) is occupied by T, and/or position H38 (Kabat numbering) is occupied by R, and/or position H48 (Kabat numbering) is occupied by M, and/or position H67 (Kabat numbering) is occupied by A, and/or position H69 (Kabat numbering) is occupied by M, and/or position H71 (Kabat numbering) is occupied by A, and/or position H91 (Kabat numbering) is occupied by Y, and/or position H97 (Kabat numbering) is occupied by C. In some of such antibodies, position L46 (Kabat numbering) is occupied by F, and position L49 (Kabat numbering) is occupied by C. In some of such antibodies, position H67 (Kabat numbering) is occupied by A, and position H71 (Kabat numbering) is occupied by A. In some of such antibodies, position L46 (Kabat numbering) is occupied by F, position H67 (Kabat numbering) is occupied by A, position H71 (Kabat numbering) is occupied by A, and position L49 (Kabat numbering) is occupied by C. In some of such antibodies, position H11 (Kabat numbering) is occupied by V and position H38 (Kabat numbering) is occupied by R. In some of such antibodies, position H28 (Kabat numbering) is occupied by T, position H48 (Kabat numbering) is occupied by M, position H69 (Kabat numbering) is occupied by M, and position H91 (Kabat numbering) is occupied by Y. In some of such antibodies, position L49 (Kabat numbering) is occupied by C and position L83 (Kabat numbering) is occupied by F. In some of such antibodies, position H28 (Kabat numbering) is occupied by T, position H48 (Kabat numbering) is occupied by M, position H69 (Kabat numbering) is occupied by M, position H91 (Kabat numbering) is occupied by Y, position L49 (Kabat numbering) is occupied by C, and position L83 (Kabat numbering) is occupied by F. In some of such antibodies, position H97 (Kabat numbering) is occupied by C. In some of such antibodies, position L46 (Kabat numbering) is occupied by F, position L49 (Kabat numbering) is occupied by C, position L83 (Kabat numbering) is occupied by F, position H11 (Kabat numbering) is occupied by V, H28 (Kabat numbering) is occupied by T, position H38 (Kabat numbering) is occupied by R, position H48 (Kabat numbering) is occupied by M, position H67 (Kabat numbering) is occupied by A, position H69 (Kabat numbering) is occupied by M, position H71 (Kabat numbering) is occupied by A, position H91 (Kabat numbering) is occupied by Y, and H97 (Kabat numbering) is occupied by C.

The invention further provides an antibody comprising a mature heavy chain variable region having an amino acid sequence at least 90% identical to SEQ ID NO:23 and a mature light chain variable region at least 90% identical to SEQ ID NO:37. In some of such antibodies, the mature heavy chain variable region comprises the three Kabat CDRs of SEQ ID NO:23 and the mature light chain variable region comprising the three Kabat CDRs of SEQ ID NO:37, and position H67 (Kabat numbering) is occupied by A, H71 (Kabat numbering) is occupied by A, position L46 (Kabat numbering) is occupied by F, and position L49 (Kabat numbering) is occupied by C. In some of such antibodies, position L83 (Kabat numbering) is occupied by F. In some of such antibodies, position H97 (Kabat numbering) is occupied by C. In some of such antibodies, the mature heavy chain has at least 95% sequence identity to SEQ ID NO:23 and the mature light chain has at least 95% sequence identity to SEQ ID NO:37. In some of such antibodies, any differences in CDRs of the mature heavy chain variable region and mature light variable region from SEQ ID NOs. 52 and 60 respectively reside in positions H60-H65. In some of such antibodies, the $K_D$ for alpha-synuclein of the antibody is from about 0.5 to 2 of $K_D$ for alpha-synuclein of a murine or chimeric 1H7 antibody. In some of such antibodies, position L83 (Kabat numbering) is occupied by F or A, position H11 (Kabat numbering) is occupied by V, H28 (Kabat numbering) is occupied by T, position H38 (Kabat numbering) is occupied by R, position H48 (Kabat numbering) is occupied by M, position H67 (Kabat numbering) is occupied by A, position H69 (Kabat numbering) is occupied by M, position H71 (Kabat numbering) is occupied by A, position H91 (Kabat numbering) is occupied by Y, and H97 (Kabat numbering) is occupied by C. In some of such antibodies, position L83 (Kabat numbering) is occupied by F. In some of such antibodies, position H97 (Kabat numbering) is occupied by C. In some of such antibodies, any difference in the variable region framework of the mature heavy chain variable region and SEQ ID NO:23 are one or more of position H11 (Kabat numbering) occupied by V, H28 (Kabat numbering) occupied by T, position H38 (Kabat numbering) occupied by R, position H48 (Kabat numbering) occupied by M, position H69 (Kabat numbering) occupied by M, and position H91 (Kabat numbering) occupied by Y. In some of such antibodies, any difference in the variable region framework of the mature light chain variable region and SEQ ID NO:37 is position L83 (Kabat numbering) occupied by F or A. In some of such antibodies, the mature heavy chain variable region has an amino acid sequence designated SEQ ID NO:23 and the mature light chain variable region has an amino acid sequence designated SEQ ID NO:37.

In some antibodies, the mature heavy chain variable region has an amino acid sequence designated SEQ ID NO:44 and the mature light chain variable region has an amino acid sequence designated SEQ ID NO:45, 33, 35, 37, or 39. In some antibodies, the mature heavy chain variable region has an amino acid sequence designated SEQ ID NO:19 and the mature light chain variable region has an amino acid sequence designated SEQ ID NO: 45, 33, 35, 37, or 39. In some antibodies, the mature heavy chain variable region has an amino acid sequence designated SEQ ID NO:21 and the mature light chain variable region has an amino acid sequence designated SEQ ID NO:45, 33, 35, 37, or 39. In some antibodies, the mature heavy chain variable region has an amino acid sequence designated SEQ ID NO:23 and the mature light chain variable region has an amino acid sequence designated SEQ ID NO: 45, 33, 35, 37, or 39. In some antibodies, the mature heavy chain variable region has an amino acid sequence designated SEQ ID NO:25 and the mature light chain variable region has an amino acid sequence designated SEQ ID NO: 45, 33, 35, 37, or 39. In some antibodies, the mature heavy chain variable region has an amino acid sequence designated SEQ ID NO:27 and the mature light chain variable region has an amino acid sequence designated SEQ ID NO: 45, 33, 35, 37, or 39.

In any of the above antibodies, the mature heavy chain variable region can be fused to a heavy chain constant region and the mature light chain constant region can be fused to a light chain constant region.

In any of the above antibodies, the heavy chain constant region can be a mutant form of natural human constant region which has reduced binding to an Fcγ receptor relative to the natural human constant region.

In any of the above antibodies, the heavy chain constant region can be of human IgG1 isotype. In some antibodies the allotype is G1m3. In some antibodies, the allotype is G1m1.

In some antibodies, the heavy chain constant region has the amino acid sequence designated SEQ ID NO:52 provided the C-terminal lysine residue may be omitted. In some antibodies, the light chain constant region has the amino acid sequence designated SEQ ID NO:49. In some antibodies, the mature heavy chain variable region is fused to a heavy chain constant region having the amino acid sequence designated SEQ ID NO:52 provided the C-terminal lysine residue may be omitted and the mature light chain constant region is fused to a light chain constant region having the amino acid sequence designated SEQ ID NO:49. In some antibodies, the mature light chain comprises SEQ ID NO:53 and the mature heavy chain comprises SEQ ID NO:56.

The invention further provides a nucleic acid encoding any of the above-mentioned mature heavy chain variable regions and/or any of the above-mentioned mature light chain variable region, e.g., SEQ ID NOS: 18, 20, 22, 24, 26, 32, 34, 36, or 38.

The invention further provides a host cell comprising a vector comprising any of the nucleic acids described above.

The invention further provides a pharmaceutical composition comprising any of the above-mentioned antibodies.

The invention further provides a method of treating a patient having or at risk of a Lewy body disease, comprising administering to the patient an effective regime of any of the above-mentioned antibodies. In some methods, the disease is Parkinson's disease. In some methods, decline of cognitive function in the patient is inhibited. In some methods, neuritic and/or axonal alpha synuclein aggregates are reduced. In some methods, neuritic dystrophy in the patient is reduced. In some methods, synaptic and/or dendritic density is preserved. In some methods, the method preserves synaptophysin and/or MAP2 in the patient.

The invention further provides a method of reducing Lewy body formation in a patient having or at risk of a Lewy body disease, comprising administering to the patient an effective amount of any of the above-mentioned antibodies. In some methods, the disease is Parkinson's disease. In some methods, decline of cognitive function in the patient is inhibited. In some methods, neuritic and/or axonal alpha synuclein aggregates are reduced. In some methods, neuritic dystrophy in the patient is reduced. In some methods, synaptic and/or dendritic density is preserved. In some methods, the method preserves synaptophysin and/or MAP2 in the patient.

The invention further provides a method of inhibiting synuclein aggregation or clearing Lewy bodies or synuclein aggregates in a patient having or at risk of a Lewy body disease, comprising administering to the patient an effective amount of any of the above-mentioned antibodies. In some methods, the disease is Parkinson's disease. In some methods, decline of cognitive function in the patient is inhibited. In some methods, neuritic and/or axonal alpha synuclein aggregates are reduced. In some methods, neuritic dystrophy in the patient is reduced. In some methods, synaptic and/or dendritic density is preserved. In some methods, the method preserves synaptophysin and/or MAP2 in the patient.

The invention further provides methods of detecting Lewy bodies in a patient having or at risk of a Lewy body disease, comprising administering to the patient an effective amount of any of the above-mentioned antibodies, wherein the antibody binds to Lewy bodies and bound antibody is detected. In some methods, the disease is Parkinson's disease. In some methods, the antibody is labeled.

The invention further provides a method of producing an antibody, comprising culturing cells transformed with nucleic acids encoding the heavy and light chains of the antibody, so that the cell secrete the antibody; and purifying the antibody from cell culture media; wherein the antibody is any of the antibodies described above.

The invention further provides a method producing a cell line producing an antibody, comprising introducing a vector encoding heavy and light chains of an antibody and a selectable marker into cells; propagating the cells under conditions to select for cells having increased copy number of the vector; isolating single cells from the selected cell; and banking cells cloned from a single cell selected based on yield of antibody; wherein the antibody is any of the antibodies described above. Some such methods further comprises propagating the cells under selective conditions and screening for cell lines naturally expressing and secreting at least 100 mg/L/$10^6$ cells/24 h.

BRIEF DESCRIPTION OF THE DRAWINGS

FIGS. 1A-B shows an alignment of the amino acid sequences of m1H7 with four versions the humanized 1H7 heavy chain mature variable region. BAC02037 (SEQ ID NO:42) is human acceptor $V_H$ sequence. CDR regions according to Kabat definition are underlined and in bold.

FIGS. 2A-B shows an alignment of the amino acid sequences of m1H7 with four versions the humanized 1H7 light chain mature variable region. AAY33358 (SEQ ID NO:43) is human acceptor $V_L$ sequence. CDR regions according to Kabat definition are underlined and in bold.

FIGS. 4 A-C shows binding kinetic parameters (ForteBio) humanized 1H7 (Hu1H7VHv2-Hu1H7VLv4, Hu1H7VHv3-Hu1H7VLv1, Hu1H7VHv3-Hu1H7VLv2, Hu1H7VHv3-Hu1H7VLv3, Hu1H7VHv3-Hu1H7VLv4, Hu1H7VHv4-Hu1H7VLv1) and chimeric 1H7.

BRIEF DESCRIPTION OF THE SEQUENCES

Figure 3A:
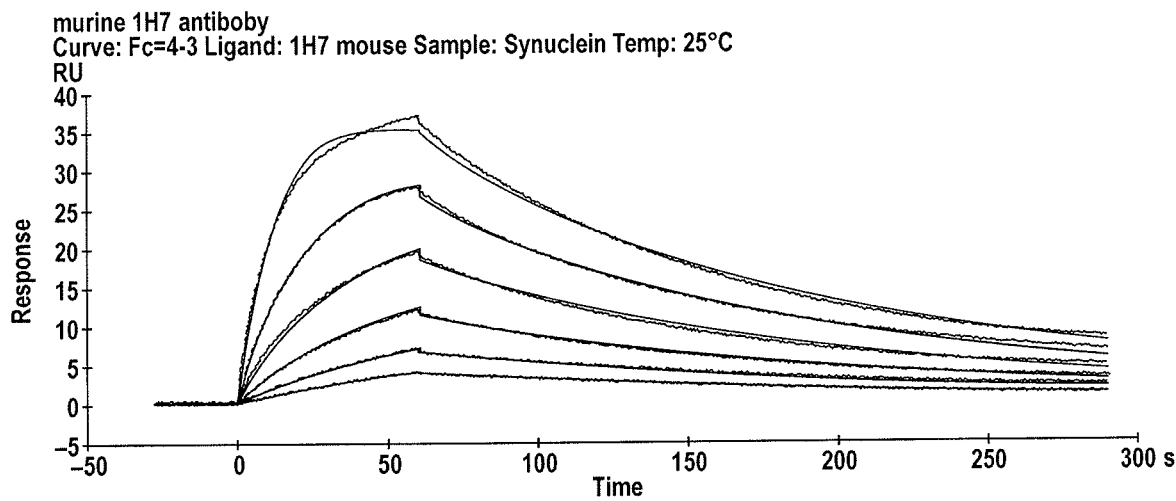
FIGS. 3 A-C shows Biacore binding kinetic analysis of murine 1H7 (A), chimeric 1H7 (B) and humanized 1H7 Hu1H7VHv3-Hu1H7VLv3, respectively.

SEQ ID NO:1 is the natural human wildtype alpha-synuclein amino acid sequence.

SEQ ID NO:2 is the non-amyloid component (NAC) domain of alpha-synuclein as reported by Jensen et al. (Biochem. J. 310 (Pt 1): 91-94, 1995; GenBank accession number S56746).

SEQ ID NO:3 is the non-amyloid component (NAC) domain of alpha-synuclein as reported by Uéda et al. (Proc. Natl. Acad. Sci. USA, 90:11282-6, 1993).

SEQ ID NO:4 is the murine 1H7 antibody(m1H7) heavy chain variable nucleotide sequence.

SEQ ID NO:5 is the m1H7 heavy chain variable amino acid sequence.

SEQ ID NO:6 is the m1H7 light chain variable nucleotide sequence.

SEQ ID NO:7 is the m1H7 light chain variable amino acid sequence.

SEQ ID NO:8 is the mature m1H7 heavy chain variable nucleotide sequence.

SEQ ID NO:9 is the mature m1H7 heavy chain variable amino acid sequence.

SEQ ID NO:10 is the mature m1H7 light chain variable nucleotide sequence.

SEQ ID NO:11 is the mature m1H7 light chain variable amino acid sequence.

SEQ ID NO:12 is the m1H7 heavy chain CDR1 (Kabat definition).

SEQ ID NO:13 is the m1H7 heavy chain CDR2 (Kabat definition).

SEQ ID NO:14 is the m1H7 heavy chain CDR3 (Kabat definition).

SEQ ID NO:15 the m1H7 light chain CDR1 (Kabat definition).

SEQ ID NO:16 is the m1H7 light chain CDR2 (Kabat definition).

SEQ ID NO:17 is the m1H7 light chain CDR3 (Kabat definition).

SEQ ID NO:18 is the Hu1H7VHv1 nucleic acid sequence.

SEQ ID NO:19 is the Hu1H7VHv1 amino acid sequence.

SEQ ID NO:20 is the Hu1H7VHv2 nucleic acid sequence.

SEQ ID NO:21 is the Hu1H7VHv2 amino acid sequence.

SEQ ID NO:22 is the Hu1H7VHv3 nucleic acid sequence.

SEQ ID NO:23 is the Hu1H7VHv3 amino acid sequence.

SEQ ID NO:24 is the Hu1H7VHv4 nucleic acid sequence.

SEQ ID NO:25 is the Hu1H7VHv4 amino acid sequence.

SEQ ID NO:26 is the Hu1H7VHv5 nucleic acid sequence.

SEQ ID NO:27 is the Hu1H7VHv5 amino acid sequence.

SEQ ID NO:28 is the Hu1H7VH signal peptide nucleic acid sequence.

SEQ ID NO:29 is the Hu1H7VH signal peptide amino acid sequence.

SEQ ID NO:30 is the Hu1H7VH signal peptide nucleic acid sequence.

SEQ ID NO:31 is the Hu1H7VH signal peptide amino acid sequence.

SEQ ID NO:32 is the Hu1H7VLv1 nucleic acid sequence.

SEQ ID NO:33 is the Hu1H7VLv1 amino acid sequence.

SEQ ID NO:34 is the Hu1H7VLv2 nucleic acid sequence.

SEQ ID NO:35 is the Hu1H7VLv2 amino acid sequence.

SEQ ID NO:36 is the Hu1H7VLv3 nucleic acid sequence.

SEQ ID NO:37 is the Hu1H7VLv3 amino acid sequence.

SEQ ID NO:39 is the Hu1H7VLv4 amino acid sequence.

SEQ ID NO:40 is the Hu1H7VL signal peptide nucleic acid sequence.

SEQ ID NO:41 is the Hu1H7VL signal peptide amino acid sequence.

SEQ ID NO:42 is the BAC02037 (GI-21670055) human acceptor used for heavy chain framework Amino acid sequence.

SEQ ID NO:43 is the AAY33358 (GI-63102905) human acceptor used for light chain framework amino acid sequence.

SEQ ID NO:44 is the Hu1H7VH having no backmutation or CDR mutation.

SEQ ID NO:45 is the Hu1H7VL having no backmutation or CDR mutation.

SEQ ID NO:46 is the sequence for Hu1H7VH alternatives.

SEQ ID NO:47 is the sequence for Hu1H7VL alternatives.

SEQ ID NO:48 is the sequence for Hu1H7VH CDR3 alternatives.

SEQ ID NO:49 is the Hu1H7 light chain constant region (with arginine) (common for v1-v4).

SEQ ID NO:50 is the Hu1H7 heavy chain constant region (IgG1; common for v1-v5).

SEQ ID NO:51 is the Hu1H7 light chain constant region (without arginine) (common for v1-v4).

SEQ ID NO:52 is the Hu1H7 heavy chain constant region (G1m3 allotype).

SEQ ID NO:53 is the Hu1H7 light chain version 3 (variable region+constant region with arginine).

SEQ ID NO:54 is the Hu1H7 light chain version 3 (variable region+constant region without arginine).

SEQ ID NO:55 is the Hu1H7 heavy chain version 3 (variable region+constant region).

SEQ ID NO:56 is the Hu1H7 heavy chain version 3 (variable region+constant region; G1m3 allotype).

SEQ ID NO:57 is the Hu1H7 heavy chain constant region (IgG2).

SEQ ID NO:58 is the Hu1H7 heavy chain constant region (G1m1 allotype).

Definitions

Monoclonal antibodies are typically provided in isolated form. This means that an antibody is typically at least 50% w/w pure of proteins and other macromolecules arising from its production or purification but does not exclude the possibility that the monoclonal antibody is combined with an excess of pharmaceutical acceptable carrier(s) or other vehicle intended to facilitate its use. Sometimes monoclonal antibodies are at least 60%, 70%, 80%, 90%, 95 or 99% w/w pure of proteins and other macromolecules from production or purification.

Specific binding of a monoclonal antibody to its target antigen means an affinity of at least $10^6$, $10^7$, $10^8$, $10^9$, or $10^{10}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that a monoclonal antibody binds one and only one target.

The basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region means a light chain variable region without the light chain signal peptide. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. (See generally, Fundamental Immunology (Paul, W., ed., 2nd ed. Raven Press, N.Y., 1989, Ch. 7, incorporated by reference in its entirety for all purposes).

The mature variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md., 1987 and 1991), or Chothia & Lesk, J. Mol. Biol. 196:901-917 (1987); Chothia et al., Nature 342:878-883 (1989). Kabat also provides a widely used numbering convention (Kabat numbering) in which corresponding residues between different heavy chains or between different light chains are assigned the same number (e.g., H83 means position 83 by Kabat numbering in the mature heavy chain variable region; likewise position L36 means position 36 by Kabat numbering in the mature light chain variable region). Kabat numbering is used throughout in referring to positions in the variable region of an antibody unless explicitly stated otherwise.

The term "antibody" includes intact antibodies and binding fragments thereof. Typically, fragments compete with the intact antibody from which they were derived for specific binding to the target including separate heavy chains, light chains Fab, Fab', F(ab')$_2$, F(ab)c, diabodies, Dabs, nanobodies, and Fv. Fragments can be produced by recombinant DNA techniques, or by enzymatic or chemical separation of intact immunoglobulins. The term "antibody" also includes a bispecific antibody and/or a humanized antibody. A bispecific or bifunctional antibody is an artificial hybrid antibody having two different heavy/light chain pairs and two different binding sites (see, e.g., Songsivilai and Lachmann, Clin. Exp. Immunol., 79:315-321 (1990); Kostelny et al., J. Immunol. 148:1547-53 (1992)). In some bispecific antibodies, the two different heavy/light chain pairs include a humanized 1H7 heavy chain/light chain pair and a heavy chain/light chain pair specific for a different epitope on alpha synuclein than that bound by 1H7.

In some bispecific antibodies, one heavy chain light chain pair is a humanized 1H7 antibody as further disclosed below and the heavy light chain pair is from an antibody that binds to a receptor expressed on the blood brain barrier, such as an insulin receptor, an insulin-like growth factor (IGF) receptor, a leptin receptor, or a lipoprotein receptor, or a transferrin receptor (Friden et al., PNAS 88:4771-4775, 1991; Friden et al., Science 259:373-377, 1993). Such a bispecific antibody can be transferred cross the blood brain barrier by receptor-mediated transcytosis. Brain uptake of the bispecific antibody can be further enhanced by engineering the bi-specific antibody to reduce its affinity to the blood brain barrier receptor. Reduced affinity for the receptor resulted in a broader distributioin in the brain (see, e.g., Atwal. et al. *Sci. Trans. Med.* 3, 84ra43, 2011; Yu et al. *Sci. Trans. Med.* 3, 84ra44, 2011).

Exemplary bispecific antibodies can also be (1) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (2) a Tandab, which is a fusion of two single chain diabodies resulting in a tetravalent bispecific antibody that has two binding sites for each of the target antigens; (3) a flexibody, which is a combination of scFvs with a diabody resulting in a multivalent molecule; (4) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (5) a so-called Scorpion molecule, comprising, e.g., two scFvs fused to both termini of a human Fc-region. Examples of platforms useful for preparing bispecific antibodies include but are not limited to Bi (Micromet), DART (MacroGenics), Fcab and Mab2 (F-star), Fc-engineered IgG1 (Xencor) or DuoBody (based on Fab arm exchange, Genmab).

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined by X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., Cancer Res. 50:1495, 1990). A test antibody competes with a reference antibody if an excess of a test antibody (e.g., at least 2×, 5×, 10×, 20× or 100×) inhibits binding of the reference antibody by at least 50%, for example, 75%, 90% or 99% as measured in a competitive binding assay. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

A "patient" includes a human or other mammalian subject that receive either prophylactic or therapeutic treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" one or more recited elements may include other elements not specifically recited. For example, a composition that comprises antibody may contain the antibody alone or in combination with other ingredients.

Designation of a range of values includes all integers within or defining the range, and all subranges defined by integers within the range.

Unless otherwise apparent from the context, the term "about" encompasses values within a standard margin of error of measurement (SEM) of a stated value.

An individual is at increased risk of a disease if the subject has at least one known risk-factor (e.g., genetic, biochemical, family history, situational exposure) placing individuals with that risk factor at a statistically significant greater risk of developing the disease than individuals without the risk factor.

The term "symptom" refers to a subjective evidence of a disease, such as altered gait, as perceived by the patient. A "sign" refers to objective evidence of a disease as observed by a physician.

Statistical significance means $p \leq 10.05$.

"Cognitive function" refers to mental processes such as any or all of attention, memory, producing and understanding language, solving problems, and making an interest in one's surroundings and self-care.

"Enhanced cognitive function" or "improved cognitive function" refers to improvement relative to a baseline, for example, diagnosis or initiation of treatment. "Decline of cognitive function" refers to a decrease in function relative to such a base line.

In animal model systems such as rat or mouse, cognitive function may be measured methods including using a maze in which subjects use spatial information (e.g., Morris water maze, Barnes circular maze, elevated radial arm maze, T maze and others), fear conditioning, active avoidance, illuminated open-field, dark activity meter, elevated plus-maze, two-compartment exploratory test or forced swimming test.

In humans, cognitive function can be measured by one or more of several standardized tests. Examples of a test or assay for cognitive function were described (Ruoppila, l. and Suutama, T. Scand. J. Soc. Med. Suppl. 53,44-65, 1997) and include standardized psychometric tests (e.g. Wechsler Memory Scale, the Wechsler Adult Intelligence Scale, Raven's Standard Progressive Matrices, Schaie-Thurstone Adult Mental Abilities Test), neuropsychological tests (e.g. Luria-Nebraska), metacognitive self-evaluations (e.g. Metamemory Questionnaire), visual-spatial screening tests (e.g. Poppelreuter's Figures, Clock Recognition, Honeycomb Drawing and Cancellation), cognitive screening tests (e.g. Folstein's Mini Mental State Test) and reaction time tests. Other standard tests for cognitive performance include the Alzheimer's Disease Assessment Scale-cognitive subscale (ADAS-cog); the clinical global impression of change scale (CIBIC-plus scale); the Alzheimer's Disease Cooperative Study Activities of Daily Living Scale (ADCS-ADL); the Mini Mental State Exam (MMSE); the Neuropsychiatric Inventory (NPI); the Clinical Dementia Rating Scale (CDR); the Cambridge Neuropsychological Test Automated Battery (CANTAB) or the Sandoz Clinical Assessment-Geriatric (SCAG), Stroop Test, Trail Making, Wechsler Digit Span, and the CogState computerized cognitive test. In addition, cognitive function may be measured using imaging techniques such as Positron Emission Tomography (PET), functional magnetic resonance imaging (fMRI), Single Photon Emission Computed Tomography (SPECT), or any other imaging technique that allows one to measure brain function.

DETAILED DESCRIPTION OF THE INVENTION

I. General

The invention provides humanized 1H7 antibodies (Hu1H7 antibodies). The antibodies are useful for treatment and diagnoses of a Lewy body disease.

II. Target Molecules

Natural human wildtype alpha-synuclein is a peptide of 140 amino acids having the following amino acid sequence:

```
                                          (SEQ ID NO: 1)
MDVFMKGLSK AKEGVVAAAE KTKQGVAEAA GKTKEGVLYV

GSKTKEGVVH GVATVAEKTK EQVTNVGGAV VTGVTAVAQK

TVEGAGSIAA ATGFVKKDQL GKNEEGAPQE GILEDMPVDP

DNEAYEMPSE EGYQDYEPEA
```

(Uéda et al., Proc. Natl. Acad. Sci. USA, 90:11282-6, 1993; GenBank accession number: P37840). The protein has three recognized domains, a KTKE repeat domain covering amino acids 1-61, a NAC (Non-amyloid component) domain running from about amino acids 60-95, and a C-terminal acidic domain running from about amino acid 98 to 140. Jensen et al. have reported NAC has the amino acid sequence: EQVTNVGGAVVTGVTAVAQKTVEGAGSIAAATGFV (SEQ ID NO: 2) (Jensen et al., Biochem. J. 310 (Pt 1): 91-94, 1995; GenBank accession number S56746). Uéda et al. have reported NAC has the amino acid sequence: KEQVTNVGGAVVTGVTAVAQKTVEGAGS (SEQ ID NO: 3) (Uéda et al., Proc. Natl. Acad. Sci. USA, 90:11282-6, 1993).

Unless otherwise apparent from the context, reference to alpha-synuclein or its fragments includes the natural human wildtype amino acid sequences indicated above, and human allelic variants thereof, particularly those associated with Lewy body disease (e.g., E46K, A30P and A53T, with the first letter indicates the amino acid in SEQ ID NO:1, the number is the codon position in SEQ ID NO:1, and the second letter is the amino acid in the allelic variant). Such variants can optionally be present individually or in any combination. The induced mutations E83Q, A90V, A76T, which enhance alpha synuclein aggregation, can also be present individually or in combination with each other and/or human allelic variants E46K, A30P and A53T.

III. Lewy Body Diseases

Lewy Body Diseases (LBD) are characterized by degeneration of the dopaminergic system, motor alterations, cognitive impairment, and formation of Lewy bodies (LBs). (McKeith et al., Neurology (1996) 47:1113-24). Lewy Bodies are spherical protein deposits found in nerve cells. Their presence in the brain disrupts the brain's normal function interrupting the action of chemical messengers including acetylcholine and dopamine. Lewy Body diseases include Parkinson's disease (including idiopathic Parkinson's disease), Diffuse Lewy Body Disease (DLBD) also known as Dementia with Lewy Bodies (DLB), Lewy body variant of Alzheimer's disease (LBV), Combined Alzheimer's and Parkinson disease and as multiple system atrophy (MSA; e.g., Olivopontocerebellar Atrophy, Striatonigral Degeneration and Shy-Drager Syndrome). DLBD shares symptoms of both Alzheimer's and Parkinson's disease. DLBD differs from Parkinson's disease mainly in the location of Lewy Bodies. In DLBD Lewy Bodies form mainly in the cortex. In Parkinson's disease, they form mainly in the substantia nigra. Other Lewy Body diseases include Pure Autonomic Failure, Lewy body dysphagia, Incidental LBD, and Inherited LBD (e.g., mutations of the alpha-synuclein gene, PARK3 and PARK4).

IV. Antibodies of the Invention

A. Binding Specificity and Functional Properties

Humanized antibodies of the invention specifically bind to human alpha synuclein. The affinity of some humanized antibodies (i.e., Ka) is can be, for example, within a factor of five or two of that of the mouse antibody (m1H7). Some humanized antibodies have an affinity that is the same, within SEM, as m1H7. Some humanized antibodies have an affinity greater than that of mouse 1H7. Preferred humanized antibodies bind to the same epitope and/or compete with m1H7 for binding to human alpha synuclein.

B. Humanized Antibodies

A humanized antibody is a genetically engineered antibody in which the CDRs from a non-human "donor" antibody are grafted into human "acceptor" antibody sequences (see, e.g., Queen et al., U.S. Pat. Nos. 5,530,101 and 5,585,089; Winter et al., U.S. Pat. No. 5,225,539; Carter, U.S. Pat. No. 6,407,213; Adair, U.S. Pat. Nos. 5,859,205 and 6,881,557; and Foote, U.S. Pat. No. 6,881,557). The acceptor antibody sequences can be, for example, a mature human antibody variable region sequence, a composite of such sequences, a consensus sequence of human antibody variable region sequences (e.g., light and heavy chain variable region consensus sequences of Kabat, 1991, supra), or a germline variable region sequence.

An example of an acceptor sequence for the heavy chain is the human mature heavy chain variable region with NCBI accession code BAC02037 (GI: 21670055). This acceptor sequence includes two CDRs having the same canonical form as mouse 1H7 heavy chain and has a sequence identity of 65.8% in the heavy chain variable region framework. If a different acceptor sequence is used, such an acceptor is can be, for example, another mature heavy chain variable region derived from germline VH1-18 or a mature heavy chain variable region sequence incorporating one of these germ line sequences.

For the light chain, an example of an acceptor sequence is the light chain mature variable region with NCBI accession code AAY33358 (GI:63102905). This acceptor sequence includes two CDRs having the same canonical form as a mouse 1H7 light chain and has a sequence identity of 65.4% in the light chain variable region framework. If a different acceptor is used, such an acceptor is preferably another mature light chain sequence derived from the germline A30 or a light chain mature variable region sequence incorporating one of these germ line sequences.

A humanized antibody of the invention is an antibody having three light chain and three heavy chain CDRs as defined by Kabat entirely or substantially from the donor mouse 1H7 antibody and mature variable region framework sequences and constant regions, if present, entirely or substantially from human antibody sequences. Likewise a humanized heavy chain is a heavy chain having three heavy chain CDRs as defined by Kabat entirely or substantially from the heavy chain of the mouse 1H7 antibody, and a mature heavy chain variable sequence and heavy chain constant region sequence, if present, entirely or substantially from human antibody heavy chain sequence. Likewise a humanized light chain is a light chain having three light chain CDRs as defined by Kabat entirely or substantially from the light chain of the m1H7 antibody, and a mature light chain variable sequence and light chain constant region sequence, if present, entirely or substantially from human antibody light chain sequence. A CDR is substantially from m1H7 if at least 60%, 70%, 80%, 85%, 90%, 95%, 96%, 97%, 98%, 99% or 100% of residues are identical to the corresponding residues in the corresponding CDR of m1H7. The mature variable region framework sequences of an antibody chain or the constant region sequence of an antibody chain are substantially from a human mature variable region framework sequence or human constant region sequence respectively when at least 85%, 90%, 95%, 96%, 97%, 98%, 99% or 100% of corresponding residues defined by Kabat are identical.

Certain amino acids from the human mature variable region framework residues can be selected for substitution based on their possible influence on CDR conformation and/or binding to antigen, mediating interaction between heavy and light chains, interaction with the constant region, being a site for desired or undesired post-translational modification, being an unusual residue for its position in a human variable region sequence and therefore potentially immunogenic, among other reasons. The following 11 variable region framework positions were considered as candidates for substitutions for one or more of these reasons as further specified in the Examples (L46F, Y49C, F83A, V11L, T28S, R38K, M48I, V67A, M69L, T71A, Y91F).

Here as elsewhere, the first-mentioned residue is the residue of a humanized antibody formed by grafting Kabat CDRs into a human acceptor framework, and the second-mentioned residue is a residue being considered for replacing such residue. Thus within variable region frameworks, the first mentioned residue is human and within CDRs the first mentioned residue is mouse (e.g., C97S).

Amino acid substitutions can be made in the CDRs. One possible variation is to substitute certain residues in the CDRs of the mouse 1H7 antibody with corresponding residues from human CDRs sequences, typically from the CDRs of the human acceptor sequences used in designing the exemplified humanized antibodies. In some antibodies only part of the CDRs, namely the subset of CDR residues required for binding, termed the SDRs, are needed to retain binding in a humanized antibody. CDR residues not contacting antigen and not in the SDRs can be identified based on previous studies (for example residues H60-H65 in CDR H2 are often not required), from regions of Kabat CDRs lying outside Chothia hypervariable loops (Chothia, J. Mol. Biol. 196:901, 1987), by molecular modeling and/or empirically, or as described in Gonzales et al., Mol. Immunol. 41:863 (2004). In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

One reason for performing a substitution within a CDR is that a mouse residue is a site of posttranslational modification that may interfere with expression or assembly of an antibody. Here, position H97 within CDRH3, which is occupied by a C in mouse 1H7 was identified as a site for substitution.

The 11 variable region framework backmutations and 1 CDR substitution noted above can be incorporated into humanized 1H7 antibodies in many permutations. The heavy chain variable region of such antibodies can be represented by a sequence comprising QVQLVQSGAE-$X_1$-KKPGASVKVSCKASGY-$X_2$-FTSYYIHWV-$X_3$-QAPGQ-GLEW-$X_4$-GWIYPGSGNTKYSEKFKGR-$X_5$-T-$X_6$-T-$X_7$-DTSTSTAYMELRSLRSDDTAVY-$X_8$-CARDG-$X_9$-YGFAYWGQGTLVTVSS, wherein -$X_1$- is V or L; -$X_2$- is S or T; -$X_3$- is R or K; -$X_4$- is M or I; -$X_5$- is V or A; -$X_6$- is M or L; -$X_7$- is T or A; -$X_8$- is Y or F; -$X_9$- is C, M, S, or T (SEQ ID NO:46). In some heavy chain variable regions, -$X_9$- is C. Some light chain variable regions can be represented by a sequence comprising DIQLTQSPSSL-SASVGDRVTITCK-ASQSVDYDGDSYMNWYQQKPGKAPK-$Z_1$-LI-$Z_2$-AASNLESGVPSRFSGSGSGTDFTLTISSLQPED-$Z_3$-ATYYCQQSNEDPFTFGQGTKLEIK, wherein -$Z_1$- is L or F; -$Z_2$- is Y or C; -$Z_3$- is F or A (SEQ ID NO:47). In some antibodies the heavy chain variable region comprises SEQ ID NO: 46 and the light chain variable region comprises SEQ ID NO:47. For example, residues, $X_1$ and $X_3$ of SEQ ID NO: 48 are V and R, respectively. For example, residues, $X_5$- and $X_7$ of SEQ ID NO:46 are A and residue $Z_1$ of SEQ ID NO:47 is F. For example, residues, -$X_4$, $X_6$, and $X_8$ of SEQ ID NO:46 are M, M, and Y, respectively, and residue $Z_2$ and $_3$ of SEQ ID NO:47 are C and F, respectively. For example, residues, $X_2$ and $X_9$ of SEQ ID NO: 48 are T and C, respectively.

Some antibodies contain two heavy chain substitutions and two light chain substitutions. For example, position H67 is occupied by A, H71 is occupied by A, position L46 is occupied by F, and position L49 is occupied by C. In some antibodies, the heavy chain mature variable region has an amino acid sequence designated SEQ ID NO:23. In some antibodies, the light chain mature variable region has an amino acid sequence designated SEQ ID NO:37. For example, in H3L3 (Hu1H7VHv3 (SEQ ID NO:23-Hu1H7VLv3 (SEQ ID NO:37)), the heavy chain mature variable region has an amino acid sequence designated SEQ ID NO:23, and the light chain mature variable region has an amino acid sequence designated SEQ ID NO:37.

The invention provides variants of the H3L3 humanized antibody in which the humanized heavy chain mature variable region shows at least 90%, 95%, 96%, 97%, 98% or 99% identity to SEQ ID NO:23 and the humanized light chain mature variable region shows at least 90%, 95%, 96%, 97%, 98% or 99% sequence identity to SEQ ID NO:37. Some such humanized antibodies include three heavy and three light chain CDRs entirely or substantially identical to the CDR regions of H3L3, which are the same as those of the mouse donor antibody. The CDR regions can be defined by any conventional definition (e.g., Chothia) but are preferably as defined by Kabat.

Some variants of the H3L3 humanized antibody retain some or all of the backmutations in H3L3. In other words, at least 1, 2, 3 or preferably all 4 of the following are present: H67 is occupied by A, and H71 is occupied by A, L46 is occupied by F, and position L49 is occupied by C.

In addition to retaining at least 1, 2, 3 or preferably all 4 of the backmutations of H3L3, humanized 1H7 antibodies may also contain additional backmutations in the variable region frameworks. Examples of such backmutations include H11 occupied by L, H28 occupied by S, H38 occupied by K, H48 occupied by I, H69 occupied by L, H91 occupied by F, and/or L83 occupied by A. For selection of backmutations for a therapeutic or diagnostic product, one should take into account the degree to which they in general do not improve affinity and the degree to which introducing more mouse residues may give increased risk of immunogenicity. For example, H3L1 comprises a heavy chain mature variable region of SEQ ID NO:23, and a light chain of SEQ ID NO:33. For example, H4L1 comprises a heavy chain mature variable region of SEQ ID NO:25, and a light chain of SEQ ID NO:33.

Another possibility for variation is to use a different human acceptor sequences as discusseed above. Substitutions in CDR regions are possible as described above, for example at position H97, but prior to selecting such substitutions for a therapeutic or diagnostic product, one should consider the potential effect on affinity and antibody expression.

If position H97 in mouse CDRH3 is other than cysteine, it is preferably occupied by M, S, or T. Some antibodies comprise a humanized heavy chain comprising Kabat CDR1 of SEQ ID NO:12: SYYIH; Kabat CDR2 of SEQ ID NO:13: WIYPGSGNTKYSEKFKG; Kabat CDR3 of SEQ ID NO:48: DG-$X_9$-YGFAY, wherein -$X_9$- is C, M, S, or T, more preferably C. Some antibodies comprise a humanized light chain comprising Kabat CDR1 of SEQ ID NO:15: KASQSVDYDGDSYMN; Kabat CDR2 of SEQ ID NO:16: AASNLES; Kabat CDR3 of SEQ ID NO:17: QQSNEDPFT. Some antibodies comprise a humanized heavy chain comprising the three Kabat CDRs of SEQ ID NOs:12, 13, and 48 and a humanized light chain comprising the three Kabat CDRs of SEQ ID NOs:15-17. In some such antibodies, a humanized heavy chain comprises the three Kabat CDRs of SEQ ID NO:12-14 and a humanized light chain comprises the three Kabat CDRs of SEQ ID NO:15-17.

The invention further provides humanized 1H7 antibodies in which the humanized heavy chain mature variable region shows at least 90%, 95%, 96%, 97%, 98%, or 99% identity or is 100% identity with SEQ ID NOs. 19, 21, 23, 25, and 27 and the humanized light chain mature variable region shows at least 90%, 95%, 96%, 97%, 98%, or 99% sequence identity to or is 100% identical with any one of SEQ ID NOs. 33, 35, 37, and 39.

Various permutations of the 11 variable region framework backmutations and 1 CDR mutation described above can be incorporated into the humanized 1H7 antibodies. In some such antibodies, position L46 is occupied by L or F (preferably F) and/or position L49 is occupied by Y or C (preferably C) and/or position L83 is occupied by F or A, and/or position H11 is occupied by V or L, and/or position H28 is occupied by T or S, and/or position H38 is occupied by R or K, and/or position H48 is occupied by M or I, and/or position H67 is occupied by V or A (preferably A), and/or position H69 is occupied by M or L, and/or position H71 is occupied by T or A (preferably A), and/or position H91 is occupied by Y or F, and/or position H28 is occupied by S or T, and/or position H97 is occupied by C or M or S or T (preferably C).

In some such antibodies, some or all of the backmutations in Hu1H7VLv1-v4 and Hu1H7VHv1-v5 are retained. Preferably, the backmutations at positions L46, H67, and H71 are retained. In other words, position L46 is occupied by F, position H67 is occupied by A, and position H71 is occupied by A. More preferably, the backmutations at positions L46, L49, H67, and H71 are retained. In other words, position L46 is occupied by F, position L49 is occupied by C, position H67 is occupied by A, and position H71 is occupied by A. In some antibodies, some or all of heavy chain positions H11, H28, H38, H48, H67, H69, H71, and/or H91 are occupied by L, S, K, I, A, L, A, and F respectively. Likewise in some antibodies some or all of light chain positions L46, L49 and/or L83 are occupied by F, C and A respectively. In some antibodies, 1, 2, 3, 4, 5, 6, 7, 8, 9 or all ten of positions H11, H28, H38, H48, H67, H69, H71, H91, L46, L49 and L83 is/are occupied by L, S, K, I, A, L, A, F, F, C and A respectively. In some antibodies, 0, 1, 2, 3, 4, 5, 6, or 7 positions are changed in the heavy chain mature variable region framework relative to SEQ ID NO:44, and 0, 1, 2, or 3 positions are change in the light chain mature variable region framework relative to SEQ ID NO:45. In some such antibodies, position H97 is occupied by C. Preferably, the humanized antibody has a $K_D$ for alpha-synuclein from about 0.5 to 2 of that of a murine or chimeric 1H7 antibody.

In some antibodies, position L46 is occupied by F, position H67 is occupied by A, position H71 is occupied by A, position H11 is occupied by V, and position H38 is occupied by R. In some such antibodies, position L49 is occupied by Y. More preferably, in some such antibodies, position L49 is occupied by C. In some such antibodies, position L83 is occupied by F. In some such antibodies, position L83 is occupied by A. In some such antibodies, position H97 is occupied by C. In some such antibodies, position H28 is occupied by T or S, position H48 is occupied by M, position H69 is occupied by M and position H91 is occupied by Y. In some such antibodies, position H28 is occupied by T or S, position H48 is occupied by M, position H69 is occupied by M and position H91 is occupied by F. In some such antibodies, position H28 is occupied by T or S, position H48 is occupied by M, position H69 is occupied by L and position H91 is occupied by Y. In some such antibodies, position H28 is occupied by T or S, position H48 is occupied by M, position H69 is occupied by L and position H91 is occupied by F. In some such antibodies, position H28 is occupied by T or S, position H48 is occupied by I, position H69 is occupied by M and position H91 is occupied by Y. In some such antibodies, position H28 is occupied by T or S, position H48 is occupied by I, position H69 is occupied by M and position H91 is occupied by F. In some such antibodies, position H28 is occupied by T or S, position H48 is occupied by I, position H69 is occupied by L and position H91 is occupied by Y. In some such antibodies, position H28 is occupied by T or S, position H48 is occupied by I, position H69 is occupied by L and position H91 is occupied by F. In some such antibodies, position H11 is occupied by L, and/or position H38 is occupied by K, and/or position H97 is occupied by S.

In any of the above antibodies, other amino acid substitutions can be made in the mature variable region framework, for example, in residues not in contact with the CDRs. Often the replacements made in the variant humanized sequences are conservative with respect to the replaced amino acids. In some antibodies, replacements relative to Hu1H7VLv1-v4 and Hu1H7VHv1-v5 (whether or not conservative) have no substantial effect on the binding affinity or potency of the resultant antibody relative to Hu1H7VLv1-v4 and Hu1H7VHv1-v5, that is, its ability to bind human alpha synuclein.

Variants typically differ from the heavy and light chain mature variable region sequences of Hu1H7VLv1-v4 and Hu1H7VHv1-v5 by a small number (e.g., typically no more than 1, 2, 3, 5 or 10 in either the light chain or heavy chain mature variable region framework, or both) of replacements, deletions or insertions.

C. Selection of Constant Region

The heavy and light chain variable regions of humanized antibodies can be linked to at least a portion of a human constant region. The choice of constant region depends, in part, whether antibody-dependent cell-mediated cytotoxicity, antibody dependent cellular phagocytosis and/or complement dependent cytotoxicity are desired. For example, human isotypes IgG1 and IgG3 have complement-dependent cytotoxicity and human isotypes IgG2 and IgG4 do not. Human IgG1 and IgG3 also induce stronger cell mediated effector functions than human IgG2 and IgG4. Light chain constant regions can be lambda or kappa. An exemplary human light chain kappa constant region has the amino acid sequence of SEQ ID NO:49. The N-terminal arginine of SEQ ID NO:49 can be omitted, in which case light chain kappa constant region has the amino acid sequence of SEQ ID NO:51. An exemplary human IgG1 heavy chain constant region has the amino acid sequence of SEQ ID NO:50. An exemplary human IgG2 heavy chain constant region has the amino acid sequence of SEQ ID NO:57. Antibodies can be expressed as tetramers containing two light and two heavy chains, as separate heavy chains, light chains, as Fab, Fab', F(ab')2, and Fv, or as single chain antibodies in which heavy and light chain mature variable domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype bind to a non-polymorphic region of a one or more other isotypes. Thus, for example, heavy chain constant regions can be of IgG1 G1m1 or IgG1 G1m3 allotypes and have the amino acid sequence of SEQ ID NO:52 or SEQ ID NO:55. Yet another heavy chain constant region has the amino acid sequence of SEQ ID NO:52 or SEQ ID NO:55 except that it lacks the C-terminal lysine.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004). Exemplary substitutions include a Gln at position 250 and/or a Leu at position 428 (EU numbering is used in this paragraph for the constant region) for increasing the half life of an antibody. Substitution at any or all of positions 234, 235, 236 and/or 237 reduce affinity for Fcγ receptors, particularly FcγRI receptor (see, e.g., U.S. Pat. No. 6,624,821). Some antibodies have alanine substitution at positions 234, 235 and 237 of human IgG1 for reducing effector functions. Optionally, positions 234, 236 and/or 237 in human IgG2 are substituted with alanine and position 235 with glutamine (see, e.g., U.S. Pat. No. 5,624,821).

In some antibodies, the light chain constant region has the amino acid sequence designated SEQ ID NO:49. In some antibodies, the heavy chain constant region has the amino acid sequence designated SEQ ID NO:52. Exemplary Hu1H7 light chains have SEQ ID NO:53 or SEQ ID NO:54. Exemplary Hu1H7 heavy chains have the amino acid sequence of SEQ ID NO:55 or SEQ ID NO:56. In some antibodies, the light chain is SEQ ID NO:53. In some antibodies, the heavy chain is SEQ ID NO:56.

D. Expression of Recombinant Antibodies

Antibodies can be produced by recombinant expression. Nucleic acids encoding the antibodies can be codon-optimized for expression in the desired cell-type (e.g., CHO or Sp2/0). Recombinant nucleic acid constructs typically include an expression control sequence operably linked to the coding sequences of antibody chains, including naturally-associated or heterologous promoter regions. The expression control sequences can be eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies. The vector or vectors encoding the antibody chains can also contain a selectable gene, such as dihydrofolate reductase, to allow amplification of copy number of the nucleic acids encoding the antibody chains.

*E. coli* is a prokaryotic host particularly useful for expressing antibodies, particularly antibody fragments. Microbes, such as yeast are also useful for expression. *Saccharomyces* is an example of a yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilizations.

Mammalian cells can be used for expressing nucleotide segments encoding immunoglobulins or fragments thereof. See Winnacker, From Genes to Clones, (VCH Publishers, NY, 1987). A number of suitable host cell lines capable of secreting intact heterologous proteins have been developed in the art, and include CHO cell lines, various COS cell lines, HeLa cells, HEK293 cells, L cells, and non-antibody-producing myelomas including Sp2/0 and NS0. It can be advantageous to use nonhuman cells. Expression vectors for these cells can include expression control sequences, such as an origin of replication, a promoter, an enhancer (Queen et al., Immunol. Rev. 89:49 (1986)), and necessary processing information sites, such as ribosome binding sites, RNA splice sites, polyadenylation sites, and transcriptional terminator sequences. Suitable expression control sequences are promoters derived from endogenous genes, cytomegalovirus, SV40, adenovirus, bovine papillomavirus, and the like. See Co et al., J. Immunol. 148:1149 (1992).

Having introduced vector(s) encoding antibody heavy and light chains into cell culture, cell pools can be screened for growth productivity and product quality in serum-free media. Top-producing cell pools can then be subjected to FACS-based single-cell cloning to generate monoclonal lines. Specific productivities above 50 pg or 100 pg per cell per day, which correspond to product titers of greater than 7.5 g/L culture, can be advantageous. Antibodies produced by single cell clones can also be tested for turbidity, filtration properties, PAGE, IEF, UV scan, HP-SEC, carboydrate-oligosaccharide mapping, mass spectrometery, and binding assay, such as ELISA or Biacore. A selected clone can then be banked in multiple vials and stored frozen for subsequent use.

Once expressed, antibodies can be purified according to standard procedures of the art, including protein A capture, column chromatography (e.g., hydrophobic interaction or ion exchange), low-pH for viral inactivation and the like (see generally, Scopes, Protein Purification (Springer-Verlag, NY, 1982)).

Methodology for commercial production of antibodies including codon optimization, selection of promoters, transcription elements, and terminators, serum-free single cell cloning, cell banking, use of selection markers for amplification of copy number, CHO terminator, serum free single cell cloning, improvement of protein titers (see, e.g., U.S. Pat. Nos. 5,786,464, 5,888,809, 6,063,598, 6,114,148, 7,569,339, WO2004/050884, WO2005/019442, WO2008/012142, WO2008/012142, WO2008/107388, and WO2009/027471, and).

E. Nucleic Acids

The invention further provides nucleic acids encoding any of the heavy and light chains described above. Typically, the nucleic acids also encode a signal peptide fused to the mature heavy and light chains (e.g., signal peptides having amino acid sequences of SEQ ID NOS: 29, 31 and 41 that can be encoded by SEQ ID NOS: 28, 30 and 40). Coding sequences on nucleic acids can be in operable linkage with regulatory sequences to ensure expression of the coding sequences, such as a promoter, enhancer, ribosome binding site, transcription termination signal and the like. The nucleic acids encoding heavy and light chains can occur in isolated form or can be cloned into one or more vectors. The nucleic acids can be synthesized by for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

V. Therapeutic Applications

The invention provides several methods of treating or effecting prophylaxis of Lewy Body disease in patients suffering from or at risk of such disease. Patients amenable to treatment include individuals at risk of disease of a LBD but not showing symptoms, as well as patients presently showing symptoms or the early warning signs of synucleinopathies, for example, EEG slowing, neuropsychiatric manifestations (depression, dementia, hallucinations, anxiety, apathy, anhedonia), autonomic changes (orthostatic hypotension, bladder disturbances, constipation, fecal incontinence, sialorrhea, dysphagia, sexual dysfunction, changes in cerebral blood flow), sensory changes (olfactory, pain, color discrimination abnormal sensations), sleep disorders (REM sleep behavior disorder (RBD), restless legs syndrome/periodic extremity movements, hypersomnia, insomnia) and miscellaneous other signs and symptoms (fatigue, diplopia, blurred vision, seborrhea, weight loss/gain). Therefore, the present methods can be administered prophylactically to individuals who have a known genetic risk of a LBD. Such individuals include those having relatives who have experienced this disease, and those whose risk is determined by analysis of genetic or biochemical markers. Genetic markers of risk toward PD include mutations in the alpha-synuclein or Parkin, UCHLI, and CYP2D6 genes; particularly mutations at positions 30 and 53 of the alpha-synuclein gene. Individuals presently suffering from Parkinson's disease can be recognized from its clinical manifestations including resting tremor, muscular rigidity, bradykinesia and postural instability.

In asymptomatic patients, treatment can begin at any age (e.g., 10, 20, 30). Usually, however, it is not necessary to begin treatment until a patient reaches 40, 50, 60 or 70. Treatment typically entails multiple dosages over a period of time. Treatment can be monitored by assaying antibody, or activated T-cell or B-cell responses to a therapeutic agent (e.g., a truncated form of alpha-synuclein peptide) over time. If the response falls, a booster dosage is indicated.

Antibodies can be used for treating or effecting prophylaxis of Lewy Body disease in patients by administration under conditions that generate a beneficial therapeutic response in a patient (e.g., reduction of neuritic and/or axonal alpha synuclein aggregates, reduction of neuritic dystrophy, improving cognitive function, and/or reversing, treating or preventing cognitive decline) in the patient. In some methods, the areas of neuritic dystrophy in the neuropil of neocortex and/or basal ganglia can be reduced by on average at least 10%, 20%, 30%, or 40% in treated patients compared with a control population.

Cognitive impairment, progressive decline in cognitive function, changes in brain morphology, and changes in cerebrovascular function are commonly observed in patients suffering from or at risk of Lewy Body disease. Administration of the present antibodies can inhibit or delay decline of cognitive function in such patients.

The invention also provides methods of preserving or increasing synaptic density and/or dentritic density. An index of changes in synaptic or dentritic density can be measured by markers of synapse formation (synaptophysin) and/or dendrites (MAP2). In some methods, the synaptic or dentritic density can be restored to the level of synaptic or dentritic density in a healthy subject. In some methods, the mean level of synaptic or dentritic density in treated patients can be elevated by 5%, 10%, 15%, 20%, 25%, 30% or more as compared to a population of untreated control patients.

VI. Pharmaceutical Compositions and Methods of Treatment

In prophylactic applications, an antibody or agent for inducing an antibody or a pharmaceutical composition the same is administered to a patient susceptible to, or otherwise at risk of a disease in a regime (dose, frequency and route of administration) effective to reduce the risk, lessen the severity, or delay the onset of at least one sign or symptom of the disease. In some prophylactic applications, the regime is effective to inhibit or delay accumulation of alpha synuclein and truncated fragments in the brain, and/or inhibit or delay its toxic effects and/or inhibit/or delay development of behavioral deficits. In therapeutic applications, an antibody or agent to induce an antibody is administered to a patient suspected of, or already suffering from a Lewy body disease in a regime (dose, frequency and route of administration) effective to ameliorate or at least inhibit further deterioration of at least one sign or symptom of the disease. In some therapeutic applications, the regime is effective to reduce or at least inhibit further increase of levels of alpha synuclein and truncated fragments, associated toxicities and/or behavioral deficits.

A regime is considered therapeutically or prophylactically effective if an individual treated patient achieves an outcome more favorable than the mean outcome in a control population of comparable patients not treated by methods of the invention, or if a more favorable outcome is demonstrated in treated patients versus control patients in a controlled clinical trial (e.g., a phase II, phase II/III or phase III trial) at the p<0.05 or 0.01 or even 0.001 level.

Effective doses vary depending upon many different factors, including means of administration, target site, physiological state of the patient including type of Lewy body disease, whether the patient is an ApoE carrier, whether the patient is human or an animal, other medications administered, and whether treatment is prophylactic or therapeutic.

An exemplary dosage range for antibodies is from about 0.01 to 5 mg/kg, and more usually 0.1 to 3 mg/kg or 0.15-2 mg/kg or 0.15-1.5 mg/kg, of patient body weight. Antibody can be administered such doses daily, on alternative days, weekly, fortnightly, monthly, quarterly, or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months.

Antibodies can be administered via a peripheral route (i.e., one in which an administered or induced antibody crosses the blood brain barrier to reach an intended site in the brain. Routes of administration include topical, intravenous, oral, subcutaneous, intraarterial, intracranial, intrathecal, intraperitoneal, intranasal or intramuscular. Some routes for administration of antibodies are intravenous and subcutaneous. This type of injection is most typically performed in the arm or leg muscles. In some methods, agents are injected directly into a particular tissue where deposits have accumulated, for example intracranial injection.

Pharmaceutical compositions for parenteral administration are can be sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use.

The present regimes can be administered in combination with another agent effective in treatment or prophylaxis of the disease being treated. For example, in the case of Parkinson's disease, immunotherapy against alpha synuclein WO/2008/103472, Levodopa, dopamine agonists, COMT inhibitors, MAO-B inhibitors, Amantadine, or anticholinergic agents can be used in combination with the present regimes.

VII. Other Applications

The antibodies described above can be used for detecting alpha-synuclein in the context of clinical diagnosis or treatment or in research. The antibodies can also be sold as research reagents for laboratory research in detecting cells bearing alpha-synuclein and their response to various stimuli. In such uses, monoclonal antibodies can be labeled with fluorescent molecules, spin-labeled molecules, enzymes or radioisotypes, and can be provided in the form of kit with all the necessary reagents to perform the assay for alpha-synuclein. The antibodies can also be used to purify alpha-synuclein, e.g., by affinity chromatography.

The antibodies can be used for detecting LBs in a patient. Such methods are useful to diagnose or confirm diagnosis of PD, or other disease associated with the presence of LBs in the brain, or susceptibility thereto. For example, the methods can be used on a patient presenting with symptoms of dementia. If the patient has LBs, then the patient is likely suffering from a Lewy body disease, such as Parkinson's disease. The methods can also be used on asymptomatic patients. Presence of Lewy bodies or other abnormal deposits of alpha-synuclein indicates susceptibility to future symptomatic disease. The methods are also useful for monitoring disease progression and/or response to treatment in patients who have been previously diagnosed with a Lewy body disease.

The methods can be performed by administering an antibody and then detecting the antibody after it has bound. If desired, the clearing response can be avoided by using an antibody fragment lacking a full-length constant region, such as a Fab. In some methods, the same antibody can serve as both a treatment and diagnostic reagent.

For diagnosis (e.g., in vivo imaging), the antibodies can be administered by intravenous injection into the body of the patient, or directly into the brain by intracranial injection or by drilling a hole through the skull. The dosage of reagent should be within the same ranges as for treatment methods. Typically, the antibody is labeled, although in some methods, the antibody is unlabeled and a secondary labeling agent is used to bind to the antibody. The choice of label depends on the means of detection. For example, a fluorescent label is suitable for optical detection. Use of paramagnetic labels is suitable for tomographic detection without surgical intervention. Radioactive labels can also be detected using PET or SPECT.

Diagnosis is performed by comparing the number, size and/or intensity of labeled loci to corresponding base line values. The base line values can represent the mean levels in a population of undiseased individuals. Base line values can also represent previous levels determined in the same patient. For example, base line values can be determined in a patient before beginning treatment, and measured values thereafter compared with the base line values. A decrease in values relative to base line signals a positive response to treatment.

The antibodies can be used to generate anti-idiotype antibodies. (see, e.g., Greenspan & Bona, FASEB J. 7(5): 437-444, 1989; and Nissinoff, J. Immunol. 147:2429-2438, 1991). Such anti-idiotype antibodies can be utilized in pharmacokinetics, pharmacodynamics, biodistribution studies as well as in studies of clinical human-anti-human antibody (HAHA) responses in individuals treated with the antibodies. For example, anti-idiotypic antibodies bind specifically the variable region of humanized 1H7 antibodies and therefore can be used to detect humanized 1H7 antibodies in pharmacokinetic studies and help to quantify human-anti-human antibody (HAHA) responses in treated individuals.

All patent filings, website, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Example I. Design of Humanized 1H7 Antibodies

The starting point or donor antibody for humanization is the mouse antibody 1H7 produced by the hybridoma having ATCC Accession No. PTA-8220 and described in U.S. patent application Ser. No. 11/710,248 published as US2009/0208487. The complete heavy chain variable amino acid and nucleic acid sequences of m1H7 are provided as SEQ ID NOS:4 and 5, respectively. The complete light chain variable amino acid and nucleic acid sequences of m1H7 are provided as SEQ ID NOS:6 and 7, respectively. The heavy chain variable amino acid and nucleic acid sequences of mature m1H7 are provided as SEQ ID NOS:8 and 9, respectively. The light chain variable amino acid and nucleic acid sequences of mature m1H7 are provided as SEQ ID NOS:10 and 11, respectively. The heavy chain CDR1, CDR2, and CDR3 amino acid sequences are provided as SEQ ID NOS:12, 13, and 14, respectively. The light chain CDR1, CDR2, and CDR3 amino acid sequences are provided as SEQ ID NOS:15, 16, and 17, respectively. Kabat numbering is used throughout in this Example.

The variable kappa (Vk) of m1H7 belongs to mouse Kabat subgroup 3 which corresponds to human Kabat subgroup 1. The variable heavy (Vh) of 1H7 belongs to mouse Kabat subgroup 5a which corresponds to human Kabat subgroup 1 (Kabat et al. Sequences of Proteins of Immunological Interest, Fifth Edition. NIH Publication No. 91-3242, 1991). The 15 residue CDR-L1 belongs to canonical class 5 (note that the Methionine at position 33 is usually Leucine in this class), the 7 residue CDR-L2 belongs to canonical class 1, the 9 residue CDR-L3 belongs to canonical class 1 in Vk (Martin & Thornton, J Mol Biol. 263:800-15, 1996). The 5 residue CDR-H1 belongs to canonical class 1, the 17 residue CDR-H2 belongs to canonical class 2 (Martin & Thornton, J Mol Biol. 263:800-15, 1996). The CDR-H3 has no canonical classes, but the 8 residue loop probably has a kinked base according to the rules of Shirai et al., FEBS Lett. 455:188-97 (1999).

The residues at the interface between the Vk and Vh domains are the ones commonly found, except that F46 in the kappa chain is usually a Leucine. This makes this position a candidate t for backmutation. A search was made over the protein sequences in the PDB database (Deshpande et al., Nucleic Acids Res. 33: D233-7, 2005) to find structures which would provide a rough structural model of 1H7. The 0.5B anti-HIV antibody has good overall sequence similarity to 1H7 Vk, retaining the same canonical structures for the loops. The NMR structure of the 0.5B anti-HIV antibody (pdb code 1QNZ; Tugarinov et al., Structure 8:385-95, 2000) was used for the Vk structure in the modeling. The anti-alpha-(2→8)-polysialic acid antibody has good overall sequence similarity to 1H7 Vh structure. It also has a CDR-H3 of a similar length with a kinked base. The structure of the anti-alpha-(2→8)-polysialic acid antibody (1PLG; Evans et al., Biochemistry 34:6737-44, 1995) has reasonable resolution (2.8A), and was used for the Vh structure in the modeling. In addition, CDRs-H1 and H2 of the anti-alpha-(2→8)-polysialic acid antibody have the same canonical structures as 1H7 Vh. DeepView/Swiss-PdvViewer 3.7 (SP5) (Guex & Peitsch, Electrophoresis 18: 2714-2723, 1997) was used to model a rough structure of 1H7fv.

A search of the non-redundant protein sequence database from NCBI allowed selection of suitable human frameworks into which to graft the murine CDRs. For Vk, a human kappa light chain with NCBI accession code AAY33358 (GI:63102905; SEQ ID NO:43) (Kramer et al., Eur J Immunol. 35:2131-45, 2005) was chosen. This has the same canonical classes for CDR-L2 and L3, and belongs to human kappa germline A30, a member of Kabat human kappa subgroup 1. AAY33358 has a sequence identity of 65.4% in the light chain variable region framework to murine 1H7 light chain. For Vh, human Ig heavy chain BAC02037 (GI:21670055; SEQ ID NO:42) was chosen, belonging to human heavy germline VH1-18. It is a member of Kabat human heavy subgroup 1. It shares the canonical form of 1H7 CDR-H1 and H2, and H3 is 8 residues long with a predicted kinked base. BAC02037 has a sequence identity of 65.8% in the variable region framework to murine 1H7 heavy chain. Humanized 1H7 heavy and light chain variable sequences having no backmutations or CDR mutations are provided as SEQ ID NOS:44-45.

Four humanized light chain variable regions variants and five humanized heavy chain variable region variants were constructed containing different permutations of the above substitutions (Hu1H7VLv1-v4; SEQ ID NOs:32-39, and Hu1H7VHv1-v5; SEQ ID NOs:18-27 respectively) (FIGS. 1-2 and Table 1). SEQ ID NOs. 19, 21, 23, 25, 27, 33, 35, 37, and 39 include backmutations as shown in Table 1. In addition, two humanized heavy chains (SEQ ID NOs: 25, 27) include C→S mutation at position H97 (Kabat numbering) of heavy chain CDR3 (FIGS. 1-2 and Table 1). The amino acids at L46, L49, L83, H11, H28, H38, H48, H67, H69, H71, H91, and H97 in Hu1H7VLv1-v4 and Hu1H7VHv1-v5 are listed in Table 2.

The H3L3 variant (hu1H7VHv3 (SEQ ID NO:23)-Hu1H7VLv3 (SEQ ID NO:37) was found to give the lowest dissociation constant (highest association constant), the same as the mouse 1H7 within the SEM.

TABLE 1

$V_H$, $V_L$ backmutations, and CDR mutations

| $V_H$ variant | $V_H$ exon acceptor sequence | donor framework residues | CDR mutations |
|---|---|---|---|
| Hu1H7VHv1 (SEQ ID NO: 19) | NCBI accession code BAC02037 | H11, H28, H38, H48, H67, H69, H71, H91 | |
| Hu1H7VHv2 (SEQ ID NO: 21) | NCBI accession code BAC02037 (SEQ ID NO: 42) | H28, H48, H67, H69, H71, H91 | |
| Hu1H7VHv3 (SEQ ID NO: 23) | NCBI accession code BAC02037 (SEQ ID NO: 42) | H67, H71 | |
| Hu1H7VHv4 (SEQ ID NO: 25) | NCBI accession code BAC02037 (SEQ ID NO: 42) | H28, H48, H67, H69, H71, H91 | H97 |
| Hu1H7VHv5 (SEQ ID NO: 27) | NCBI accession code BAC02037 (SEQ ID NO: 42) | H67, H71 | H97 |

| VL variant | VL exon acceptor sequence | donor framework residues |
|---|---|---|
| Hu1H7VLv1 (SEQ ID NO: 33) | NCBI accession code AAY33358 (SEQ ID NO: 43) | L46, L49, L83 |
| Hu1H7VLv2 (SEQ ID NO: 35) | NCBI accession code AAY33358 (SEQ ID NO: 43) | L46, L83 |
| Hu1H7VLv3 (SEQ ID NO: 37) | NCBI accession code AAY33358 (SEQ ID NO: 43) | L46, L49 |
| Hu1H7VLv4 (SEQ ID NO: 39) | NCBI accession code AAY33358 (SEQ ID NO: 43) | L46 |

TABLE 2

Kabat numbering of some framework residues for backmutation and CDR mutations in humanized 1H7 antibodies

| | AAY33358 light chain | BAC02037 heavy chain | Mouse 1H7 | Hu1H7 VH1 | Hu1H7 VH2 | Hu1H7 VH3 | Hu1H7 VH4 | Hu1H7 VH5 | Hu1H7 VL1 | Hu1H7 VL2 | Hu1H7 VL3 | Hu1H7 VL4 |
|---|---|---|---|---|---|---|---|---|---|---|---|---|
| H11 | — | V | L | L | V | V | V | V | — | — | — | — |
| H28 | — | T | S | S | S | T | S | T | — | — | — | — |
| H38 | — | R | K | K | R | R | R | R | — | — | — | — |
| H48 | — | M | I | I | I | M | I | M | — | — | — | — |
| H67 | — | V | A | A | A | A | A | A | — | — | — | — |
| H69 | — | M | L | L | L | M | L | M | — | — | — | — |
| H71 | — | T | A | A | A | A | A | A | — | — | — | — |
| H91 | — | Y | F | F | F | Y | F | Y | — | — | — | — |
| H97 | — | G | C | C | C | C | S | S | — | — | — | — |
| L46 | L | — | F | — | — | — | — | — | F | F | F | F |
| L49 | Y | — | C | — | — | — | — | — | C | Y | C | Y |
| L83 | F | — | A | — | — | — | — | — | A | A | F | F |

The rationales for selection of the above positions as candidates for substitution are as follows.

L46F (here as elsewhere for framework backmutations, the first mentioned residue is the human residue and the second the mouse residue): This position is a Vk/Vh interface residues.

Y49C: Cysteine at this position is unusual in either mouse or human sequence. Occupying a position in the center of the antigen-binding site, this residue may bind antigen, or maintain the conformation of the loops.

F83A: In human framework, this position is occupied by phenylalanine, a larger amino acid. Therefore, A83 would be unusual in human frameworks. In the humanized antibody, so the constant domain will be human not mouse, so the human F83 would be usual. However, this position in Vk is in close proximity to the constant domain and may interfere with packing against the constant region. Therefore, it would be interesting to backmutate it to A to see if there is a difference.

V11L: This position contacts the constant domain and may therefore alter the topography of the binding site.

T28S: This position contributes to CDR-H1 conformation, but may also bind antigen. The T→S mutation is a conservative mutation.

R38K: This position lies beneath CDR-H2, interacting with F63 in the model. The R→K mutation is a conservative mutation.

M48I: This position lies beneath F63 in CDR-H2 in the model. The M→I mutation is a conservative mutation.

V67A: This position lies underneath CDR-H2. The V→A mutation is not a conservative mutation.

M69L: This position lies beneath CDR-H2. The M→L mutation is a conservative mutation.

T71A: This position is a canonical residue for CDR-H2. The T→A mutation is not a conservative mutation.

Y91F: This position is an interface residue interacting with P44 in the light chain. The Y→F mutation is a conservative mutation.

C97S: This CDR mutation in CDRH3 avoids posttranslational modification of the cysteine.

>Hu1H7Vκ Version1

(SEQ ID NO: 33)
DIQLTQSPSSLSASVGDRVTITCKASQSVDYDGDSYMNWYQQKPGK

APKFLICAASNLESGVPSRFSGSGSGTDFTLTISSLQPEDAATYYC

QQSNEDPFTFGQGTKLEIK

>Hu1H7Vκ Version2

(SEQ ID NO: 35)
DIQLTQSPSSLSASVGDRVTITCKASQSVDYDGDSYMNWYQQKPGK

APKFLIYAASNLESGVPSRFSGSGSGTDFTLTISSLQPEDAATYYC

QQSNEDPFTFGQGTKLEIK

>Hu1H7Vκ Version3

(SEQ ID NO: 37)
DIQLTQSPSSLSASVGDRVTITCKASQSVDYDGDSYMNWYQQKPGK

APKFLICAASNLESGVPSRFSGSGSGTDFTLTISSLQPEDFATYYC

QQSNEDPFTFGQGTKLEIK

>Hu1H7Vκ Version4

(SEQ ID NO: 39)
DIQLTQSPSSLSASVGDRVTITCKASQSVDYDGDSYMNWYQQKPGK

APKFLIYAASNLESGVPSRFSGSGSGTDFTLTISSLQPEDFATYYC

QQSNEDPFTFGQGTKLEIK

>Hu1H7vh Version1

(SEQ ID NO: 19)
QVQLVQSGAELKKPGASVKVSCKASGYSFTSYYIHWVKQAPGQGLE

WIGWIYPGSGNTKYSEKFKGRATLTADTSTSTAYMELRSLRSDDTA

VYFCARDGCYGFAYWGQGTLVTVSS

>Hu1H7vh Version2

(SEQ ID NO: 21)
QVQLVQSGAEVKKPGASVKVSCKASGYSFTSYYIHWVRQAPGQGLE

WIGWIYPGSGNTKYSEKFKGRATLTADTSTSTAYMELRSLRSDDTA

VYFCARDGCYGFAYWGQGTLVTVSS

>Hu1H7vh Version3

(SEQ ID NO: 23)
QVQLVQSGAEVKKPGASVKVSCKASGYTFTSYYIHWVRQAPGQGLE

WMGWIYPGSGNTKYSEKFKGRATMTADTSTSTAYMELRSLRSDDTA

VYYCARDGCYGFAYWGQGTLVTVSS

>Hu1H7vh Version4

(SEQ ID NO: 25)
QVQLVQSGAEVKKPGASVKVSCKASGYSFTSYYIHWVRQAPGQGLE

WIGWIYPGSGNTKYSEKFKGRATLTADTSTSTAYMELRSLRSDDTA

VYFCARDGSYGFAYWGQGTLVTVSS

>Hu1H7vh Version5

(SEQ ID NO: 27)
QVQLVQSGAEVKKPGASVKVSCKASGYTFTSYYIHWVRQAPGQGLEWM

GWIYPGSGNTKYSEKFKGRATMTADTSTSTAYMELRSLRSDDTAVYYC

ARDGSYGFAYWGQGTLVTVSS

Example II. Binding Kinetic Analysis of Murine, Chimeric, and Humanized 1H7 Antibodies Binding kinetics of humanized 1H7 antibodies comprising a heavy chain selected from Hu1H7VHv1-5 and a light chain selected from Hu1H7VLv1-4 have been characterized.

Figure 3B:
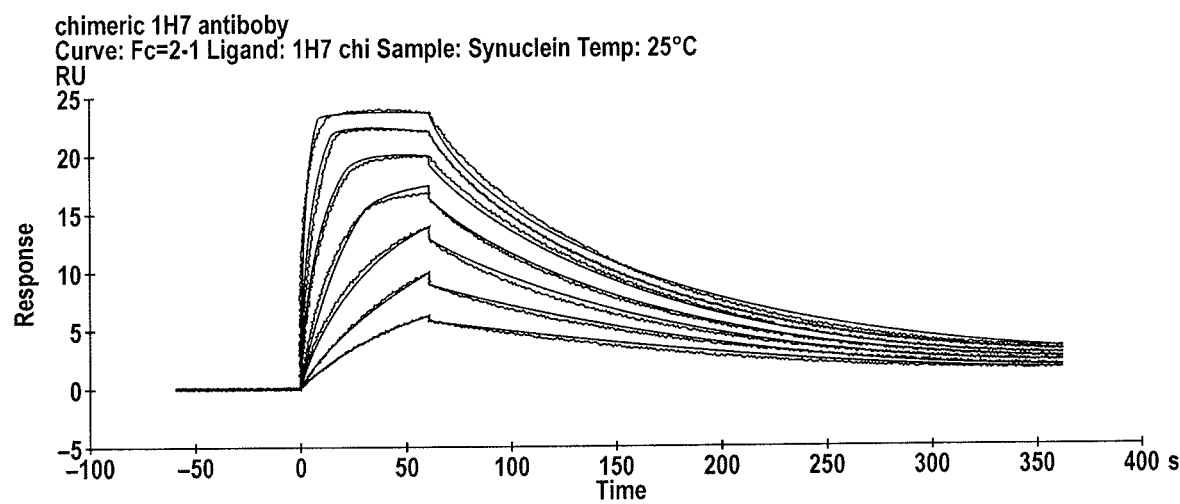
Figure 3C:
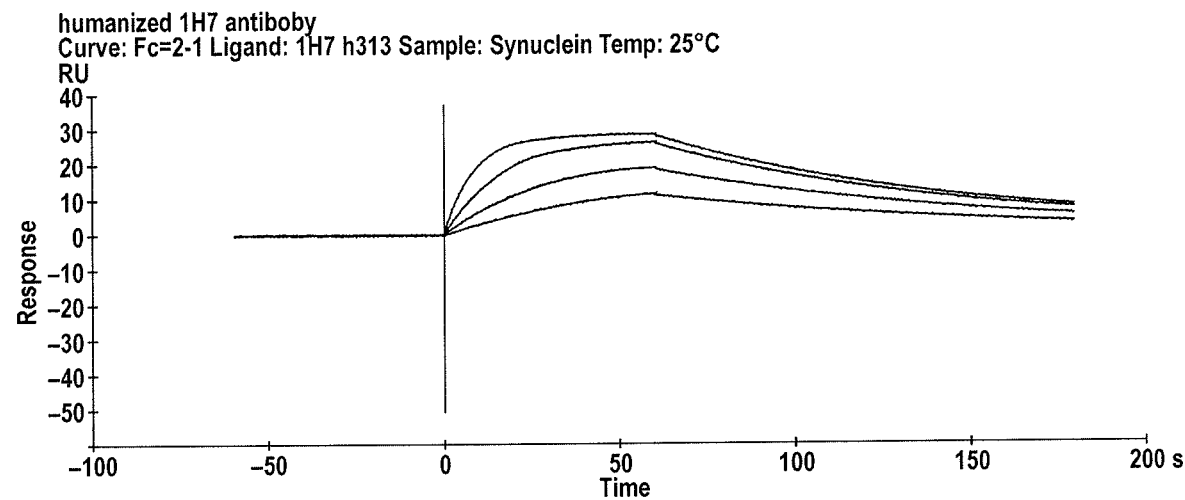
Figure 5B:
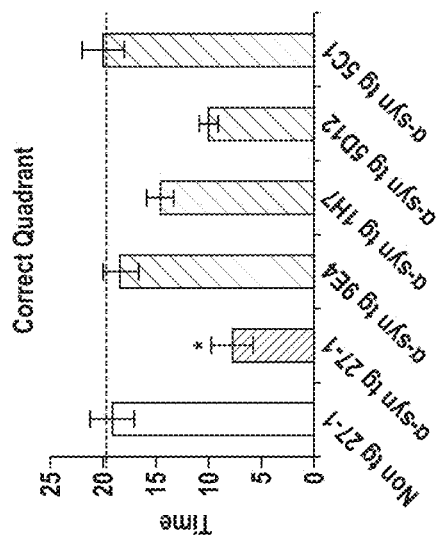
FIGS. 5A-B shows the results of passive immunotherapy with 1H7 on memory performance in the Morris water maze test.
Figure 5A:
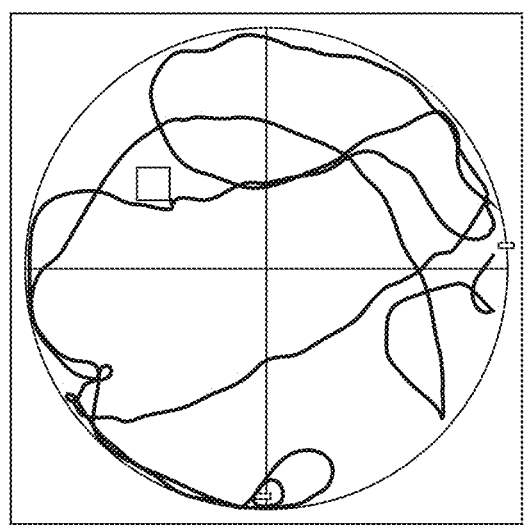

Biacore full binding kinetic analysis of antibodies were carried out using Biacore. Detailed binding kinetic parameters (association rate, ka, dissociation rate, kd, and affinity constant, KD) were determined for murine 1H7 (FIG. 3A), chimeric 1H7 (FIG. 3B) and humanized 1H7 (Hu1H7VHv3-Hu1H7VLv3, Hu1H7VHv3-Hu1H7VLv1, Hu1H7VHv4-Hu1H7VLv1) antibodies (FIG. 3C). Binding kinetic parameters of humanized 1H7, in particular Hu1H7VHv3-Hu1H7VLv3, are comparable to those of murine 1H7.

TABLE 3

Binding kinetic parameters of murine 1H7, chimeric 1H7 and humanized 1H7 (Hu1H7VHv3-Hu1H7VLv3, Hu1H7VHv3-Hu1H7VLv1, Hu1H7VHv4-Hu1H7VLv1)

| Antibody | ka (1/Ms) | kd (1/s) | $K_D$ (nM) |
|---|---|---|---|
| Murine 1H7 | 1.0e6 | 9.6e-3 | 9.5 |
| Chimeric 1H7 | 1.7e6 | 1.3e-2 | 7.4 |
| Humanized 1H7 H3L3 (Hu1H7VHv3-Hu1H7VLv3) | 1.3e6 | 1.1e-2 | 9.0 |
| Humanized 1H7 H3L1 (Hu1H7VHv3-Hu1H7VLv1) | 1.1e6 | 1.3e-2 | 12 |
| Humanized 1H7 H4L1 (Hu1H7VHv4-Hu1H7VLv1) | 9.7e5 | 3.3e-2 | 33.9 |
| Humanized 1H7 H5L1 (Hu1H7VHv5-Hu1H7VLv1) | 8.8e5 | 5.6e-2 | 64.0 |
| Humanized 1H7 H4L4 (Hu1H7VHv4-Hu1H7VLv4) | N/A * | N/A * | N/A * |

* The binding kinetic parameters could not be determined for Hu1H7VHv4-Hu1H7VLv4 at concentrations comparable to those used in the analysis for other humanized 1H7 antibodies or murine/chimeric 1H7.

Binding kinetic of humanized 1H7 antibodies were also measured by bio-layer interferometry (BLI) using a ForteBio Octet QK instrument (ForteBio, Menlo Park, Calif.). Detailed binding kinetic parameters (association rate, apparent ka, dissociation rate, apparent kd, and affinity constant, apparent KD) were determined for chimeric 1H7 and various humanized 1H7 antibodies (Tables 6-7, FIGS. 4A-C). Apparent ka, apparent kd and apparent $K_D$ are binding kinetic parameters obtained using ForteBio assay formats. These parameters differ from ka, kd and $K_D$ measured using Biocore assays due to, e.g., avidity effects associated with ForteBio assay formats.

TABLE 4

Binding kinetic parameters of chimeric 1H7
and humanized 1H7 (Hu1H7VHv1-Hu1H7VLv1,
Hu1H7VHv1-Hu1H7VLv2, Hu1H7VHv1-Hu1H7VLv3,
Hu1H7VHv1-Hu1H7VLv4, Hu1H7VHv2-Hu1H7VLv1,
Hu1H7VHv2-Hu1H7VLv2)

| Antibody | Apparent ka (1/Ms) | Apparent kd (1/s) | Apparent $K_D$ (nM) |
|---|---|---|---|
| Chimeric 1H7 | 4.7e5 | 1.1e−6 | 2.3e−3 |
| Humanized 1H7 H1L1 (Hu1H7VHv1-Hu1H7VLv1) | 2.5e5 | 1.2e−3 | 4.8 |
| Humanized 1H7 H1L2 (Hu1H7VHv1-Hu1H7VLv2) | 1.6e6 | 9e−3 | 5.8 |
| Humanized 1H7 H1L3 (Hu1H7VHv1-Hu1H7VLv3) | 2.2e5 | 6.4e−4 | 2.9 |
| Humanized 1H7 H1L4 (Hu1H7VHv1-Hu1H7VLv4) | 1.8e6 | 5.8e−3 | 3.3 |
| Humanized 1H7 H2L1 (Hu1H7VHv2-Hu1H7VLv1) | 5.8e5 | 4.2e−6 | 7.2e−3 |
| Humanized 1H7 H2L2 (Hu1H7VHv2-Hu1H7VLv2) | 2.3e6 | 4.6e−3 | 2 |

TABLE 5

Binding kinetic parameters of chimeric 1H7
and humanized 1H7 (Hu1H7VHv4-Hu1H7VLv2,
Hu1H7VHv4-Hu1H7VLv3, Hu1H7VHv4-Hu1H7VLv4,
Hu1H7VHv5-Hu1H7VLv2, Hu1H7VHv5-Hu1H7VLv3,
Hu1H7VHv5-Hu1H7VLv4)

| Antibody | Apparent ka (1/Ms) | Apparent kd (1/s) | Apparent $K_D$ (nM) |
|---|---|---|---|
| Chimeric 1H7 | 8.3e5 | 8.7e−4 | 1.0 |
| Humanized 1H7 H4L2 (Hu1H7VHv4-Hu1H7VLv2) | 1.2e6 | 2.1e−3 | 1.7 |
| Humanized 1H7 H4L3 (Hu1H7VHv4-Hu1H7VLv3) | 7.4e5 | 2.0e−3 | 2.7 |
| Humanized 1H7 H4L4 (Hu1H7VHv4-Hu1H7VLv4) | 5.2e5 | 2.3e−3 | 4.4 |
| Humanized 1H7 H5L2 (Hu1H7VHv5-Hu1H7VLv2) | 5.2e5 | 2.1e−3 | 4.0 |
| Humanized 1H7 H5L3 (Hu1H7VHv5-Hu1H7VLv3) | 7.6e5 | 2.0e−3 | 2.6 |
| Humanized 1H7 H5L4 (Hu1H7VHv5-Hu1H7VLv4) | 1.6e6 | 1.9e−3 | 1.2 |

Humanized 1H7 antibodies, in particular Hu1H7VHv3-Hu1H7VLv3 and Hu1H7VHv3-Hu1H7VLv1, exhibited staining patterns of various regions (e.g., striatum, pyramidal cell layer, cortex, substantia nigra) of transgenic or non-transgenic mouse brain similar to those of murine 1H7.

Example II. Passive Immunization with α-Synuclein Antibodies

The goal of this experiment is to determine effectiveness of α-synuclein antibodies in in vitro and in vivo studies as well as behavioral assays. We used α-synuclein transgenic (Line 61), α-synuclein knockout and wildtype female mice, 3-4 months old at initiation and n=14/group. Antibodies tested included 9E4 (IgG1, epitope: amino acids 118-126 of alpha synuclein), 5C1 (IgG1, epitope: amino acids 118-126 of alpha synuclein, c-linker), 5D12, IgG2 (SN118-126), 1H7, IgG1 (SN 91-99) and an IgG1 control antibody 27-1. Mice received a dosage of 10 mg/kg over a 5 month period, for a total of 21 injections. In addition, the animals were injected with lentivirus (LV) expressing human α-synuclein (wt) by unilateral introduction of human α-synuclein (wt) into the hippocampus.

Readout antibodies include those from Chemicon (epitope: full-length alpha synuclein), Millipore (epitope: full-length alpha synuclein), and Neotope, ELADW 105 (epitope: amino acids 121-124 of full-length alpha synuclein).

Endpoints: Antibody titers were measured during the in life phase. Behavioral assays include Morris Water Maze test (MWW) and horizontal beam test. The round beam test is a test of motor balance, coordination and gait conducted using two beams of varying diameter. Beam A is the larger diameter (easier, considered the training beam) and Beam D is the smaller diameter (more difficult, considered the testing beam). Data is presented as "errors" (number of slips/10 cm) and "speed" (time taken to travel 10 cm/sec). Water maze performance was carried out at weeks 10 and termination. The following neuropathology measurements were taken: alpha synuclein aggregation, synaptophysin, and MAP2. The following biochemistry measurements were taken: alpha synuclein, PSD95, synaptophysin. Selected multilabeling and confocal labeling were carried out using synaptic, neuronal and glial markers.

The results showed that all antibodies, except 5D12, produced significant reduction in α-syn accumulation and preservation of synaptic and dendritic densities, as well as positive outcomes in MWM performance. The 9E4 antibody is effective in in vitro and in vivo studies as well as behavioral assays. Readouts indicate antibody may reduce neuritic/axonal alpha synuclein aggregates.

Figure 6B:
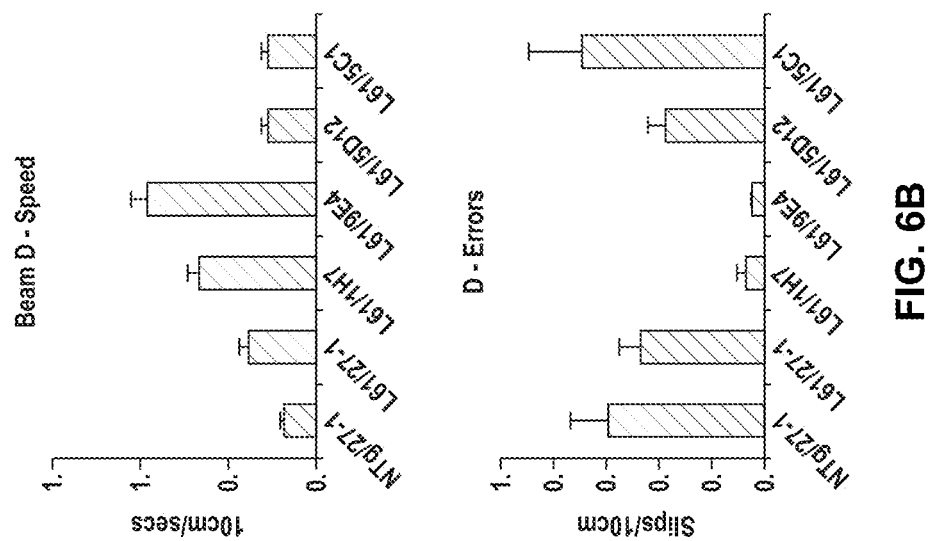
FIGS. 6A-B shows the results of passive immunotherapy with 1H7 on speed and errors in the round beam test.
Figure 6A:
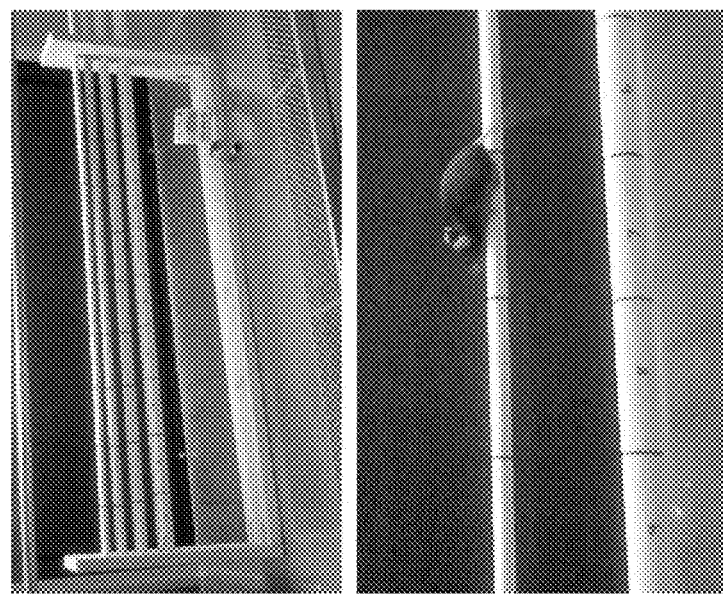

Behavioral Results:

The 1H7 antibody (as well as 9E4 and 5C1 antibodies) improved water maze performance in α-synuclein transgenic mice, whereas 5D12 did not. The 9E4 and 1H7 antibodies improved performance on the beam test as measured both by speed and errors, whereas the 5D12 and 5C1 antibodies did not (FIG. 6).

Neuropathology Results:

The 9E4, 1H7 and 5C1 antibodies reduced ELADW-105 positive neuritic dystrophy, whereas the 5D12 antibody did not. In alpha synuclein transgenic mice, the 9E4 antibody reduced the area of neuropil by 43% in neocortex and by 40% in basal ganglia as compared to control. The 9E4 antibody also preserved synaptophysin and MAP2 in neocortex and basal ganglia.

DEPOSIT

The following monoclonal antibody-producing cell lines have been deposited under the provisions of the Budapest Treaty with the American Type Culture Collection (ATCC, P.O. Box 1549, Manassas, Va. 20108) on the dates indicated:

| Monoclonal antibody | Cell Line | Epitope/Specificity | Isotype | Date of Deposit | Accession No. |
|---|---|---|---|---|---|
| 1H7 | JH17.1H7.4.24.34 | alpha-synuclein residues 91-99 | IgG1 | Feb. 26, 2007 | PTA-8220 |

It will be apparent to one of ordinary skill in the art that many changes and modifications can be made thereto without departing from the spirit or scope of the appended claims. Unless otherwise apparent from the context, any step, feature, embodiment, or aspect can be used in combination with any other. All publications and patent applications mentioned in this specification are herein incorporated by reference to the same extent as if each individual publication or patent application was specifically and individually indicated to be incorporated by reference.

SEQUENCE LISTING

SEQ ID NO: 1 Natural human wildtype alpha-synuclein
MDVFMKGLSKAKEGVVAAAEKTKQGVAEAAGKTKEGVLYVGSKTKEGVV

HGVATVAEKTKEQVTNVGGAVVTGVTAVAQKTVEGAGSIAAATGFVKKD

QLGKNEEGAPQEGILEDMPVDPDNEAYEMPSEEGYQDYEPEA

SEQ ID NO: 2 Non-amyloid component (NAC) domain of alpha-synuclein as reported by Jensen et al.
EQVTNVGGAVVTGVTAVAQKTVEGAGSIAAATGFV SEQ ID NO: 3 Non-amyloid component (NAC) domain of alpha-synuclein as reported by Uéda et al.
KEQVTNVGGAVVTGVTAVAQKTVEGAGS SEQ ID NO: 4 m1H7 antibody heavy chain variable nucleotide sequence (signal peptide underlined; CDRs shown in bold and underlined)
<u>ATGGGATGGAGCTGGGTCTTTATCTTCCTCCTGTCAGGAACTGCAGG</u>

<u>TGTCCATTGCC</u>CAGGTCCAGCTGCAGCAGTCTGGACCTGAGCTGGTGA

AGCCTGGGACTTCAGTGAAGATATCCTGCAAGGCTTCTGGCTACAGC

TTCACA<u>AGCTACTATATACA</u>CTGGGTGAAGCAGAGTCCTGGACAGGG

ACTTGAGTGGATTGGA<u>TGGATTTATCCTGGAAGTGGTAATACTAAGT</u>

<u>ACAGTGAGAAGTTCAAGGGC</u>AAGGCCACACTGACTGCAGACACATCC

TCCAGCACAGCCTACATGCAGCTCAGCAGCCTGACATCTGAGGACTC

TGCAGTCTATTTCTGTGCAAGA<u>GATGGTTGCTACGGGTTTGCTTACT</u>

GGGGCCAAGGGACTCTGGTCACTGTCTCT

SEQ ID NO: 5 m1H7 antibody heavy chain variable aa sequence (signal peptide underlined; CDRs shown in bold and underlined)
<u>MGWSWVFIFLLSGTAGVHC</u>QVQLQQSGPELVKPGTSVKISCKASGYS FT<u>SYYIH</u>WVKQSPGQGLEWIG<u>WIYPGSGNTKYSEFKFKG</u>KATLTADTS SSTAYMQLSSLTSEDSAVYFCAR<u>DGCYGFAY</u>WGQGTLVTVS SEQ ID NO: 6 m 1H7 antibody light chain variable nucleotide sequence (signal peptide underlined; CDRs shown in bold and underlined)
<u>ATGGAGACAGACACACTCCTGTTATGGGTGCTGCTGCTCTGGGTTCCA</u>

<u>GGCTCCACTGGTG</u>ACATGTGCTGACCCAATCTCCAGCTTCTTTGGCTG

TGTCTCTAGGGCAGAGGGCCACCATCTCCTGC<u>AAGGCCAGCCAAAGTG</u>

<u>TTGATTATGATGGTGATAGTTATATGAAC</u>TGGTACCAACAGAAACCAG

GACAGCCACCCAAATTCCTCATCTG<u>TGCTGCATCCAATCTAGAATCT</u>G

GGATCCCAGCCAGGTTTAGTGGCAGTGGGTCTGGGACAGACTTCACCC

TCAACATCCATCCTGTGGAGGAGGAGGATGCTGCAACCTATTACTGT<u>C</u>

<u>AGCAAAGTAATGAGGATCCATTCACG</u>TTCGGCTCGGGGACAAAGTTGG

AAATAAAA

SEQ ID NO: 7 m1H7 antibody light chain variable aa sequence (signal peptide underlined; CDRs shown in bold and underlined)
<u>METDTLLLWVLLLWVPG</u>STGDIVLTQSPASLAVSLGQRATISC<u>KASQSV</u>

<u>DYDGDSYMN</u>WYQQKPGQPPKFLI<u>CAASNLES</u>GIPARFSGSGSGTDFTLN

IFIPVEEEDAATYYC<u>QQSNEDPFT</u>FGSGTKLEIK

SEQ ID NO: 8 mature m1H7 antibody heavy chain variable nucleotide sequence (CDRs shown in bold and underlined)
GTCCAGCTGCAGCAGTCTGGACCTGAGCTGGTGAAGCCTGGGACTTCAG TGAAGATATCCTGCAAGGCTTCTGGCTACAGCTTCACA<u>AGCTACTATAT</u>

<u>ACA</u>CTGGGTGAAGCAGAGTCCTGGACAGGGACTTGAGTGGATTGGA<u>TGG</u>

<u>ATTTATCCTGGAAGTGGTAATACTAAGTACAGTGAGAAGTTCAAGGGC</u>A

AGGCCACACTGACTGCAGACACATCCTCCAGCACAGCCTACATGCAGCT

CAGCAGCCTGACATCTGAGGACTCTGCAGTCTATTTCTGTGCAAGA<u>GAT</u>

<u>GGTTGCTACGGGTTTGCTTAC</u>TGGGGCCAAGGGACTCTGGTCACTGTCT

CT

SEQ ID NO:9 mature m1H7 antibody heavy chain variable aa sequence (CDRs shown in bold and underlined)
VQLQQSGPELVKPGTSVKISCKASGYSFT<u>SYYIH</u>WVKQSPGQGLEWIG

<u>WIYPGSGNTKYSEKFK</u>GKATLTADTSSSTAYMQLSSLTSEDSAVYFCA

R<u>DGCYGFAY</u>WGQGTLVTVS

SEQ ID NO: 10 mature m1H7 antibody light chain variable nucleotide sequence (CDRs shown in bold and underlined)
GACATTGTGCTGACCCAATCTCCAGCTTCTTTGGCTGTGTCTCTAGG GCAGAGGGCCACCATCTCCTGC<u>AAGGCCAGCCAAAGTGTTGATTATG</u>

<u>ATGGTGATAGTTATATGAAC</u>TGGTACCAACAGAAACCAGGACAGCCA

CCCAAATTCCTCATCTGT<u>GCTGCATCCAATCTAGAATCT</u>GGGATCCC

AGCCAGGTTTAGTGGCAGTGGGTCTGGGACAGACTTCACCCTCAACA

TCCATCCTGTGGAGGAGGAGGATGCTGCAACCTATTACTGT<u>CAGCAA</u>

<u>AGTAATGAGGATCCATTCACG</u>TTCGGCTCGGGGACAAAGTTGGAAAT

AAAA

SEQ ID NO: 11 mature m1H7 antibody light chain variable aa sequence (CDRs shown in bold and underlined)
DIVLTQSPASLAVSLGQRATISCKASQSVDYDGDSYMNWYQQKPGQPPKFLIAASNLESGIPARFSGSGSGTDFTLNIHPVEEEDAATYYCQQSNEDPFTFGSGTKLEIK SEQ ID NO: 12 m1H7 antibody heavy chain CDR1 (Kabat definition)
SYYIH

SEQ ID NO: 13 m1H7 antibody heavy chain CDR2 (Kabat definition)
WIYPGSGNTKYSEKFKG

SEQ ID NO: 14 m1H7 antibody heavy chain CDR3 (Kabat definition)
DGCYGFAY m1H7 antibody light chain CDR1 (Kabat definition)
SEQ ID NO: 15
KASQSVDYDGDSYMN m1H7 antibody light chain CDR2 (Kabat definition)
SEQ ID NO: 16
AASNLES m1H7 antibody light chain CDR3 (Kabat definition)
SEQ ID NO: 17
QQSNEDPFT

Hu1H7VHv1 (nucleotide seq)
SEQ ID NO: 18
CAGGTGCAGCTGGTGCAGTCCGGCGCCGAGCTGAAGAAGCCCGGCGCCT
CCGTGAAGGTGTCCTGCAAGGCCTCCGGCTACTCCTTCACCTCCTACTA
CATCCACTGGGTGAAGCAGGCCCCCGGCCAGGGCCTGGAGTGGATCGGC
TGGATCTACCCCGGCTCCGGCAACACCAAGTACTCCGAGAAGTTCAAGG
GCCGCGCCACCCTGACCGCCGACACCTCCACCTCCACCGCCTACATGGA
GCTGCGCTCCCTGCGCTCCGACGACACCGCCGTGTACTTCTGCGCCCGC
GACGGCTGCTACGGCTTCGCCTACTGGGGCCAGGGCACCCTGGTGACCG
TGTCCTCA Hu1H7VHv1 (amino acid seq) (CDRs shown in bold and underlined)
SEQ ID NO: 19
QVQLVQSGAELKKPGASVKVSCKASGYSFTSYYIHWVKQAPGQGLEWIGWIYPGSGNTKYSEKFKGRATLTADTSTSTAYMELRSLRSDDTAVYFCARDGCYGFAYWGQGTLVTVSS Hu1H7VHv2 (nucleotide seq)
SEQ ID NO: 20
CAGGTGCAGCTGGTGCAGTCCGGCGCCGAGGTGAAGAAGCCCGGCGCCT
CCGTGAAGGTGTCCTGCAAGGCCTCCGGCTACTCCTTCACCTCCTACTA
CATCCACTGGGTGCGCCAGGCCCCCGGCCAGGGCCTGGAGTGGATCGGC
TGGATCTACCCCGGCTCCGGCAACACCAAGTACTCCGAGAAGTTCAAGG
GCCGCGCCACCCTGACCGCCGACACCTCCACCTCCACCGCCTACATGGA
GCTGCGCTCCCTGCGCTCCGACGACACCGCCGTGTACTTCTGCGCCCGC
GACGGCTGCTACGGCTTCGCCTACTGGGGCCAGGGCACCCTGGTGACCG
TGTCCTCA Hu1H7VHv2 (amino acid seq) (CDRs shown in bold and underlined)
SEQ ID NO: 21
QVQLVQSGAEVKKPGASVKVSCKASGYSFTSYYIHWVRQAPGQGLEWIGWIYPGSGNTKYSEKFKGRATLTADTSTSTAYMELRSLRSDDTAVYFCARDGCYGFAYWGQGTLVTVSS Hu1H7VHv3 (nucleotide seq)
SEQ ID NO: 22
CAGGTGCAGCTGGTGCAGTCCGGCGCCGAGGTGAAGAAGCCCGGCGCCT
CCGTGAAGGTGTCCTGCAAGGCCTCCGGCTACACCTTCACCTCCTACTA
CATCCACTGGGTGCGCCAGGCCCCCGGCCAGGGCCTGGAGTGGATGGGC
TGGATCTACCCCGGCTCCGGCAACACCAAGTACTCCGAGAAGTTCAAGG
GCCGCGCCACCATGACCGCCGACACCTCCACCTCCACCGCCTACATGGA
GCTGCGCTCCCTGCGCTCCGACGACACCGCCGTGTACTACTGCGCCCGC
GACGGCTGCTACGGCTTCGCCTACTGGGGCCAGGGCACCCTGGTGACCG
TGTCCTCA Hu1H7VHv3 (amino acid seq) (CDRs shown in bold and underlined)
SEQ ID NO: 23
QVQLVQSGAEVKKPGASVKVSCKASGYTFTSYYIHWVRQAPGQGLEWMGWIYPGSGNTKYSEKFKGRATMTADTSTSTAYMELRSLRSDDTAVYYCARDGCYGFAYWGQGTLVTVSS Hu1H7VHv4 (nucleotide seq)
SEQ ID NO: 24
CAGGTGCAGCTGGTGCAGTCCGGCGCCGAGGTGAAGAAGCCCGGCGCCT
CCGTGAAGGTGTCCTGCAAGGCCTCCGGCTACTCCTTCACCTCCTACTA
CATCCACTGGGTGCGCCAGGCCCCCGGCCAGGGCCTGGAGTGGATCGGC
TGGATCTACCCCGGCTCCGGCAACACCAAGTACTCCGAGAAGTTCAAGG
GCCGCGCCACCCTGACCGCCGACACCTCCACCTCCACCGCCTACATGGA
GCTGCGCTCCCTGCGCTCCGACGACACCGCCGTGTACTTCTGCGCCCGC
GACGGCTcCTACGGCTTCGCCTACTGGGGCCAGGGCACCCTGGTGACCG
TGTCCTCA Hu1H7VHv4 (amino acid seq) (CDRs shown in bold and underlined)
SEQ ID NO: 25
QVQLVQSGAEVKKPGASVKVSCKASGYSFTSYYIHWVRQAPGQGLEWIGWIYPGSGNTKYSEKFKGRATLTADTSTSTAYMELRSLRSDDTAVYFCARDGSYGFAYWGQGTLVTVSS Hu1H7VHv5 (nucleotide seq)
SEQ ID NO: 26
CAGGTGCAGCTGGTGCAGTCCGGCGCCGAGGTGAAGAAGCCCGGCGCCTCCGTGAAGGTGTCCTGCAAGGCCTCCGGCTACACCTTCACCTCCTACTACATCCACTGGGTGCGCCAGGCCCCCGGCCAGGGCCTGGAGTGGATGGGCTGGATCTACCCCGGCTCCGGCAACACCAAGTACTCCGAGAAGTTCAAGGGCCGCGCCACCATGACCGCCGACACCTCCACCTCCACCGCCTACATGGAGCTGCGCTCCCTGCGCTCCGACGACACCGCCGTGTACTACTGCGCCCGCGACGGCTcCTACGGCTTCGCCTACTGGGGCCAGGGCACCCTGGTGACCGTGTCCTCA Hu1H7VHv5 (amino acid seq) (CDRs shown in bold and underlined)
SEQ ID NO: 27
QVQLVQSGAEVKKPGASVKVSCKASGYTFTSYYIHWVRQAPGQGLEWMGWIYPGSGNTKYSEKFKGRATMTADTSTSTAYMELRSLRSDDTAVYYCARDGSYGFAYWGQGTLVTVSS Hu1H7VH signal peptide (nucleotide seq)
SEQ ID NO: 28
ATGGAGTTCGGCCTGTCCTGGCTGTTCCTGGTGGCCATCCTGAAGGGCGTGCAGTGC Hu1H7VH signal peptide (amino acid seq)
SEQ ID NO: 29
MEFGLSWLFLVAILKGVQC Hu1H7VH signal peptide (nucleotide seq)
SEQ ID NO: 30
ATGGACTGGACCTGGAGCATCCTTTTCTTGGTGGCAGCAGCAACAGGTGCCCACTCC Hu1H7VH signal peptide (amino acid seq)
SEQ ID NO: 31
MDWTWSILFLVAAATGAHS Hu1H7VLv1 (nucleotide seq)
SEQ ID NO: 32
GACATCCAGCTGACCCAGTCCCCCTCCTCCCTGTCCGCCTCCGTGGGCGACCGCGTGACCATCACCTGCAAGGCCTCCCAGTCCGTGGACTACGACGGCGACTCCTACATGAACTGGTACCAGCAGAAGCCCGGCAAGGCCCCCAAGTTCCTGATCTGCGCCGCCTCCAACCTGGAGTCCGGCGTGCCCTCCCGCTTCTCCGGCTCCGGCTCCGGCACCGACTTCACCCTGACCATCTCCTCCCTGCAGCCCGAGGACGCCGCCACCTACTACTGCCAGCAGTCCAACGAGGACCCCTTCACCTTCGGCCAGGGCACCAAGCTGGAGATCAAG Hu1H7VLv1 (amino acid seq) (CDRs shown in bold and underlined)
SEQ ID NO: 33
DIQLTQSPSSLSASVGDRVTITCKASQSVDYDGDSYMNWYQQKPGKAPKFLICAASNLESGVPSRFSGSGSGTDFTLTISSLQPEDAATYYCQQSNEDPFTFGQGTKLEIK Hu1H7VLv2 (nucleotide seq)
SEQ ID NO: 34
GACATCCAGCTGACCCAGTCCCCCTCCTCCCTGTCCGCCTCCGTGGGCGACCGCGTGACCATCACCTGCAAGGCCTCCCAGTCCGTGGACTACGACGGCGACTCCTACATGAACTGGTACCAGCAGAAGCCCGGCAAGGCCCCCAAGTTCCTGATCTAcGCCGCCTCCAACCTGGAGTCCGGCGTGCCCTCCCGCTTCTCCGGCTCCGGCTCCGGCACCGACTTCACCCTGACCATCTCCTCCCTGCAGCCCGAGGACGCCGCCACCTACTACTGCCAGCAGTCCAACGAGGACCCCTTCACCTTCGGCCAGGGCACCAAGCTGGAGATCAAG Hu1H7VLv2 (amino acid seq) (CDRs shown in bold and underlined)
SEQ ID NO: 35
DIQLTQSPSSLSASVGDRVTITCKASQSVDYDGDSYMNWYQQKPGKAPKFLIYAASNLESGVPSRFSGSGSGTDFTLTISSLQPEDAATYYCQQSNEDPFTFGQGTKLEIK Hu1H7VLv3 (nucleotide seq)
SEQ ID NO: 36
GACATCCAGCTGACCCAGTCCCCCTCCTCCCTGTCCGCCTCCGTGGGCGACCGCGTGACCATCACCTGCAAGGCCTCCCAGTCCGTGGACTACGACGGCGACTCCTACATGAACTGGTACCAGCAGAAGCCCGGCAAGGCCCCCAAGTTCCTGATCTGCGCCGCCTCCAACCTGGAGTCCGGCGTGCCCTCCCGCTTCTCCGGCTCCGGCTCCGGCACCGACTTCACCCTGACCATCTCCTCCCTGCAGCCCGAGGACTTCGCCACCTACTACTGCCAGCAGTCCAACGAGGACCCCTTCACCTTCGGCCAGGGCACCAAGCTGGAGATCAAG Hu1H7VLv3 (amino acid seq) (CDRs shown in bold and underlined)
SEQ ID NO: 37
DIQLTQSPSSLSASVGDRVTITCKASQSVDYDGDSYMNWYQQKPGKAPKFLICAASNLESGVPSRFSGSGSGTDFTLTISSLQPEDFATYYCQQSNEDPFTFGQGTKLEIK Hu1H7VLv4 (nucleotide seq)
SEQ ID NO: 38
GACATCCAGCTGACCCAGTCCCCCTCCTCCCTGTCCGCCTCCGTGGGCG

ACCGCGTGACCATCACCTGCAAGGCCTCCCAGTCCGTGGACTACGACGG

CGACTCCTACATGAACTGGTACCAGCAGAAGCCCGGCAAGGCCCCCAAG

TTCCTGATCTaCGCCGCCTCCAACCTGGAGTCCGGCGTGCCCTCCCGCT

TCTCCGGCTCCGGCTCCGGCACCGACTTCACCCTGACCATCTCCTCCCT

GCAGCCCGAGGACttCGCCACCTACTACTGCCAGCAGTCCAACGAGGAC

CCCTTCACCTTCGGCCAGGGCACCAAGCTGGAGATCAAG

Hu1H7VLv4 (amino acid seq) (CDRs shown in bold and underlined)
SEQ ID NO: 39
DIQLTQSPSSLSASVGDRVTITCKASQSVDYDGDSYMNWYQQKPGKAPK

FLIYAASNLESGVPSRFSGSGSGTDFTLTISSLQPEDFATYYCQQSNED

PFTFGQGTKLEIK

Hu1H7VL signal peptide (nucleotide seq)
SEQ ID NO: 40
ATGGACATGCGCGTGCCCGCCCAGCTGCTGGGCCTGCTGATGCTGTGGG

TGTCCGGCTCCTCCGGC

Hu1H7VL signal peptide (amino acid seq)
SEQ ID NO: 41
MDMRVPAQLLGLLMLWVSGSSG

BAC02037 (GI-21670055) Human acceptor used for heavy chain Framework Amino acid seq
SEQ ID NO: 42
QVQLVQSGAEVKKPGASVKVSCKASGYTFTSFGISWVRQAPGQGLEWMG

WISPYNGDTNYAQNLQGRVTMTTDTSTSTAYMELRSLRSDDTAVYYCAR

DRGSMSDYWGQGTLVTVSS

AAY33358 GI-63102905) Human acceptor used for light chain Framework Amino acid seq
SEQ ID NO: 43
DIQLTQSPSSLSASVGDRVTITCRASQGIRNDLGWYQQKPGKAPKLLIY

AASSLQSGVPSRFSGSGSGTDFTLTISSLQPEDFATYYCLQDYNYPPTF

GQGTKLEIK

Hu1H7VH no backmutation or CDR mutation
SEQ ID NO: 44
QVQLVQSGAEVKKPGASVKVSCKASGYSFTSYYTHWVRQAPGQGLEWMG

WIYPGSGNTKYSEKFKGRVTMTTDTSTSTAYMELRSLRSDDTAVYYCAR

DGCYGFAYWGQGTLVTVSS

Hu1H7VL no backmutation or CDR mutation
SEQ ID NO: 45
DIQLTQSPSSLSASVGDRVTITCKASQSVDYDGDSYMNWYQQKPGKAPK

LLIYAASNLESGVPSRFSGSGSGTDFTLTISSLQPEDFATYYCQQSNED

PFTFGQGTKLEIK

Hu1H7VH alternatives
SEQ ID NO: 46
QVQLVQSGAE-$X_1$-KKPGASVKVSCKASGY-$X_2$-FTSYYIHWV-$X_3$-QA

PGQGLEW-$X_4$-GWIYPGSGNTKYSEKFKGR-$X_5$-T-$X_6$-T-$X_7$-DTSTS

TAYMELRSLRSDDTAVY-$X_8$-CARDG-$X_9$-YGFAYWGQGTLVTVSS wherein -$X_1$- is V or L; -$X_2$- is S or T; -$X_3$- is R or K; -$X_4$- is M or I; -$X_5$- is V or A; -$X_6$- is M or L; -$X_7$- is T or A; -$X_8$- is Y or F; -$X_9$- is C or S.

Hu1H7VL alternatives
SEQ ID NO: 47
DIQLTQSPSSLSASVGDRVTITCKASQSVDYDGDSYMNWYQQKPGKAPK

-$Z_1$-LI-$Z_2$-AASNLESGVPSRFSGSGSGTDFTLTISSLQPED-$Z_3$-AT

YYCQQSNEDPFTFGQGTKLEIK wherein -$Z_1$- is L or F; -$Z_2$- is Y or C; -$Z_3$- is F or A.

Hu1H7VH CDR3 alternatives
SEQ ID NO: 48
DG-$X_9$-YGFAY wherein -$X_9$- is C or M or S or T, preferably C humanized 1H7 light chain constant region (with R) (common for v1-v4)
SEQ ID NO: 49
RTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPV

TKSFNRGEC humanized 1H7 heavy chain constant region (common for v1-v5) IgG1
SEQ ID NO: 50
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKRV

EPKSCDKTHTCPPCPAPELLGGPSVFLFPPKPKDTLMISRTPEVTCVVV

DVSHEDPEVKFNWYVDGVEVHNVKTKPREEQYNSTYRVVSVLTVLHQDW

LNGKEYKCKVSNKALPAPIEKTISKAKGQPREPQVYTLPPSREEMTKNQ

VSLTCLVKGFYPSDIAVEWESNGQPENNYKTTPPVLDSDGSFFLYSKLT

VDKSRWQQGNVFSCSVMHEALHNHYTQKSLSLSPGK humanized 1H7 light chain constant region (without R) (common for v1-v4)
SEQ ID NO: 51
TVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVT

KSFNRGEC humanized 1H7 heavy chain constant region (G1m3 allotype)
SEQ ID NO: 52
ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKRV
EPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLT
VDKSRWQQGNVFSCSVMHEALHNHYTQKSLSLSPGK humanized 1H7 light chain version 3 (variable region + constant region with Arginine)
SEQ ID NO: 53
DIQLTQSPSSLSASVGDRVTITCKASQSVDYDGDSYMNWYQQKPGKAPK
FLICAASNLESGVPSRFSGSGSGTDFTLTISSLQPEDFATYYCQQSNED
PFTFGQGTKLEIKRTVAAPSVFIFPPSDEQLKSGTASVVCLLNNFYPRE
AKVQWKVDNALQSGNSQESVTEQDSKDSTYSLSSTLTLSKADYEKHKVY
ACEVTHQGLSSPVTKSFNRGEC humanized 1H7 light chain version 3 (variable region + constant region without Arginine)
SEQ ID NO: 54
DIQLTQSPSSLSASVGDRVTITCKASQSVDYDGDSYMNWYQQKPGKAPK
FLICAASNLESGVPSRFSGSGSGTDFTLTISSLQPEDFATYYCQQSNED
PFTFGQGTKLEIKTVAAPSVFIFPPSDEQLKSGTASVVCLLNNFYPREA
KVQWKVDNALQSGNSQESVTEQDSKDSTYSLSSTLTLSKADYEKHKVYA
CEVTHQGLSSPVTKSFNRGEC humanized 1H7 heavy chain version 3 (variable region + constant region)
SEQ ID NO: 55
QVQLVQSGAEVKKPGASVKVSCKASGYTFTSYYIHWVRQAPGQGLEWMG
WIYPGSGNTKYSEKFKGRATMTADTSTSTAYMELRSLRSDDTAVYYCAR
DGCYGFAYWGQGTLVTSSASTKGPSVFPLAPSSKSTSGGTAALGCLVK
DYFPEPVTVSWNSGALTSGVHTFPAVLQSSGLYSLSSVVTVPSSSLGTQ
TYICNVNHKPSNTKVDKRVEPKSCDKTHTCPPCPAPELLGGPSVFLFPP
KPKDTLMISRTPEVTCVVVDVSHEDPEVKFNWYVDGVEVHNVKTKPREE
QYNSTYRVVSVLTVLHQDWLNGKEYKCKVSNKALPAPIEKTISKAKGQP
REPQVYTLPPSREEMTKNQVSLTCLVKGFYPSDIAVEWESNGQPENNYK
TTPPVLDSDGSFFLYSKLTVDKSRWQQGNVFSCSVMHEALHNHYTQKSL
SLSPGK humanized 1H7 heavy chain version 3 (variable region + constant region G1m3 allotype)
SEQ ID NO: 56
QVQLVQSGAEVKKPGASVKVSCKASGYTFTSYYIHWVRQAPGQGLEWMG
WIYPGSGNTKYSEKFKGRATMTADTSTSTAYMELRSLRSDDTAVYYCAR
DGCYGFAYWGQGTLVTSSASTKGPSVFPLAPSSKSTSGGTAALGCLVK
DYFPEPVTVSWNSGALTSGVHTFPAVLQSSGLYSLSSVVTVPSSSLGTQ
TYICNVNHKPSNTKVDKRVEPKSCDKTHTCPPCPAPELLGGPSVFLFPP
KPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQP
REPQVYTLPPSREEMTKNQVSLTCLVKGFYPSDIAVEWESNGQPENNYK
TTPPVLDSDGSFFLYSKLTVDKSRWQQGNVFSCSVMHEALHNHYTQKSL
SLSPGK humanized 1H7 heavy chain constant region (IgG2)
SEQ ID NO: 57
ASTKGPSVFPLAPCSRSTSESTAALGCLVKDYFPEPVTVSWNSGALTSG
VHTFPAVLQSSGLYSLSSVVTVPSSNFGTQTYTCNVDHKPSNTKVDKTV
ERKCCVECPPCPAPPVAGPSVFLFPPKPKDTLMISRTPEVTCVVVDVSH
EDPEVQFNWYVDGVEVHNAKTKPREEQFNSTFRVVSVLTVVHQDWLNGK
EYKCKVSNKGLPAPIEKTISKTKGQPREPQVYTLPPSREEMTKNQVSLT
CLVKGFYPSDIAVEWESNGQPENNYKTTPPMLDSDGSFFLYSKLTVDKS
RWQQGNVFSCSVMHEALHNHYTQKSLSLSPGK humanized 1H7 heavy chain constant region (G1m1 allotype)
SEQ ID NO: 58
ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKRV
EPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLT
VDKSRWQQGNVFSCSVMHEALHNHYTQKSLSLSPGK

What is claimed is:

1. A nucleic acid or nucleic acids encoding a heavy chain having the sequence of SEQ ID NO:56 with or without the C-terminal lysine and a light chain having the sequence of SEQ ID NO:53.

2. A host cell comprising the nucleic acid or nucleic acids of claim 1.

3. A pharmaceutical composition comprising an antibody comprising a heavy chain having the sequence of SEQ ID NO:56 with or without the C-terminal lysine and a light chain having the sequence of SEQ ID NO:53, and a physiologically acceptable carrier.

4. A method of treating a patient having or at risk of a Lewy body disease, comprising administering to the patient an effective regime of the pharmaceutical composition of claim 3.

5. The method of claim 4, wherein the disease is Parkinson's disease.

6. The method of claim 4, wherein decline of cognitive function in the patient is inhibited.

7. The method of claim 4, wherein neuritic and/or axonal alpha synuclein aggregates are reduced.

8. The method of claim 4, wherein neuritic dystrophy in the patient is reduced.

9. The method of claim 4, wherein synaptic and/or dendritic density is preserved.

10. The method of claim 4, wherein the method preserves synaptophysin and/or MAP2 in the patient.

11. A method of reducing Lewy body formation in a patient having or at risk of a Lewy body disease, comprising administering to the patient an effective amount of the pharmaceutical composition of claim 3.

12. A method of inhibiting synuclein aggregation or clearing Lewy bodies or synuclein aggregates in a patient having or at risk of a Lewy body disease, comprising administering to the patient an effective amount of the pharmaceutical composition of claim 3.

13. A method of detecting Lewy bodies in a patient having or at risk of a Lewy body disease, comprising administering to the patient an effective amount of an antibody comprising a heavy chain having the sequence of SEQ ID NO: 56 with or without the C-terminal lysine and a light chain having the sequence of SEQ ID NO:53, and a physiologically acceptable carrier, wherein the antibody binds to Lewy bodies; and detecting bound antibody in the patient.

14. The method of claim 13, wherein the antibody is labeled.

15. A method of producing an antibody, comprising culturing cells transformed with a nucleic acid or nucleic acids encoding the heavy and light chains of the antibody, so that the cells secrete the antibody; and purifying the antibody from cell culture media; wherein the antibody comprises a heavy chain having the sequence of SEQ ID NO: 56 with or without the C-terminal lysine and a light chain having the sequence of SEQ ID NO: 53.

16. A method of producing a cell line producing an antibody, comprising introducing a vector encoding heavy and light chains of an antibody and a selectable marker into cells; propagating the cells under conditions to select for cells having increased copy number of the vector; isolating single cells from the selected cell; and banking cells cloned from a single cell selected based on yield of antibody; wherein the antibody comprises a heavy chain having the sequence of SEQ ID NO: 56 with or without the C-terminal lysine and a light chain having the sequence of SEQ ID NO:53.

17. The method of claim 16, further comprising propagating the cells under selective conditions and screening for cell lines naturally expressing and secreting at least 100 mg/L/106 cells/24 h.

\* \* \* \* \*